US008088081B2

(12) United States Patent
Field et al.

(10) Patent No.: US 8,088,081 B2
(45) Date of Patent: Jan. 3, 2012

(54) CORE BIOPSY DEVICE

(75) Inventors: Steven E. Field, Grand Rapids, MI (US);
Brian R. Mulder, Rockford, MI (US);
Michael Johnson, West Olive, MI (US);
Todd Ireland, Coopersville, MI (US);
Steve Haeske, Allendale, MI (US);
Mark Vander Veen, Grand Haven, MI (US)

(73) Assignee: Inrad, Inc., Grand Rapids, MI (US)

( * ) Notice: Subject to any disclaimer, the term of this patent is extended or adjusted under 35 U.S.C. 154(b) by 682 days.

(21) Appl. No.: 10/908,427

(22) Filed: May 11, 2005

(65) Prior Publication Data
US 2006/0030785 A1 Feb. 9, 2006

Related U.S. Application Data

(60) Provisional application No. 60/521,518, filed on May 11, 2004.

(51) Int. Cl.
*A61B 10/00* (2006.01)
(52) U.S. Cl. ......................................... 600/567; 600/568
(58) Field of Classification Search .................. 600/567, 600/562, 564–566, 568; 606/170
See application file for complete search history.

(56) References Cited

U.S. PATENT DOCUMENTS

| 3,007,471 | A | * | 11/1961 | McClure, Jr. ............. 600/567 |
| 4,368,734 | A | * | 1/1983 | Banko .......................... 606/170 |
| 4,651,752 | A | | 3/1987 | Fuerst |
| 4,708,147 | A | * | 11/1987 | Haaga .......................... 600/567 |
| 4,735,215 | A | | 4/1988 | Goto et al. |
| 4,776,346 | A | | 10/1988 | Beraha et al. |
| 4,781,202 | A | | 11/1988 | Janese |
| 4,881,551 | A | | 11/1989 | Taylor |
| 4,893,635 | A | | 1/1990 | de Groot et al. |
| 4,924,878 | A | | 5/1990 | Nottke |
| 4,926,877 | A | | 5/1990 | Bookwalter |
| 4,958,625 | A | | 9/1990 | Bates et al. |
| 5,036,860 | A | | 8/1991 | Leigh et al. |
| 5,090,419 | A | | 2/1992 | Palestrant |
| 5,111,828 | A | | 5/1992 | Kornberg et al. |
| 5,133,360 | A | | 7/1992 | Spears |
| 5,133,713 | A | | 7/1992 | Huang et al. |
| RE34,056 | E | | 9/1992 | Lindgren et al. |

(Continued)

FOREIGN PATENT DOCUMENTS

CA 1185491 4/1985

(Continued)

*Primary Examiner* — Max Hindenburg
*Assistant Examiner* — Emily Lloyd
(74) *Attorney, Agent, or Firm* — McGarry Bair PC

(57) ABSTRACT

A core biopsy device comprises an outer cutting cannula in telescoping register with an inner spoon cannula. The outer cutting cannula is provided at a distal end with an arcuate excising blade that is biased radially inwardly to extend beyond the longitudinal axis of the cannula. The inner spoon cannula terminates at a distal end in an arcuate wall to form a biopsy sample spoon for supporting a biopsy sample thereon. The outer cutting cannula can be rotated relative to the inner spoon cannula so that the excising blade can excise the biopsy sample from the surrounding tissue. After removal of the core biopsy device from the tissue, the outer cutting cannula can be retracted away from the inner spoon cannula to reveal the biopsy sample and enable the sample to be removed from the biopsy device in a relatively undisturbed condition.

36 Claims, 81 Drawing Sheets

U.S. PATENT DOCUMENTS

| | | | |
|---|---|---|---|
| 5,156,160 A | 10/1992 | Bennett | |
| 5,161,542 A | 11/1992 | Palestrant | |
| 5,183,054 A | 2/1993 | Burkholder et al. | |
| 5,188,118 A | 2/1993 | Terwilliger | |
| 5,195,533 A | 3/1993 | Chin et al. | |
| 5,197,484 A * | 3/1993 | Kornberg et al. | 600/567 |
| 5,224,488 A | 7/1993 | Neuffer | |
| 5,249,583 A | 10/1993 | Mallaby et al. | |
| 5,251,641 A | 10/1993 | Xavier | |
| 5,353,804 A | 10/1994 | Kornberg et al. | |
| 5,368,045 A | 11/1994 | Clement et al. | |
| 5,375,608 A | 12/1994 | Tiefenbrun et al. | |
| 5,462,062 A | 10/1995 | Rubinstein et al. | |
| 5,477,862 A | 12/1995 | Haaga | |
| 5,546,957 A | 8/1996 | Heske | |
| 5,634,473 A | 6/1997 | Goldenberg et al. | |
| 5,655,542 A | 8/1997 | Weilandt | |
| 5,709,697 A | 1/1998 | Ratcliff et al. | |
| 5,752,923 A | 5/1998 | Terwilliger | |
| 5,779,647 A | 7/1998 | Chau et al. | |
| 5,788,651 A | 8/1998 | Weilandt | |
| 5,807,277 A | 9/1998 | Swaim | |
| 5,810,806 A | 9/1998 | Ritchart et al. | |
| 5,827,305 A | 10/1998 | Gordon | |
| 5,842,999 A | 12/1998 | Pruitt et al. | |
| 5,857,982 A | 1/1999 | Milliman et al. | |
| 5,882,316 A | 3/1999 | Chu et al. | |
| 5,910,121 A * | 6/1999 | Paolo et al. | 600/567 |
| 5,913,857 A | 6/1999 | Ritchart et al. | |
| 5,928,162 A | 7/1999 | Giurtino et al. | |
| 5,951,489 A | 9/1999 | Bauer | |
| 5,961,534 A | 10/1999 | Banik et al. | |
| 5,989,196 A | 11/1999 | Chu et al. | |
| 5,989,197 A | 11/1999 | Avaltroni | |
| 5,993,399 A | 11/1999 | Pruitt et al. | |
| 6,007,495 A | 12/1999 | Matula | |
| 6,007,497 A | 12/1999 | Huitema | |
| 6,019,733 A | 2/2000 | Farascioni | |
| 6,050,955 A | 4/2000 | Bryan et al. | |
| 6,083,237 A | 7/2000 | Huitema et al. | |
| 6,136,014 A | 10/2000 | Sirimanne et al. | |
| 6,142,955 A | 11/2000 | Farascioni et al. | |
| 6,165,136 A | 12/2000 | Nishtala | |
| 6,176,834 B1 | 1/2001 | Chu et al. | |
| 6,193,673 B1 | 2/2001 | Viola et al. | |
| 6,248,081 B1 | 6/2001 | Nishtalas et al. | |
| 6,273,862 B1 | 8/2001 | Privitera et al. | |
| 6,293,945 B1 | 9/2001 | Parins et al. | |
| 6,395,011 B1 * | 5/2002 | Johanson et al. | 600/567 |
| 6,416,484 B1 * | 7/2002 | Miller et al. | 600/564 |
| 6,432,064 B1 | 8/2002 | Hibner et al. | |
| 6,436,054 B1 | 8/2002 | Viola et al. | |
| 6,443,910 B1 | 9/2002 | Krueger et al. | |
| 6,488,636 B2 | 12/2002 | Bryan et al. | |
| 6,517,498 B1 | 2/2003 | Burbank et al. | |
| 6,551,254 B2 | 4/2003 | Nishtalas et al. | |
| 6,554,779 B2 | 4/2003 | Viola et al. | |
| 6,569,176 B2 * | 5/2003 | Jesseph | 600/564 |
| 6,610,020 B2 | 8/2003 | Voegele | |
| 6,620,111 B2 | 9/2003 | Stephens et al. | |
| 2001/0011156 A1 | 8/2001 | Viola et al. | |
| 2002/0045842 A1 | 4/2002 | Van Bladel et al. | |
| 2003/0153843 A1 | 8/2003 | Nishtalas et al. | |
| 2004/0019299 A1 | 1/2004 | Ritchart et al. | |

FOREIGN PATENT DOCUMENTS

| | | |
|---|---|---|
| DE | 20010879 | 10/2000 |
| EP | 0852127 | 7/1998 |
| EP | 1252863 A1 | 10/2002 |
| SU | 1537232 A1 | 1/1990 |
| WO | WO 9508291 | 3/1995 |
| WO | WO 9508292 | 3/1995 |
| WO | WO 9508946 | 4/1995 |
| WO | WO 9726835 | 7/1997 |
| WO | 03077767 | 9/2003 |

* cited by examiner

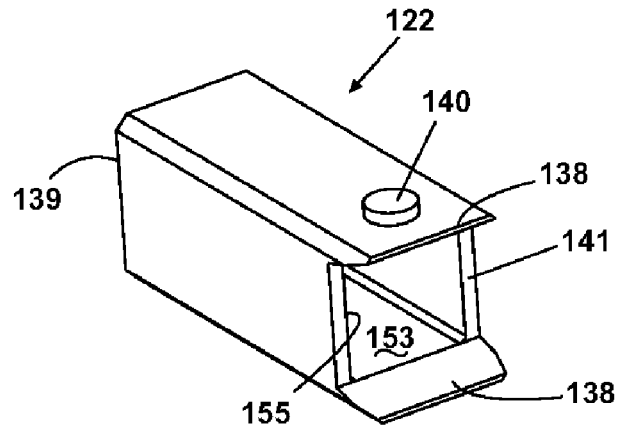
Fig. 16A
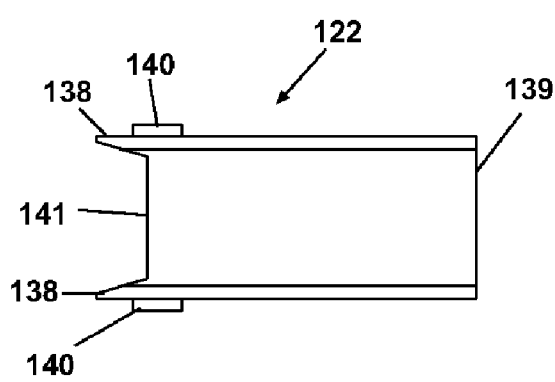 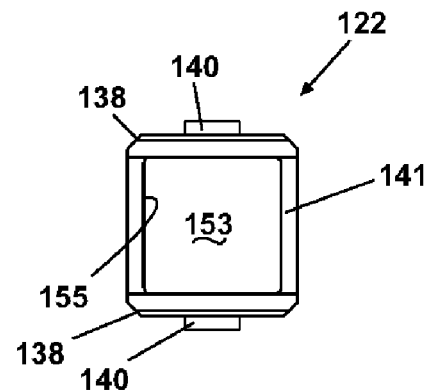
Fig. 16B Fig. 16D
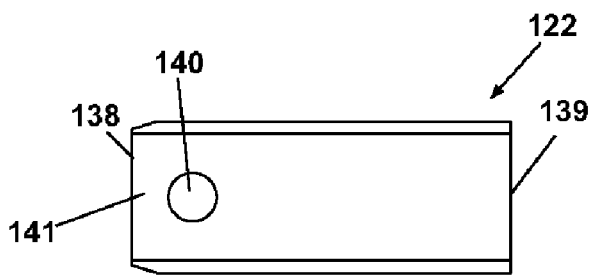
Fig. 16C

CORE BIOPSY DEVICE

CROSS-REFERENCE TO RELATED APPLICATION

This application claims the benefit of U.S. provisional application Ser. No. 60/521,518, filed May 11, 2004, which is incorporated herein in its entirety.

FIELD OF THE INVENTION

The invention relates to a core biopsy device for obtaining biopsy samples from tissue, and more particularly, to a core biopsy device having a rotatable excising finger for separating the core biopsy sample from the tissue.

DESCRIPTION OF THE RELATED ART

It is frequently necessary to sample or remove a sample from a suspect tissue for testing. In humans, such a sample removal is particularly useful in the diagnosis and treatment of cancerous or pre-cancerous conditions. In the case of suspected cancer, particularly cancer of the breast, early detection and diagnosis is critical to the success of the patient's treatment and recovery.

Various techniques are available to aid in detection and diagnosis, including physical examination and imaging, such as mammography, x-ray, ultrasound, magnetic resonance imaging (MRI), and the like. When a condition is detected that suggests the possibility of cancer, a biopsy can be performed to obtain tissue samples for a complete diagnosis.

One biopsy technique frequently performed is a core biopsy, which uses a core biopsy device in which a cannula is inserted into the tissue of interest, thereby coring a biopsy sample from the tissue having a cross section similar to that of the cannula, and which is retained within the cannula. The cannula, with the biopsy sample, is then removed from the tissue, followed by cytological and/or histological analysis of the sample.

One group of core biopsy devices is based on the combination of a notched inner stylet and an outer severing cannula. The stylet is retained within the lumen of the outer cannula such that the pointed end of the stylet closes off the open end of the cannula. The stylet and cannula are advanced into the tissue mass until they are near the desired biopsy site. The stylet is then advanced relative to the outer cannula to expose the notch to the biopsy site where the tissue prolapses into the notch. The outer cannula is then advanced to sever the tissue in the notch. The disadvantage of this method is that it produces a small core biopsy relative to the outer cannula size since the cross section of the sample is substantially equal to the cross section of the stylet notch, which is substantially smaller than the cross section of the outer cannula. The advantage of this method is that the sample is completely severed from the tissue mass and securely retained within the notch.

Another group of core biopsy devices is based on a coring cannula in combination with a non-notched stylet. The stylet is used to plug the end of the coring cannula during the insertion of the coring cannula into the tissue adjacent the biopsy site. The coring cannula is then advanced relative to the stylet into the biopsy site to retain a sample within the coring cannula. The advantage of this device is that a full core biopsy sample is obtained. That is, the cross section of the sample is substantially equal to the cross section of the coring cannula. The full core sample provides a much larger sample which is highly advantageous.

The disadvantage of this full core device is that the end of the sample is not positively severed from the tissue mass, creating the possibility that the biopsy sample will be pulled out of the coring cannula upon the withdrawal of the coring cannula. This can happen if the forces holding the sample in the coring cannula are not sufficient to tear the end of the sample from the tissue mass. Since the sample normally comprises wetted tissue that completely fills the coring cannula, the suction force and/or the frictional force between the tissue sample and the inner wall of the coring cannula are the dominate forces for retaining the sample in the cannula. However, if these forces are not sufficient to tear the end of the sample from the tissue mass, the sample will be pulled out of the coring cannula upon the removal of the coring cannula. Some practitioners pivot the biopsy device in hopes that the end of the cannula will at least partially sever the attached portion of the sample. However, this is not preferred as it increases the damage to the remaining tissue.

Attempts have been made to improve the severing of the sample from the tissue mass for the full core device. In some cases, the interior of the coring cannula is provided with a raceway in which a severing finger could be advanced/retracted. After the advancing of the cannula to take the core sample, the severing finger is advanced, guided by the raceway, to sever the tissue. In some cases, when the finger is advanced, it closes the end of the coring cannula and is left in the advanced position during removal. A disadvantage of this method is that the sample is not truly a full core sample since part of the interior of the cannula was reserved for the raceway. If the sample produced by the cannula with the raceway was the same size as the full core sample, the cannula with the raceway would require a larger cross sectional cannula, which is not desirable. In the biopsy art, it is highly desirable to minimize the cross section of the cannula to minimize the damage to the surrounding tissue and to minimize the invasiveness of the procedure. Generally, the smaller the cross section, the less pain the patient experiences after the procedure, and the more desirable the device.

Another alternative to severing the sample end in a full core device comprises the addition of a cutting cannula that circumscribes the coring cannula. The cutting cannula has a cutting element that severs the sample within the coring cannula or at the tip of the coring cannula. For example, the device in U.S. Pat. No. 5,655,542 discloses fingers that are deflected through windows in the coring cannula into the interior of the coring cannula to sever the tissue. The internally severing devices have the disadvantage in that the resulting sample is shorter in length than the amount of tissue that is received within the interior since the finger enters the coring cannula proximal to the coring cannula tip. Since not all of the sample received within the coring cannula is severed, extra care must be taken to ensure that the lesion or other relevant portion of the tissue to be biopsied lies behind the end location of the severing finger. This is made more difficult in that the practitioner cannot use the end of the cannula for marking the extent of the biopsy specimen.

U.S. Pat. No. 6,551,254 discloses another approach using a tubular cutting member slidably mounted to the coring cannula, with the tubular cutting member having a spring memory finger that deflects downwardly over the coring cannula tip to close off the coring cannula opening and sever the sample from the tissue mass. The finger has a sharpened edge to affect the cutting. The disadvantage of this structure is that the coring and cutting cannulae are made from multiple pieces and include built in stops, which increase the assembly requirements and cost of the device. Also, the cutting finger needs to be of sufficient width to span the coring cannula opening to ensure the complete severing of the end of the specimen.

Another disadvantage of all of the full core devices is that they rely on the relative movement between the coring cannula and the stylet to expel the sample from the interior of the coring cannula. The use of the stylet to force out the sample can damage the sample. The damage can be great enough to render the sample unsuitable for testing. This can be very detrimental since some lesions being sampled are small enough that the entire lesion is contained within the sample. For larger lesions, some practitioners will take multiple samples to allow for potential damage of one of the samples. This practice increases the invasiveness of the procedure and the pain to the patient.

While there have been many attempts in the art to produce a workable core biopsy device, there is still a strong need for a core biopsy device that minimizes patient discomfort, insures a complete excision of the biopsy sample from the surrounding tissue, enables the biopsy sample to be removed from the device without disturbance of the sample, and is simple and cost effective to manufacture.

SUMMARY OF THE INVENTION

The invention relates to a biopsy apparatus for the percutaneous removal of a specimen from a tissue mass. The biopsy apparatus comprises an outer cannula defining a lumen and a longitudinal axis. The outer cannula has a proximal end and a distal end, with an excising finger extending from the distal end. An inner cannula is received within the lumen and has a proximal end and a distal end. An actuator is operably coupled to the outer cannula for axially moving the outer cannula relative to the inner cannula from an inserting to an excising position where the excising finger extends beyond the distal end of the inner cannula, and rotating the outer cannula about the longitudinal axis when the outer cannula is in the excising position.

The excising finger is adapted for resilient flexure; preferably for flexure alternating between a first position toward the longitudinal axis and a second position away from the longitudinal axis. The excising finger can ride along the inner cannula during the axial movement to the excising position. The shape of the excising finger is at least one of arcuate, rectilinear, and trapezoidal. The excising finger preferably extends longitudinally from the distal end of the outer cannula, and preferably extends at least to the longitudinal axis.

The actuator can simultaneously move the outer cannula and the inner cannula to the excising position. Alternatively, the actuator can sequentially move the outer cannula and the inner cannula to the excising position.

The inner cannula preferably comprises a spoon portion that terminates at the distal end for supporting a biopsy sample. The spoon portion can comprise an arcuate cross section, which preferably spans an arc of 180 degrees or less. The spoon portion can terminate in a sharpened edge.

In an alternative cannula design, the inner cannula has a lateral opening near the distal end and the excising finger extends through the opening in the excising position.

A stylet can be provided to substantially close off the inner cannula in the inserting position. Preferably, the actuator, inner cannula, and outer cannula collectively define an integrated self-contained hand-holdable device that can be easily and conveniently handled by a user to effect operation of the biopsy apparatus.

The actuator preferably rotates the outer cannula for at least a partial revolution. Preferably, the cannula is rotated at least one revolution. Even more preferably, the cannula is rotated at least 1½ revolutions.

In another aspect, the invention also relates to a biopsy apparatus for the percutaneous removal of a specimen from a tissue mass, where the biopsy apparatus comprises an outer cannula defining a lumen and a longitudinal axis, with the outer cannula having a proximal end and a distal end, an inner cannula received within the lumen of the outer cannula and having a proximal end and a distal end, with the inner cannula having a spoon portion that terminates at the distal end, and wherein upon the performance of a biopsy, the specimen is received within the lumen and supported on the spoon portion, and relatively moving the cannulae exposes the specimen supported on the spoon portion to permit the removal of the specimen from the spoon portion.

In yet another aspect, the invention also relates to a method of conducting a percutaneous biopsy by removing a core specimen from a predetermined site in a tissue mass. The method comprises advancing an open-tipped cannula into the predetermined site in the tissue mass to form a specimen core containing at least a portion of the tissue at the predetermined site, with an end of the specimen core still attached to the tissue mass, automatically extending an excising finger into the attached end of the core specimen, and automatically rotating the excising finger to sever the attached end of the core specimen from the surrounding tissue.

The steps of advancing the open-tipped cannula and automatically extending the excising finger can be done sequentially or simultaneously. The simultaneous advancement of the cannula and the excising finger can be implemented by the finger being mounted to the cannula and automatically extending the cannula.

The step of rotating the excising finger is preferably done after the completing of the extending of the excising finger.

The invention also relates to a method of conducting a percutaneous biopsy by removing a core specimen from a predetermined site in a tissue mass, wherein the specimen core is supported by the biopsy device for easy removal by the practitioner. The method comprises: advancing an open-tipped cannula defining a lumen into the predetermined site in the tissue mass to at least partially form a specimen core containing at least a portion of the tissue at the predetermined site; advancing an inner cannula terminating in a spoon portion within the lumen of the outer cannula such that the specimen core is supported by the spoon portion; severing the specimen core from the tissue mass; withdrawing the open-tipped cannula and inner cannula from the tissue mass; and relatively moving the cannulae to expose the specimen core supported on the spoon portion to permit the removal of the specimen core therefrom.

The insertion of the spoon-shaped specimen support can be conducted prior to the advancement of the open-tipped cannula. The spoon-shaped support can also be advanced along with the open-tipped cannula.

The method further comprises retracting the open-tipped cannula to expose the independently supported specimen. The severing of the specimen core can be at least partially accomplished by the advancing of the open-tipped cannula. The severing of the specimen core can further comprise rotating one of the open-tipped cannula and the inner cannula. At least one of the open-tipped cannula and the inner cannula can be rotated at least a partial revolution. Preferably, it is rotated at least one revolution.

The at least one of the open-tipped cannula and the inner cannula can comprise an excising finger for severing the specimen core upon rotation. The outer cannula can comprise a spoon portion that terminates at a distal end for supporting a biopsy sample.

BRIEF DESCRIPTION OF THE DRAWINGS

In the drawings:

FIGS. 16A-D are alternate views of a retraction body comprising a portion of the actuator assembly illustrated in FIG. 13.

DESCRIPTION OF AN EMBODIMENT OF THE INVENTION

Figure 1:
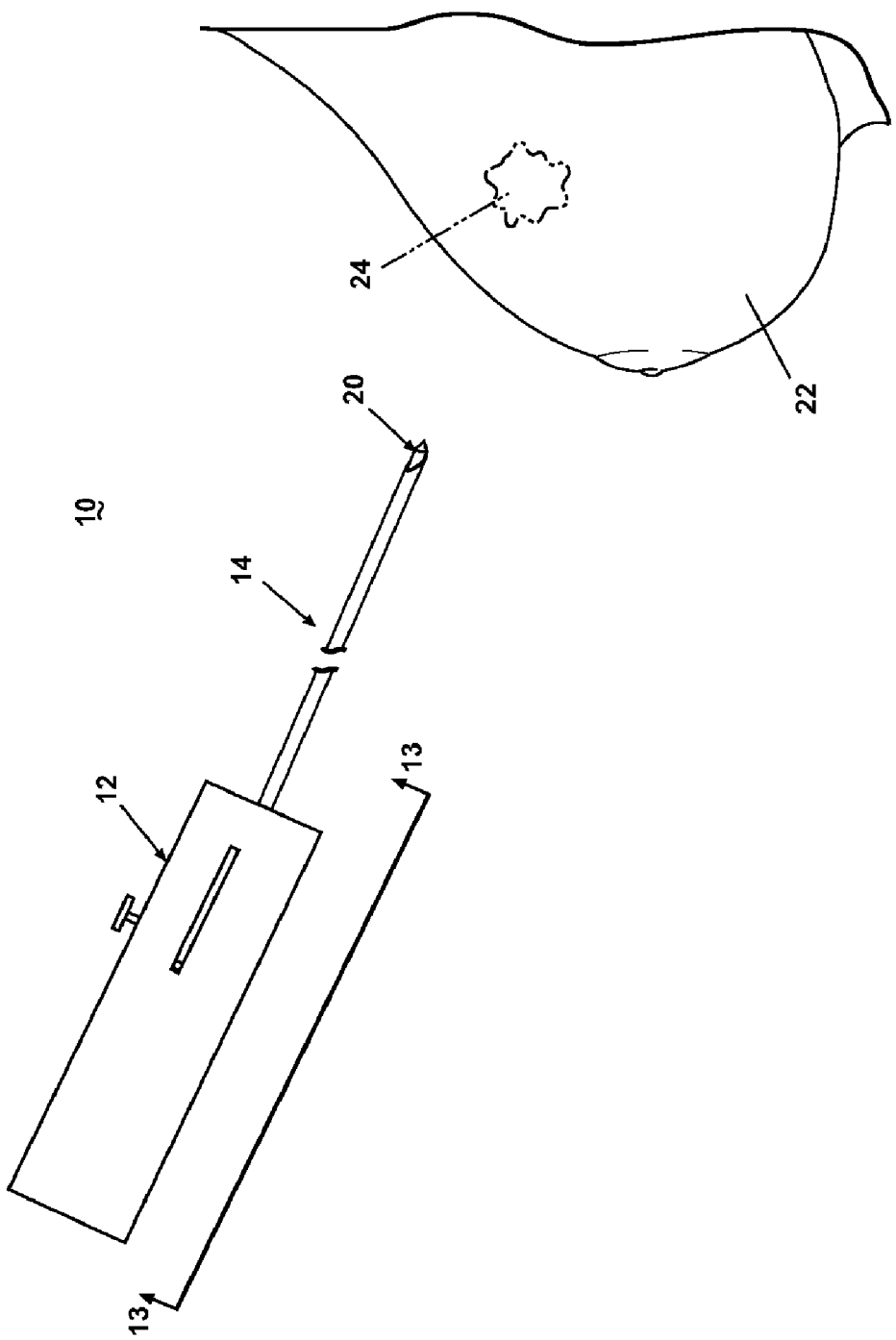
FIG. 1 is a perspective view of a lesion within a tissue mass and a first embodiment of a core biopsy device comprising an actuator assembly and a cannula assembly according to the invention for obtaining a core biopsy sample from the lesion.

Referring now to the drawings, and specifically to FIG. 1, a core biopsy device 10 is illustrated comprising an actuator assembly 12 structurally and operably connected to a cannula assembly 14. The cannula assembly 14 is utilized to penetrate a tissue mass 22 for obtaining a core biopsy sample from a lesion 24 as more specifically described hereinafter. An embodiment of the actuator assembly 12 is described and illustrated herein comprising an automated, integrated handheld device capable of controlling the acquisition and removal of the core biopsy sample from the lesion 24. An actuator assembly 12 is preferably utilized that is capable of automated firing of the cannula assembly 14, with the additional capability of firing a pair of telescoping cannulae and a stylet with one triggering action, or firing an inner cannula and an outer cannula independently. As described and illustrated herein, the actuator assembly 12 is capable of controlled rotation of the outer cannula around the inner cannula after the cannulae have been fired to excise the core biopsy sample from the surrounding lesion 24.

Figure 2:
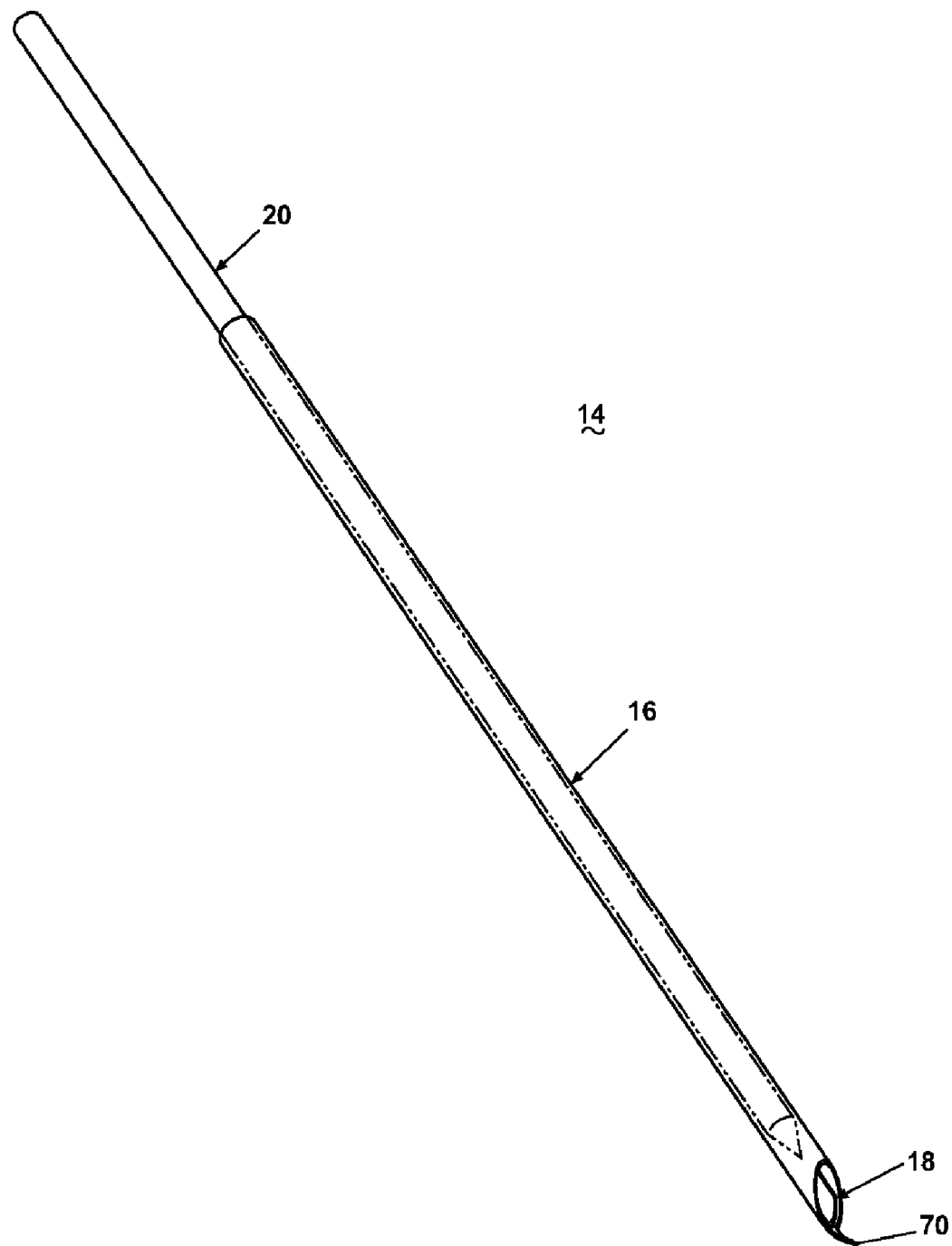
FIG. 2 is a perspective view of a cannula assembly comprising a coring cannula, a spoon cannula, and a stylet, with the coring cannula in an excising position.
Figure 3:
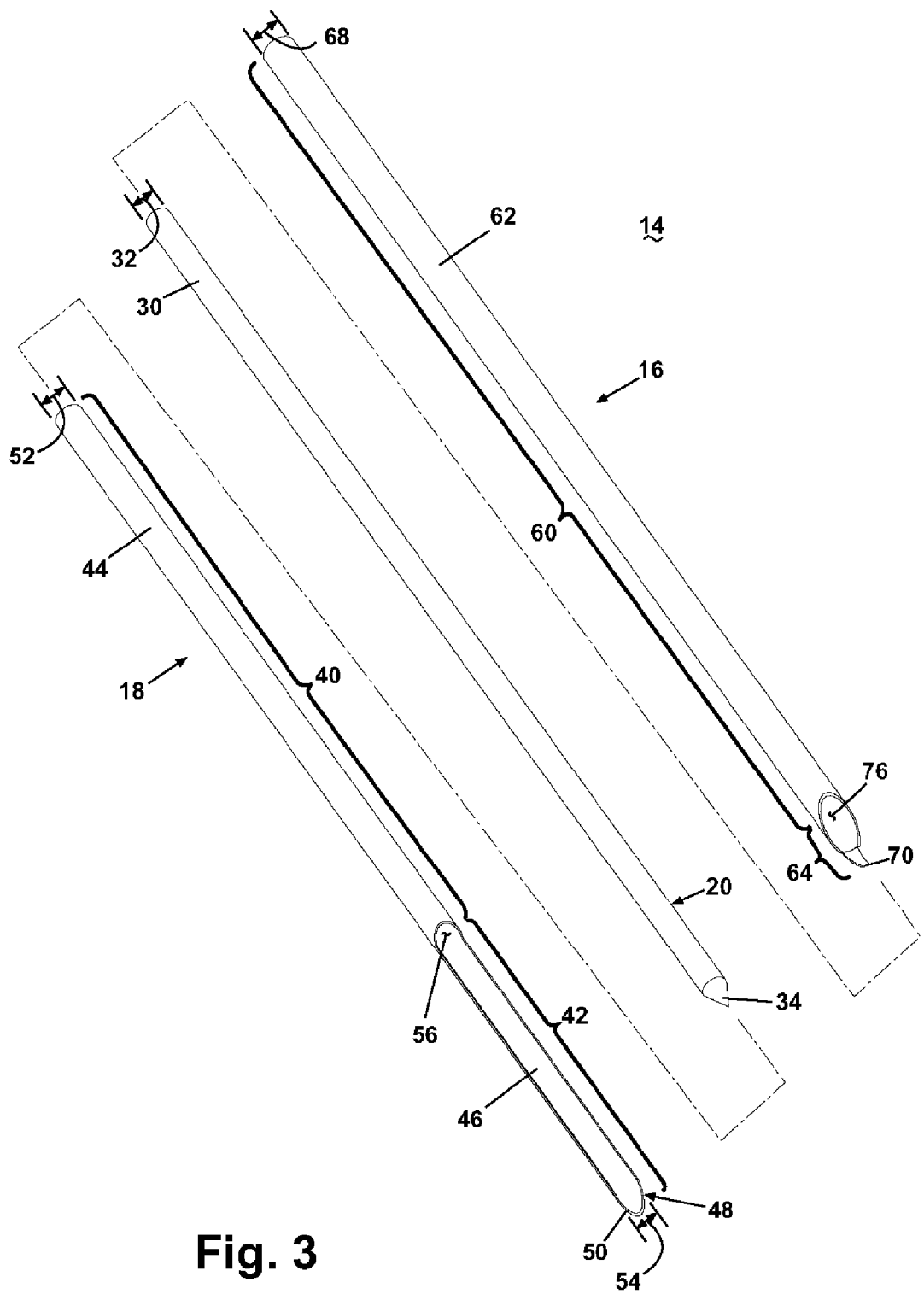
FIG. 3 is an exploded view of the coring cannula, spoon cannula, and stylet comprising the cannula assembly illustrated in FIG. 2.

Referring now to FIGS. 2-6, the cannula assembly 14 comprises a coring cannula 16, a spoon cannula 18, and a stylet 20 in coaxially telescoping relationship, as illustrated in FIGS. 2 and 3. As used herein with respect to the coring cannula 16, the spoon cannula 18, and the stylet 20, the terms "distal" and "forward" refer to or in a direction toward that end of the cannulae 16,18 and/or the stylet 20 that is directed toward the lesion 24 and away from the actuator assembly 12. "Proximal" or "rearward" thus refers to or in a direction toward that end of the cannulae 16,18 and/or the stylet 20 that is directed away from the lesion 24 and toward the actuator assembly 12. Preferably, the coring cannula 16, the spoon cannula 18, and the stylet 20 are fabricated of a well-known surgically suitable material, such as stainless steel.

Figure 4:
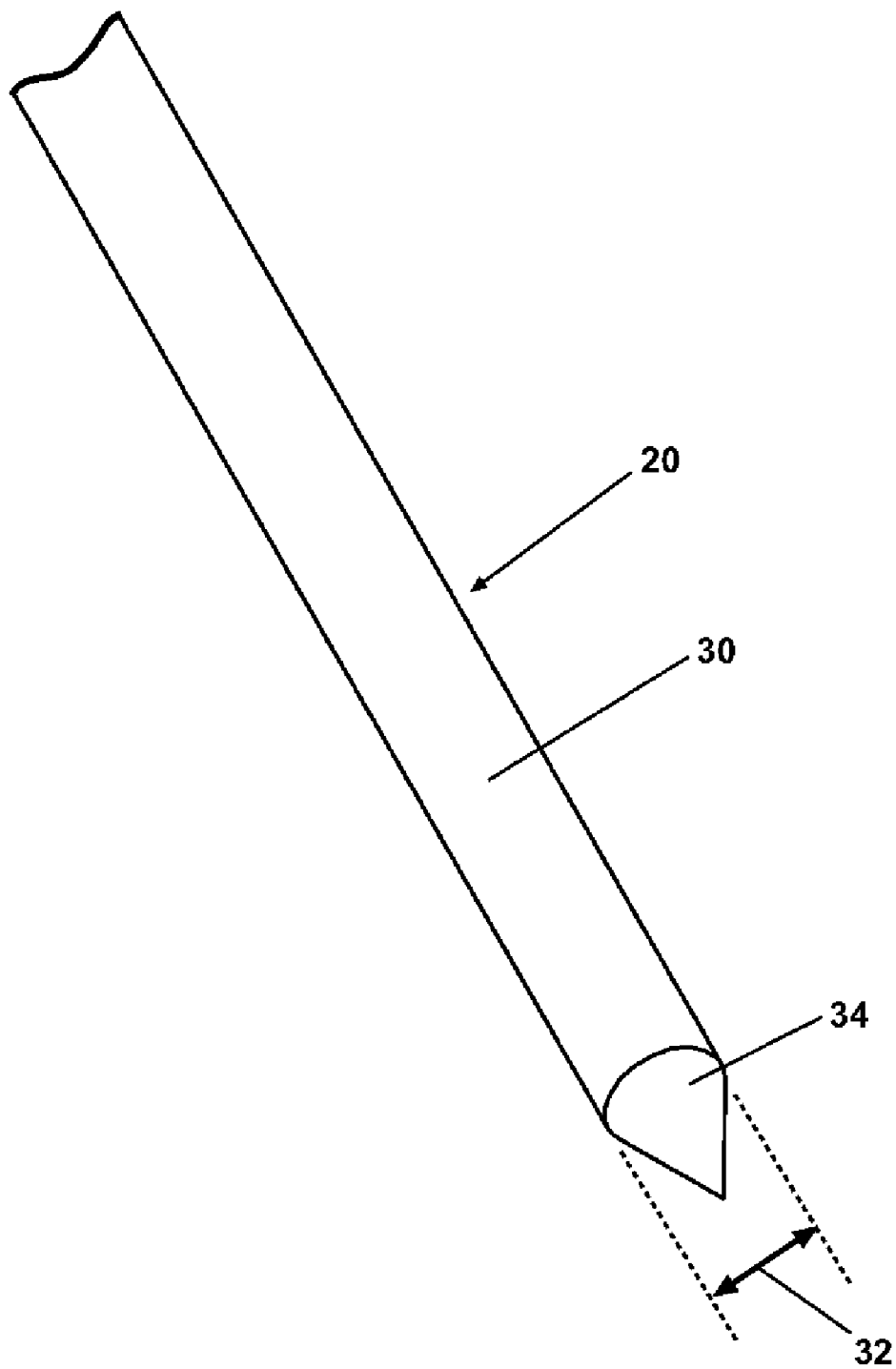
FIG. 4 is an enlarged perspective view of a distal end of the stylet illustrated in FIG. 3.

Referring specifically to FIG. 4, the stylet 20 is an elongated, solid cylindrical member comprising a well-known stylet body 30 terminating in a pointed penetration tip 34. The stylet body 30 has a constant stylet diameter 32 which is sized for slidable and coaxial insertion through the spoon cannula 18.

Figure 5:
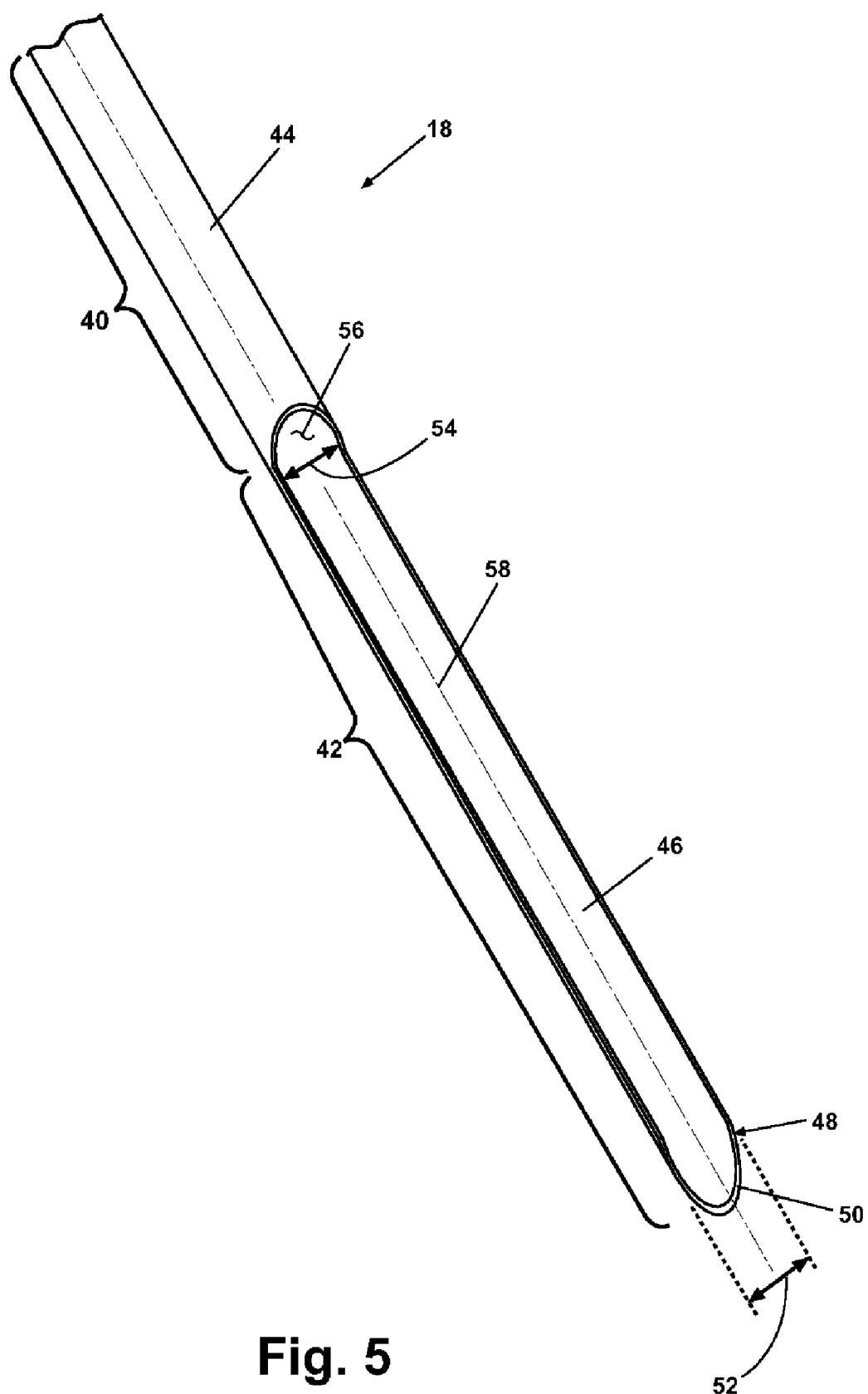
FIG. 5 is an enlarged perspective view of a distal end of the spoon cannula illustrated in FIG. 3.

Referring specifically to FIG. 5, the spoon cannula 18 is an elongated, tubular member having an enclosed section 40 smoothly transitioning distally to a spoon section 42. The enclosed section 40 comprises an annular wall 44 having an outer diameter 52 defining a lumen 56 having an inner diameter 54. The spoon section 42 comprises an arcuate wall 46 contiguous with a portion of the annular wall 44. The arcuate wall 46 is preferably semicircular, defining a central angle of 180°. Alternatively, the arcuate wall 46 can comprise an arc length defining a central angle ranging between about 120° and somewhat greater than 180°. An arc length greater than 180° will provide enhanced support of the biopsy sample and will minimize the risk of unintended sample deformation during removal of the sample from the spoon section 42. The inner diameter 54 is somewhat greater than the stylet diameter 32 so that the stylet 20 is slidably received within the lumen 56.

The arcuate wall 46 terminates at a distal end in an insertion tip 48. The distal edge of the arcuate wall 46 at the insertion tip 48 is inclined relative to a longitudinal axis 58 of the spoon cannula 18 to define a parabolic beveled edge 50. The beveled edge 50 can be provided with a secondary bevel, which in effect sharpens the beveled edge 50, to enhance the penetration capability of the spoon cannula 18 into the tissue mass 22 and the lesion 24.

Figure 6:
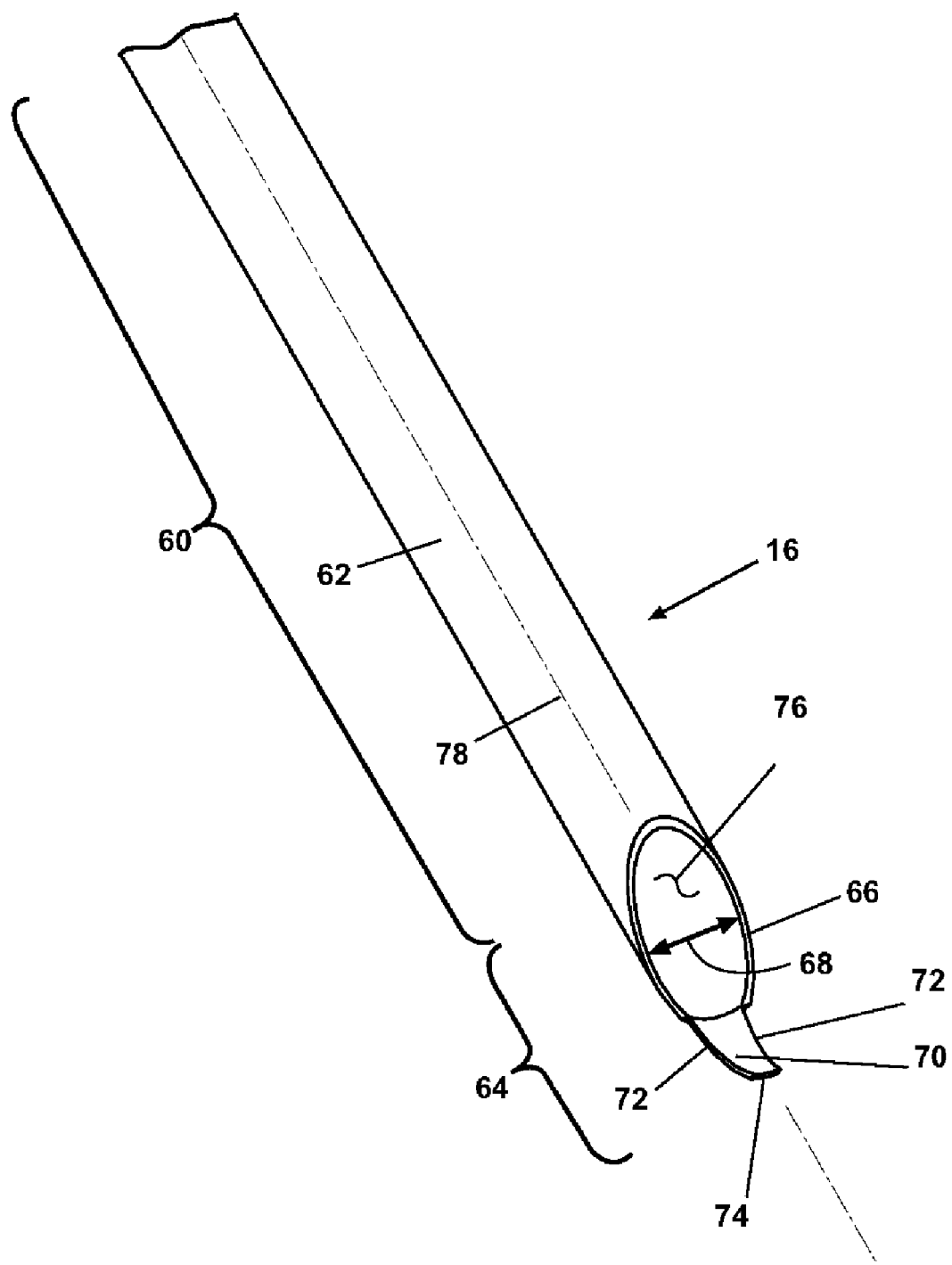
FIG. 6 is an enlarged perspective view of a distal end of the coring cannula illustrated in FIG. 3.

The coring cannula 16, illustrated specifically in FIG. 6, is an elongated, tubular member having an enclosed section 60 comprising an annular wall 62 defining a lumen 76 therethrough having an inner diameter 68. The coring cannula 16 terminates at a distal end in a cutting tip 64. The cutting tip 64 is inclined relative to a longitudinal axis 78 of the coring cannula 16 to define an elliptical beveled edge 66. The beveled edge 66 can be provided with a secondary bevel, which in effect sharpens the beveled edge 66, to enhance the penetration capability of the coring cannula 16 into the tissue mass 22 and the lesion 24.

The inner diameter 68 of the coring cannula 16 is somewhat greater than the outer diameter 52 of the spoon cannula 18 so that the spoon cannula 18 is slidably received within the lumen 76 of the coring cannula 16.

The cutting tip 64 transitions at a distal end to an arcuate excising finger 70 extending generally longitudinally away from the cutting tip 64. The excising finger 70, illustrated in detail in FIG. 7, has a trapezoidal shape comprising a pair of opposed lateral edges 72 terminating in a distal edge 74. Alternatively, the edges 72 can be parallel, providing the excising finger 70 with a rectilinear shape. The edges 72, 74 can be beveled to enhance the penetration and cutting characteristics of the excising finger 70. The excising finger 70 is adapted to have a resilience which enables the excising finger 70 to elastically deflect away from the longitudinal axis 78 and to return to an at-rest arcuate configuration as best seen in FIG. 7.

Figure 7:
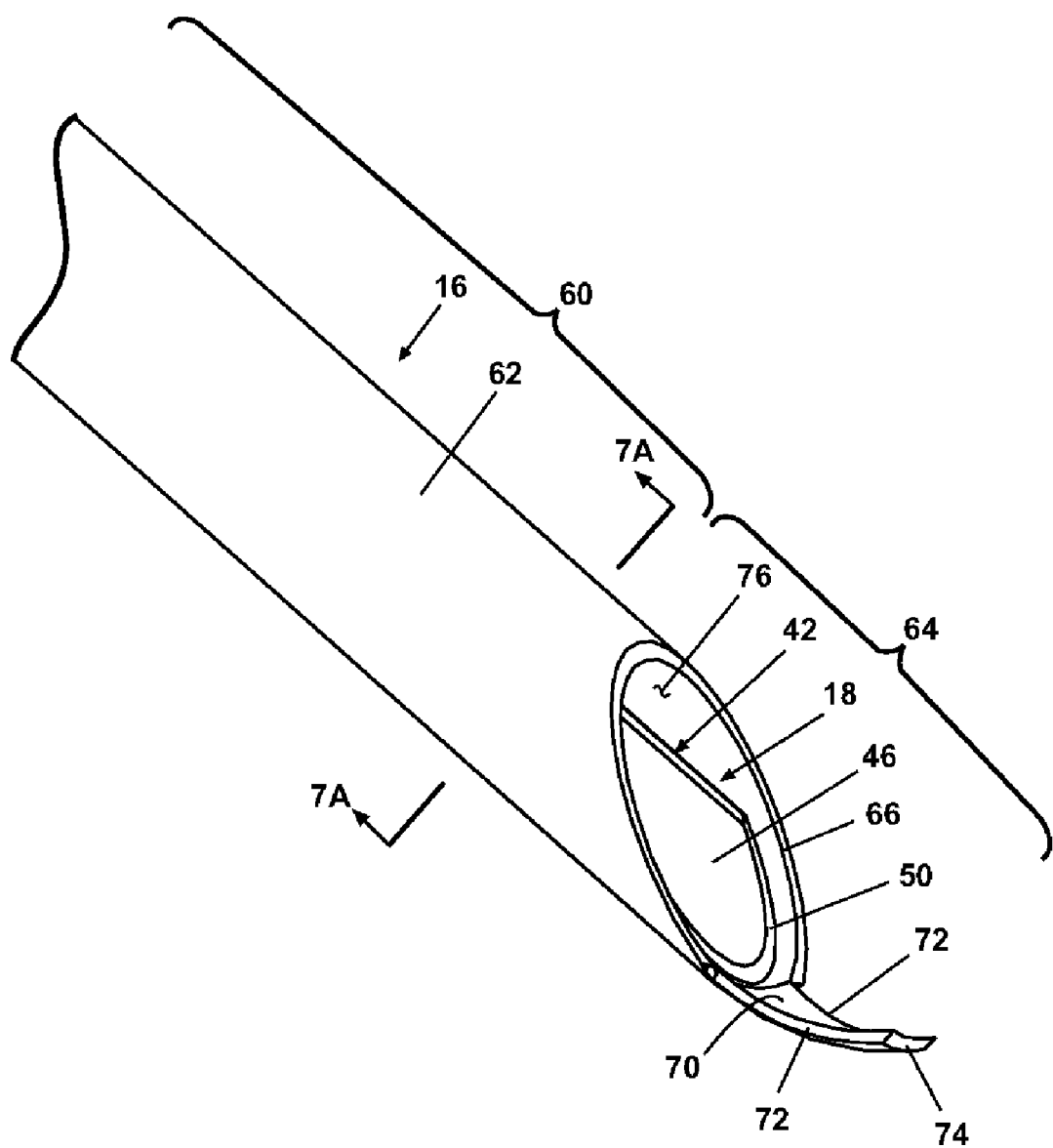
FIG. 7 is an enlarged view of a distal end of the coring cannula and the spoon cannula telescopically received therein, with the coring cannula in the excising position.
Figure 7A:
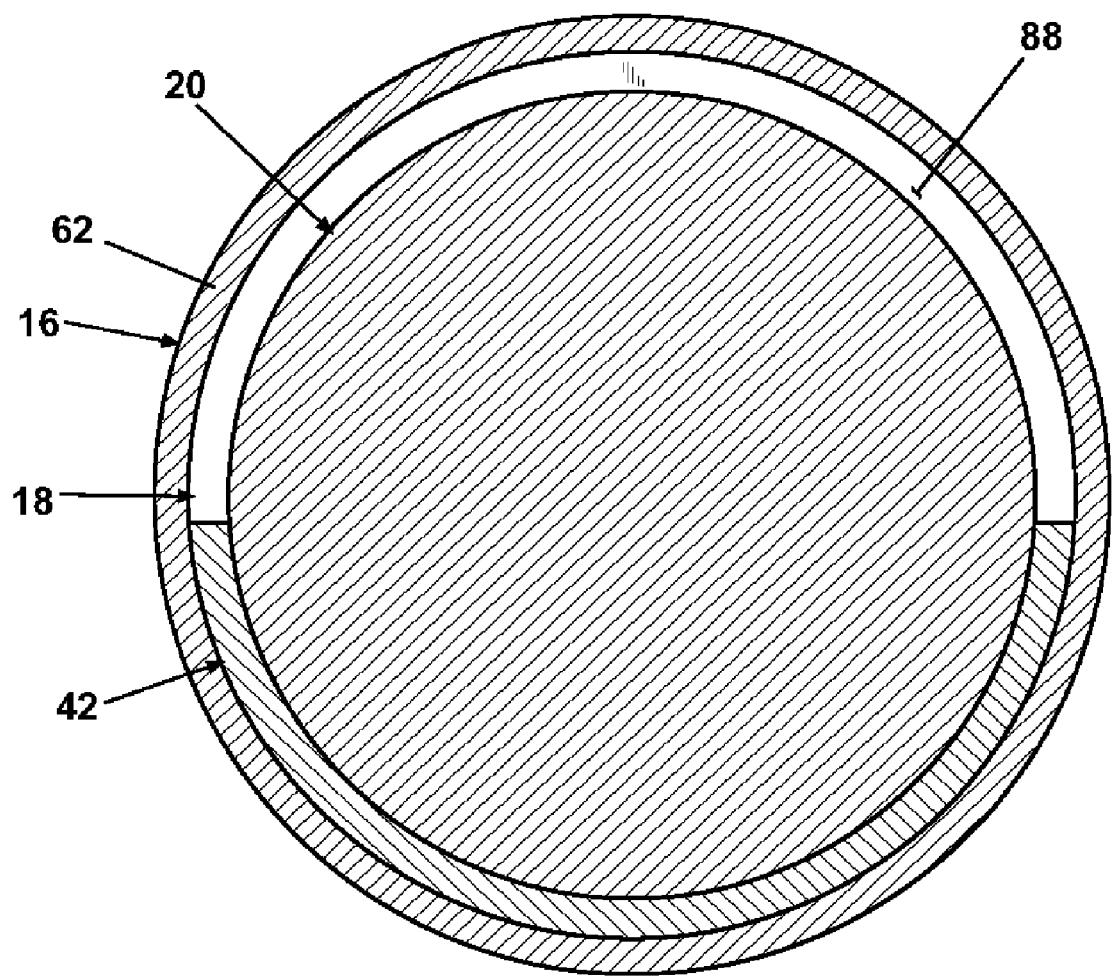
FIG. 7A is a sectional view taken along view line 7A-7A of FIG. 7.

As illustrated in FIG. 7A, the semi-circular configuration of the spoon section 42 results in a semi-annular gap 88 being defined between the stylet 20 and the annular wall 62 of the coring cannula 16 when the coring cannula 16, the spoon cannula 18, and the stylet 20 are in telescoping relationship. This gap 88 extends longitudinally from the insertion tip 48 to the enclosed section 40.

Figure 8A:
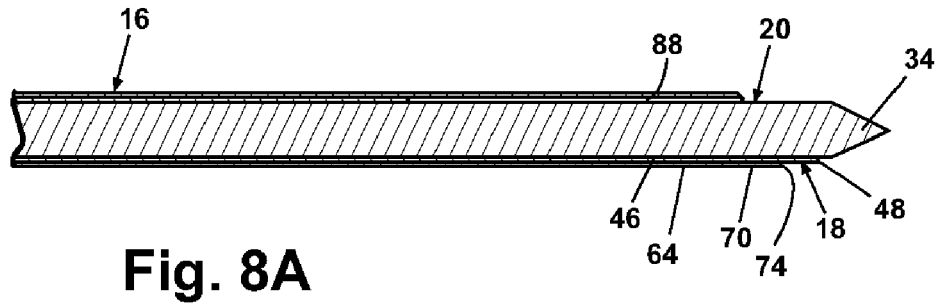
FIG. 8A is a longitudinal sectional view illustrating the cannula assembly in a "cocked" configuration ready for insertion into the tissue mass.
Figure 8B:
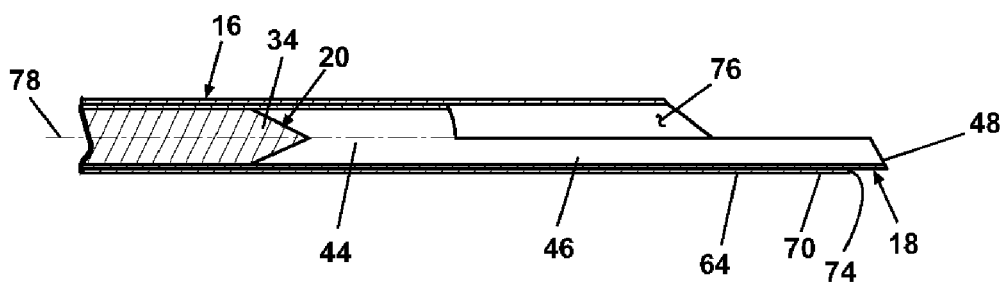
FIG. 8B is a longitudinal sectional view illustrating the cannula assembly in a sampling configuration with the coring cannula and the spoon cannula projected distally over the stylet.
Figure 8C:
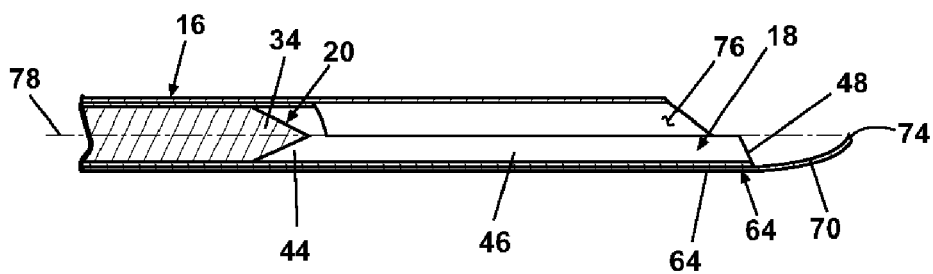
FIG. 8C is a longitudinal sectional view illustrating the cannula assembly in a sample excising configuration with the coring cannula extending distally of the spoon cannula.

As illustrated in FIGS. 6, 7, and 8C, the excising finger 70 is curved inwardly toward the longitudinal axis 78 so that the distal edge 74 extends to, and preferably somewhat beyond, the longitudinal axis 78. The extension of the excising finger 70 at least to the longitudinal axis 78 will enable the excising finger 70 to completely excise a biopsy sample from the lesion 24 when the coring cannula 16 is rotated.

Alternatively, the excising finger 70 can extend just short of the longitudinal axis 78 so that a portion of the biopsy sample remains connected to the lesion 24. In such a configuration, care must be taken to ensure that the suction and/or frictional force acting on the biopsy sample in the core biopsy device 10, along with interference from the excising finger 70 on the sample, will exert sufficient force to retain the biopsy sample in the device 10 and separate the remainder of the biopsy sample from the tissue mass 22 as the device 10 is removed.

Referring to FIGS. 3 and 8A-C, the cannula assembly 14 is assembled by installing the stylet 20 into the lumen 56 of the spoon cannula 18, and installing the spoon cannula 18 into the lumen 76 of the coring cannula 16, to provide a telescoping assembly wherein the coring cannula 16 is slidably and coaxially disposed around the spoon cannula 18, which is slidably and coaxially disposed around the stylet 20. FIGS. 8A-C illustrate the various relative positions of the elements of the cannula assembly when it is moved from the cocked position (FIG. 8A) to an excising position (FIG. 8C).

As illustrated in FIG. 8A, when the cannula assembly 14 is operably attached to the actuator assembly 12 and placed in a cocked configuration, the penetration tip 34 of the stylet 20 extends somewhat distally of the insertion tip 48 of the spoon cannula 18. The insertion tip 48 also extends somewhat distally of the cutting tip 64 of the coring cannula 16 so that the distal edge 74 of the excising finger 70 is in resilient contact with the arcuate wall 46 of the spoon cannula 18, deflected away from the longitudinal axis 78.

FIG. 8B illustrates the cannula assembly in an intermediate position between the cocked and excising positions. To achieve the intermediate position, after the cannula assembly 14 has been inserted into the tissue mass 22 to the lesion 24, the cannulae 16, 18 can be moved relative to the stylet 20 such that the distal ends of the cannulae 16, 18 extend beyond penetration tip 34 of the stylet 20 with the insertion tip 48 of the spoon cannula 18 remaining extended distally of the excising finger 70 of the coring cannula 16. This intermediate position can be either a static or dynamic position. It is preferred that this is a dynamic position that is reached as part of the overall movement from the cocked to the excising position.

As illustrated in FIG. 8C, the coring cannula 16 is projected distally of the spoon cannula 18 so that the excising finger 70 extends distally of the insertion tip 48 to deflect arcuately toward the longitudinal axis 78. This configuration is referred to herein as the excising position. While in the excising position, the rotation of the coring cannula 16 and the excising finger 70 relative to the biopsy sample excises the sample from the tissue mass 22.

Referring again to FIG. 8A, as described above with respect to FIG. 7A, the configuration of the spoon cannula 18 comprising the elimination of a portion of the annular wall 44 to form the spoon section 42 results in the semi-annular gap 88 between the stylet 20 and the annular wall 62 of the coring cannula 16 when the coring cannula 16 is extended over the stylet 20 distally of the annular wall 44. This gap is approximately equal to the thickness of the annular wall 44, or, in a preferred embodiment, approximately 0.004 inch. It is contemplated that this gap is insufficient in size for tissue to be received within the gap during the insertion of the cannula assembly into the tissue mass. However, if tissue were received within the gap, it might negatively impact the performance of the biopsy device 10.

Figure 8D:
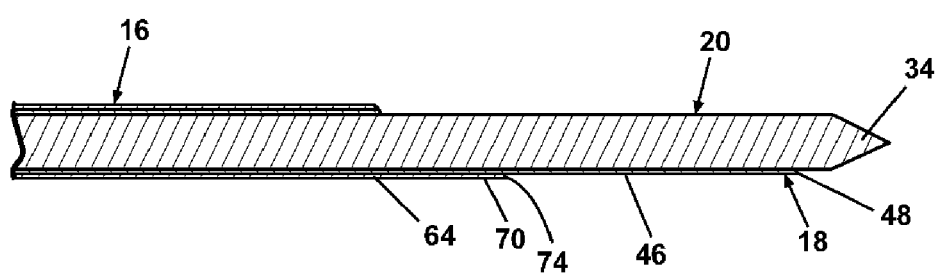
FIG. 8D is a longitudinal sectional view illustrating the cannula assembly in an alternative "cocked" configuration ready for insertion into the tissue mass.

FIG. 8D illustrates an alternate position of the coring cannula 16 in the "cocked" configuration that eliminates the gap during the insertion of the cannula assembly into the tissue mass. As shown in FIG. 8D, the enclosed section 60 of the coring cannula 16 is coextensive with the enclosed section 40 of the spoon cannula 18, but does not extend distally beyond it. This configuration will enable the insertion of the cannula assembly 14 into the tissue mass 22 and the simultaneous advancement of the cannulae 16, 18 over the stylet 20 without the presence of a gap or interference from tissue drawn therein. Thus, the penetration tip 34 of the stylet 20 extends somewhat distally of the insertion tip 48 of the spoon cannula 18, but the insertion tip 48 does not extend distally of the cutting tip 64 of the coring cannula 16, which engages the spoon section 42 somewhat proximally of the insertion tip 48. The cannula assembly 14 is inserted into the tissue mass 22 so that the penetration tip 34 and the insertion tip 48 extend to the lesion 24. It will be recognized that the spoon section 42 will necessarily be of a sufficient strength to enable the spoon section 42 to penetrate the tissue mass 22 without deflection, which would be otherwise controlled by the envelopment of the spoon section 42 by the coring cannula 16.

Figure 9A:
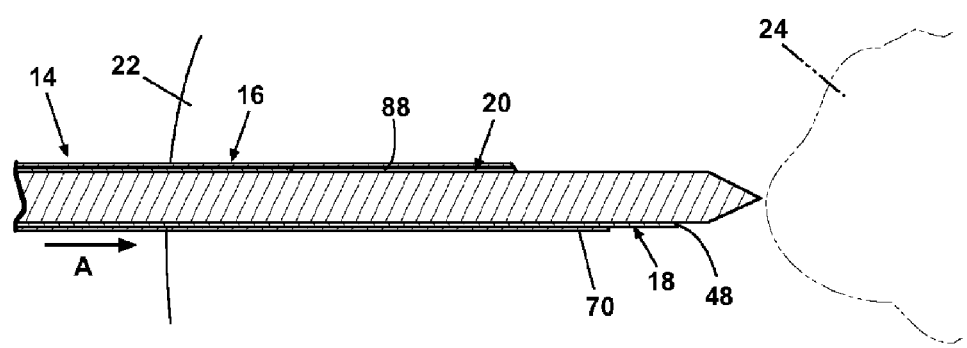
FIGS. 9A-G are longitudinal sectional views of the cannula assembly illustrated in FIG. 2 at various steps in the process of obtaining a core biopsy sample.

The operation of the core biopsy device 10 is illustrated in FIGS. 9A-G in the context of performing a breast biopsy. However, the core biopsy device 10 is not so limited, and can be utilized to obtain a core biopsy sample from other soft tissues, for example the liver, kidney, or skeletal muscles. As illustrated in FIG. 9A, the biopsy procedure is preferably initiated with the cannula assembly 14 in the cocked configuration. In this configuration, the cannula assembly 14 is inserted into the tissue mass 22 by manual or automated means. Preferably, the user grasps the actuator assembly 12 and inserts the cannula assembly 14 into the tissue mass 22 in the direction of arrow "A" using an imaging system to guide the positioning of the cannula assembly 14. Generally, the cannula assembly 14 is positioned within the tissue mass 22 such that, when the sample is taken, at least part of the lesion 24 is included in the sample.

Any suitable imaging system can be used, for example radiography, ultrasound, or MRI. As is well known in the art, the tip of the stylet, cannula, or spoon cannula can be made from material, shaped or provided with markings that enhance the visibility of the elements with a particular imaging system.

The penetration tip 34 of the stylet 20 extends somewhat distally of the insertion tip 48 of the spoon cannula 18 and the insertion tip 48 extends somewhat distally of the excising finger 70 to form a generally solid penetrating tip that facilitates the insertion of the cannula assembly 14 into the tissue mass 22. Portions of the cannula assembly 14 are preferably made such that they are easily viewable and positionable using the selected imaging technique.

Figure 9B:
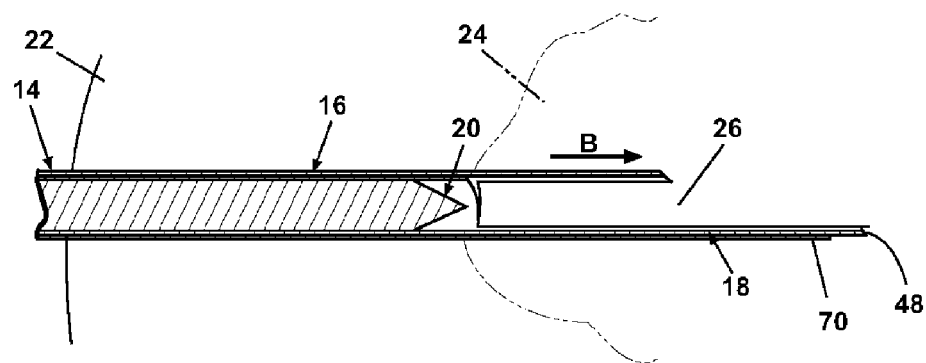

Referring to FIG. 9B, after the initial positioning of the cannula assembly 14, the cannula assembly is moved from the cocked to the excising condition. As part of this movement, the cannula assembly passes through the intermediate position. To affect this movement, the coring cannula 16 and the spoon cannula 18 are advanced relative to the stylet 20, preferably by axially sliding the coring cannula 16 and spoon cannula 18 in the direction of the arrow B along the stylet 20 and into the lesion 24 a distance predetermined by the desired length of the biopsy sample through activation of the actuator assembly 12. In the intermediate position, the excising finger 70 still remains behind the distal end of the spoon and the sample 26 is being cored from the tissue mass 24.

Figure 9C:
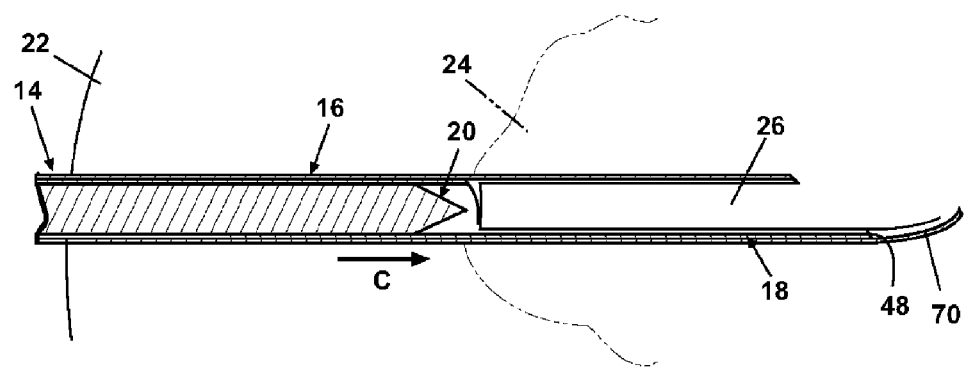

As illustrated in FIG. 9C, after the partial creation of the sample 26 with its end connected to the tissue mass 22, the coring cannula 16 is advanced to the excising position to complete the coring of the sample 26. In the excising position, the excising finger 70 extends beyond the distal end of the spoon and into the end of the sample. This movement is accomplished by moving the coring cannula 16 in the direction of the arrow C. As the excising finger 70 extends beyond the insertion tip 48, the inherent resilience and memory of the excising finger 70 causes it to resiliently return to its at-rest arcuate position, biased in the lesion 24 toward the longitudinal axis 78.

The advancement of the coring cannula 16 to the excising position can be done as part of or separate from the initial advancement of the coring cannula 16 and the spoon cannula 18. Preferably, the advancement of the coring cannula 16 is accomplished in the same step as the advancement of the spoon cannula 18 to form the sample core. To accomplish such a motion, the advancement of the spoon cannula 18 can be stopped prior to the advancement of the coring cannula 16. In other words, the spoon cannula 18 would have a shorter throw distance than the coring cannula 16.

Figure 9D:
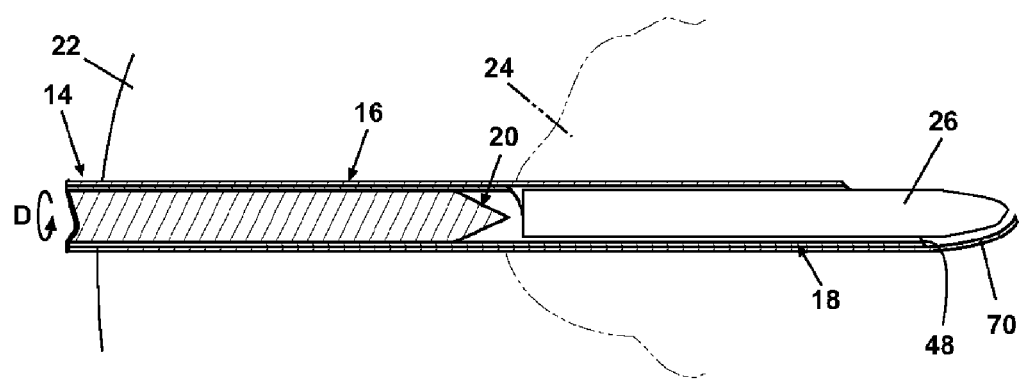
Figure 9F:
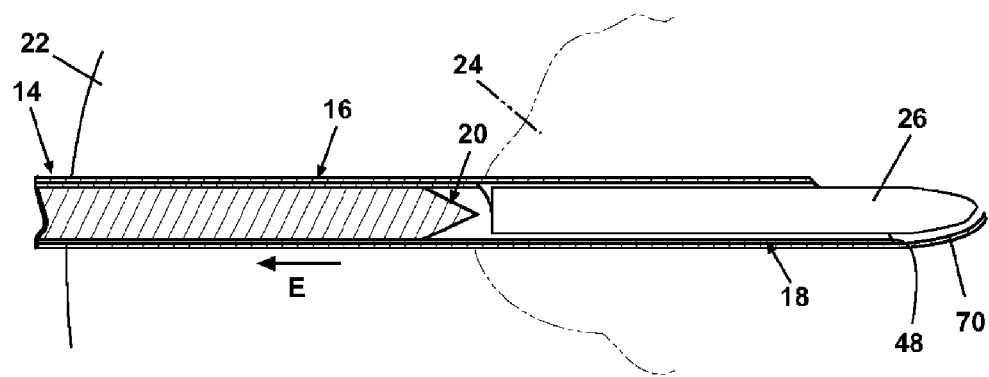
Figure 9G:
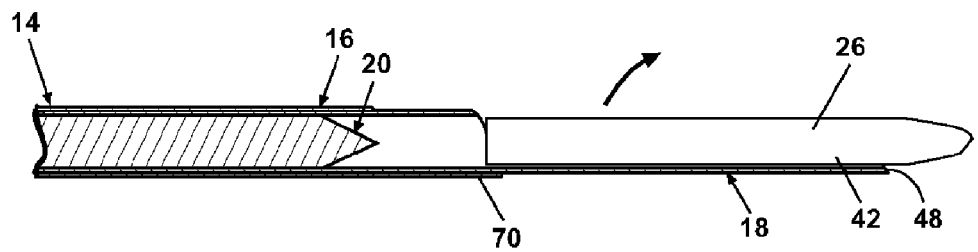
Figure 9E:
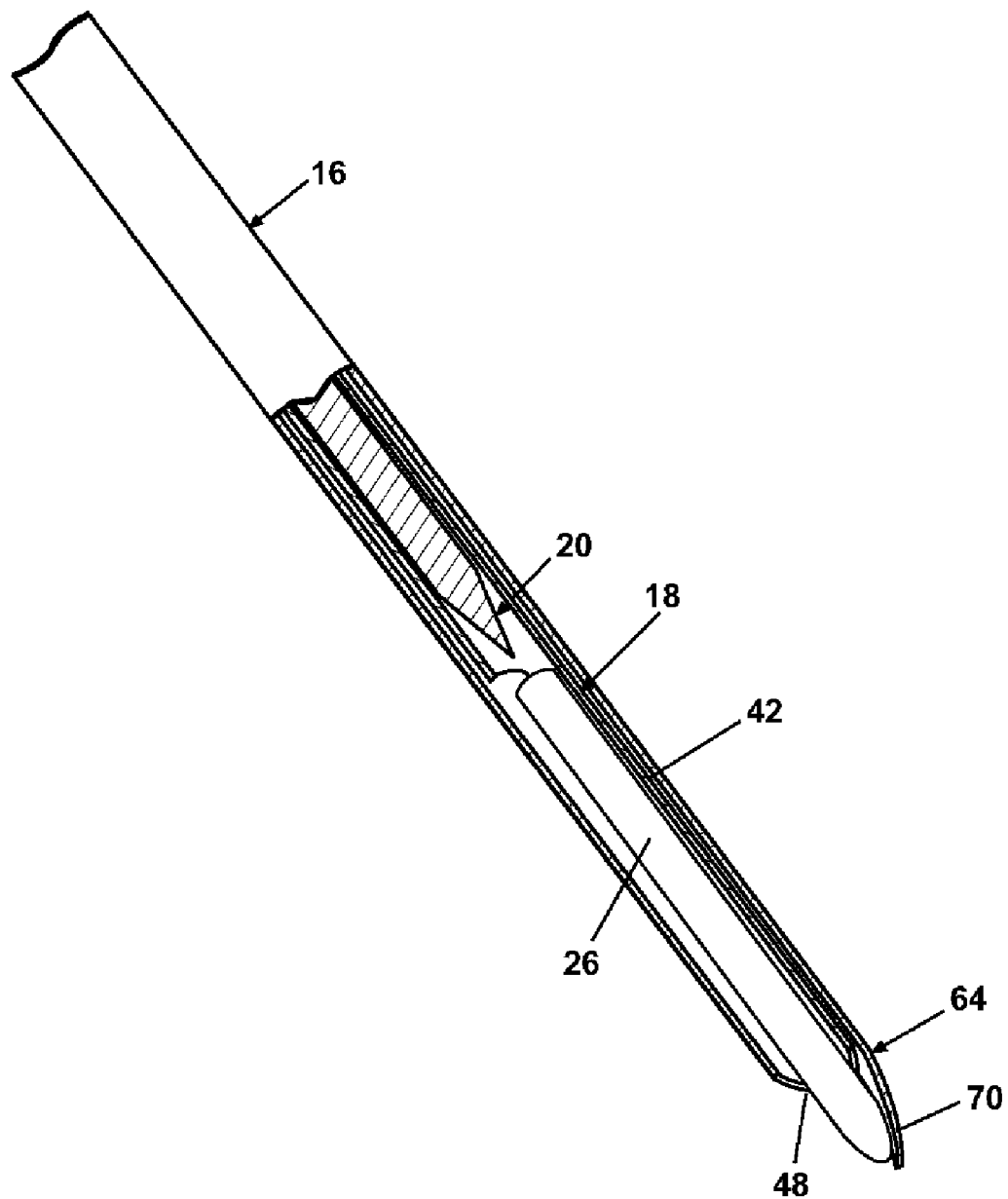

Referring to FIGS. 9D-E, with the coring cannula 16 in the excising position, the sample 26 is severed from the surrounding tissue mass by rotating the coring cannula 16 relative to the spoon cannula 18. As illustrated in FIG. 9D, the coring cannula is rotated in the direction of arrow D. However, either direction of rotation can be used.

The rotation of the excising finger 70 causes the excising finger to sever the end of the sample 26 from the tissue mass to form a somewhat rounded conical surface at the distal end of the biopsy sample 26. The excising finger 70 is preferably rotated approximately 1½ turns to ensure that the biopsy sample 26 has been completely excised from the lesion 24. However, the rotation need only be sufficient to ensure the separation of the sample 26 from the tissue mass 22, which can include a partial revolution or multiple revolutions.

After excising the biopsy sample 26 from the lesion 24, the cylindrical biopsy sample 26 will be supported by the spoon section 42 within the lumen 76, held in place partly by the friction of the cylindrical surface of the sample 26 against the arcuate wall 46 and the annular wall 62, and the radially-inward position of the excising finger 70. With this configuration, the sample 26 is retained within the coring cannula 16 upon removal from the tissue mass 22 by withdrawing the cannula assembly in the direction of arrow E.

Referring to FIG. 9F, after the cannula assembly is withdrawn from the tissue mass, the biopsy sample 26 is removed from the core biopsy device 10 by relatively moving the coring cannula 16 and the spoon cannula 18 such that the spoon section 42 extends beyond the cutting tip 64 of the coring cannula 16. In this position, the sample 26 extends beyond the coring cannula 16 while still being supported by the spoon section 42. The excising finger 70 is also located behind the distal end of the spoon. The practitioner can then lift the sample 26 away from the spoon section 42. This is a great advantage over prior art full core biopsy devices that use the advancement of the stylet to expel the sample. The forced expulsion of the sample can damage the sample and in some cases can render the sample unusable. The biopsy device 10 of the invention can be configured to advance the stylet 20 to expel the sample 26 as do the prior art devices, but for the reasons just stated, it is highly undesirable.

Figure 10:
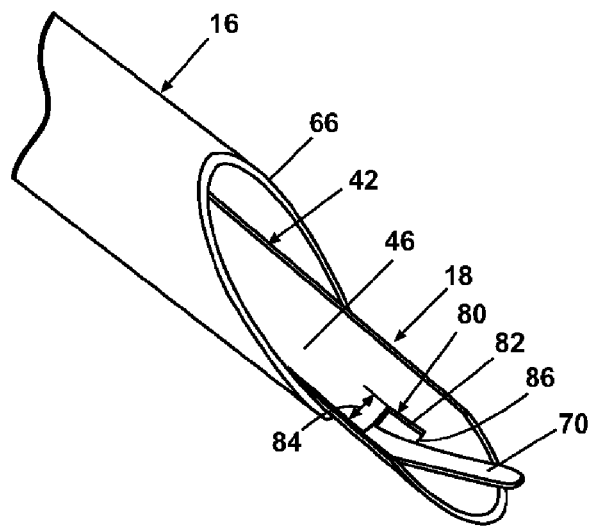
FIG. 10 is an enlarged view of a distal end of a second embodiment of the core biopsy device.

FIG. 10 illustrates a second embodiment of the spoon cannula 18 in which the spoon section 42 is provided with an excising finger window 80 adjacent the insertion tip 48. The excising finger window 80 is a generally rectilinear opening in the arcuate wall 46 comprising a pair of parallel, spaced-apart longitudinal edges 82 defining a window width 84 adapted for slidable insertion of the excising finger 70. The excising finger window 80 has a distal edge 86 adjacent the insertion tip 48. The spoon cannula 18 is received as previously described in the lumen 76 for slidable movement of the spoon cannula 18 relative to the coring cannula 16.

The excising finger 70 is adapted for insertion through the excising finger window 80 so that the excising finger 70 bears against the distal edge 86. As the spoon cannula 18 is drawn into the coring cannula 16, the distal edge 86 bearing against the excising finger 70 will urge the excising finger 70 radially inwardly toward the longitudinal axis 76. Conversely, as the spoon cannula 18 is moved distally along the lumen 76, the finger 70 will resiliently return to its at-rest position. Because the distal edge 86 deflects the excising finger 70, the curvature of the excising finger 70 in its at-rest position can be much shallower, even approaching a straight line, thereby facilitating penetration of the excising finger 70 into the tissue 22 and the lesion 24. With a shallower curvature, the excising finger 70 will be less likely to deflect laterally during penetration. The deflection of the excising finger 70 by the movement of the spoon cannula 18 will enable the excising finger 70 to completely excise the biopsy sample with rotation of the coring cannula 16. It will be evident that rotation of both the coring cannula 16 and the spoon cannula 18 will be required for this embodiment, whereas in the first embodiment only the coring cannula 16 must be rotated.

Figure 11:
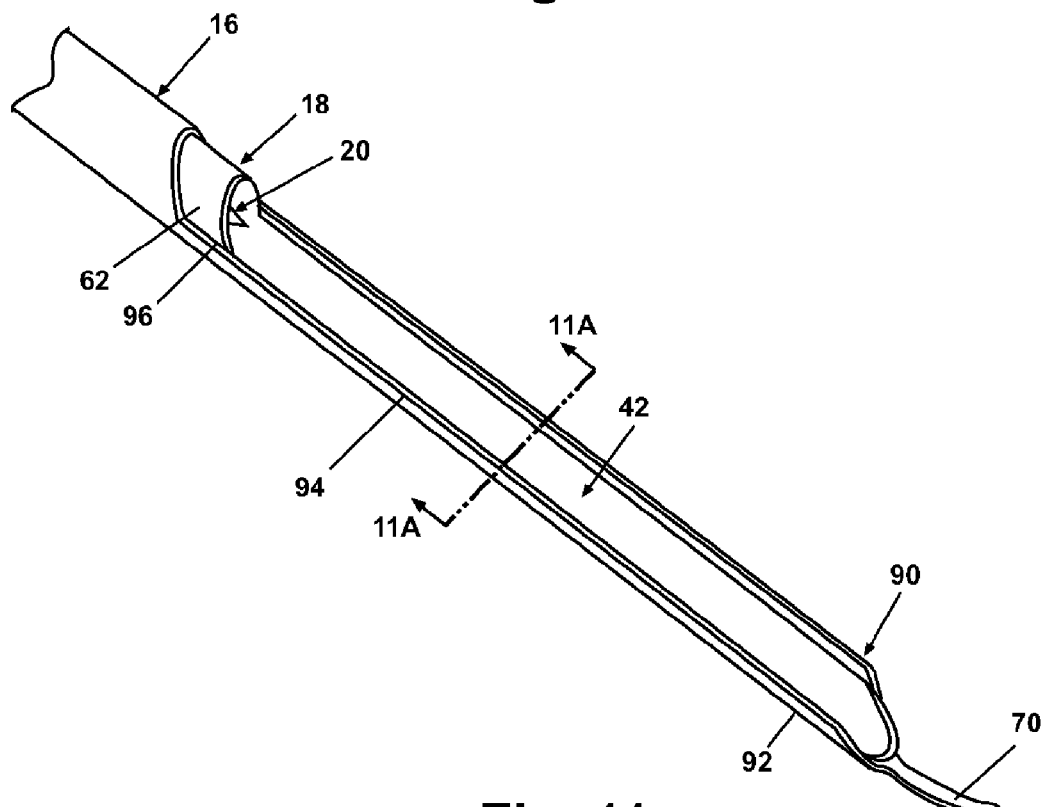
FIG. 11 is an enlarged view of a distal end of a third embodiment of the core biopsy device illustrating the spoon cannula and a coring cannula having a spoon section.

FIG. 11 illustrates a second embodiment of the coring cannula 16 in which the coring cannula 16 is provided with a spoon section 90 similar to the spoon section 42 of the spoon cannula 18. The spoon section 90 comprises an arcuate wall 92 smoothly transitioning distally from the annular wall 62 and cooperatively disposed relative to the arcuate wall 46. The arcuate wall 92 terminates in a pair of parallel, longitudinal, juxtaposed edges 94 extending from the annular wall 62 to the cutting tip 64. The edges 94 are provided with a sharpened bevel 96 adapted for excision of a biopsy sample. After the coring cannula 16 and the spoon cannula 18 have been projected into the lesion 24, as described above, the coring cannula 16 is rotated to excise a biopsy sample from the lesion 24 by the cutting action of the bevel 96 and the excising finger 70. The coring cannula 16 will be rotated so that the annular wall 92 is diametrically disposed relative to the annular wall 44 to form a generally enclosed tubular sample retaining cavity (FIG. 1A).

Figure 12:
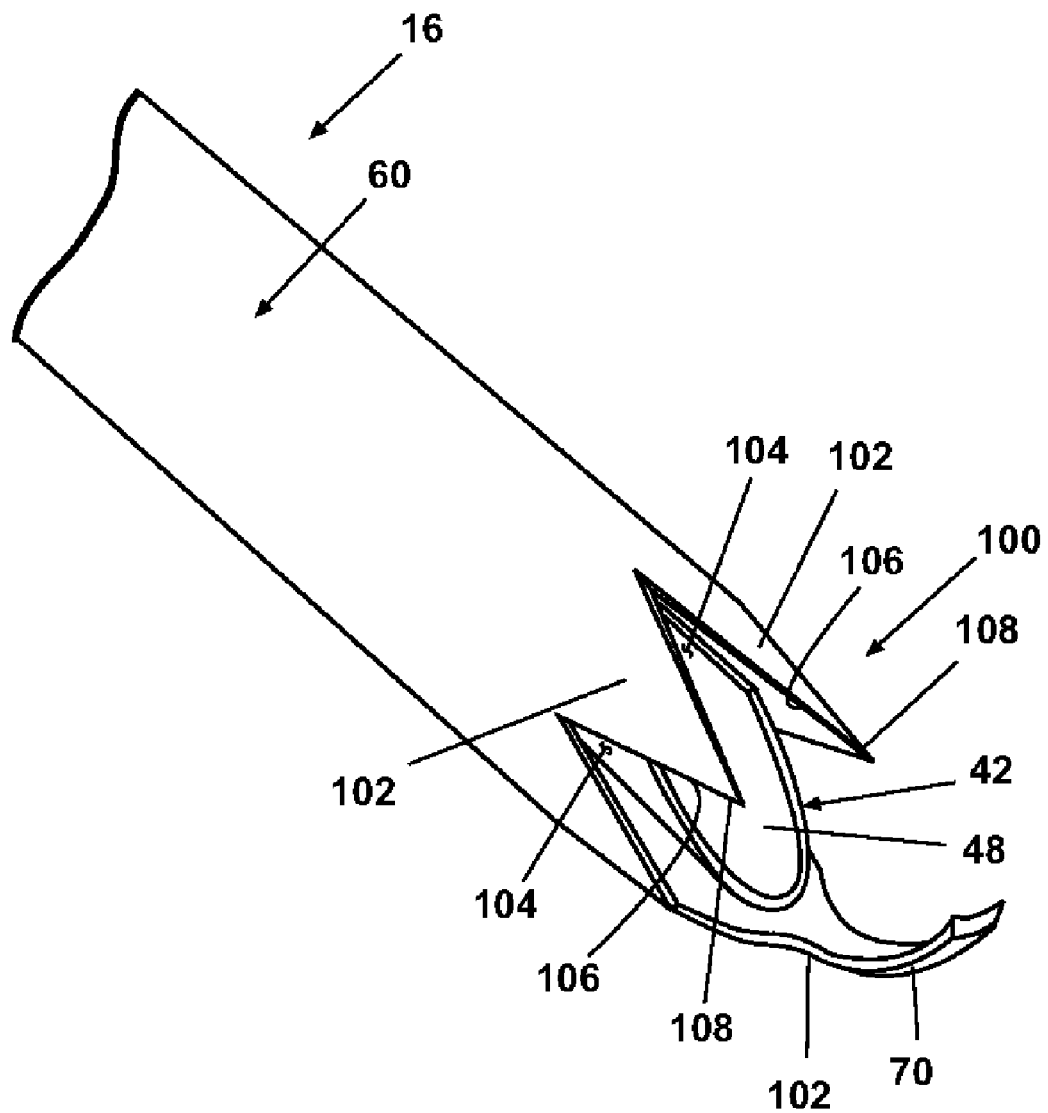
FIG. 12 is an enlarged view of a distal end of a fourth embodiment of the core biopsy device.
Figure 12A:
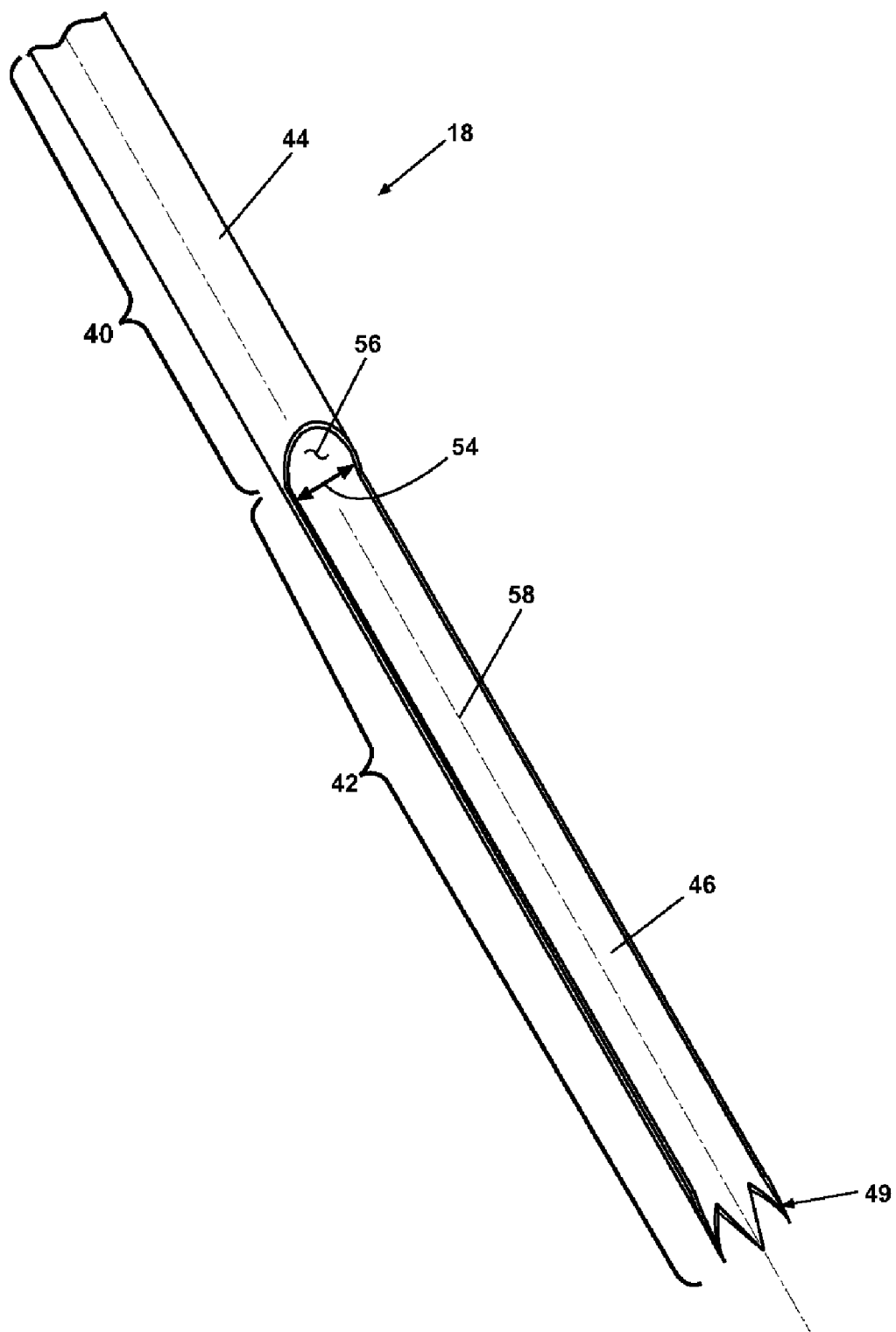
FIG. 12A is an enlarged perspective view of a distal end of the spoon cannula illustrated in FIG. 5 having a scalloped excising tip.

FIG. 12 illustrates an embodiment of the coring cannula 16 in which the cutting tip 64 is provided with a scalloped edge 200 to facilitate penetration of the cutting tip into the tissue 22 and the lesion 24. The scalloped edge 200 defines a plurality of teeth 202 separated by a plurality of valleys 204. The teeth 202 and the valleys 204 can be provided with a sharpened beveled tooth edge 206 for incising into the lesion 24. Each tooth 202 terminates distally in a crown 208. One of the teeth 202 is extended distally of the crown 208 to smoothly transition into the excising finger 70. The spoon cannula 18 can also be provided with a scalloped edge along the insertion tip 48 (FIG. 12A). The insertion of the cannula assembly 14 and the excision of a biopsy sample 26 are generally as previously described herein.

The core biopsy device 10 can be operated in a "corkscrew" manner by rotating the cutting cannula while it is inserted or retracted to excise a biopsy sample that is incised helically and can be unrolled into a generally flat sample. However, due to the increased complexity in obtaining a satisfactory helical sample, this procedure is not preferred.

The actuator assembly can be of any suitable construction as long as it can longitudinally extend the coring and spoon cannulae 16, 18, simultaneously or sequentially in a controlled manner, to place the coring cannula 16 in the excising position, and then rotate the coring cannula 16 a sufficient amount to ensure the separation of the sample 26 from the tissue mass 22 upon withdrawal of the cannula assembly 14.

FIGS. 13-23 illustrate a first embodiment of an actuator assembly 12 for both translating the cannula assembly 14 to the excising position and then rotating the coring cannula 16. As used herein, the term "distal" or "forward" refers to or in a direction toward that end of the actuator assembly 12 and its component parts that is directed toward the cannula assembly 14. "Proximal" or "rearward" thus refers to or in a direction toward that end of the actuator assembly 12 and its component parts that is directed away from the cannula assembly 14.

Figure 13:
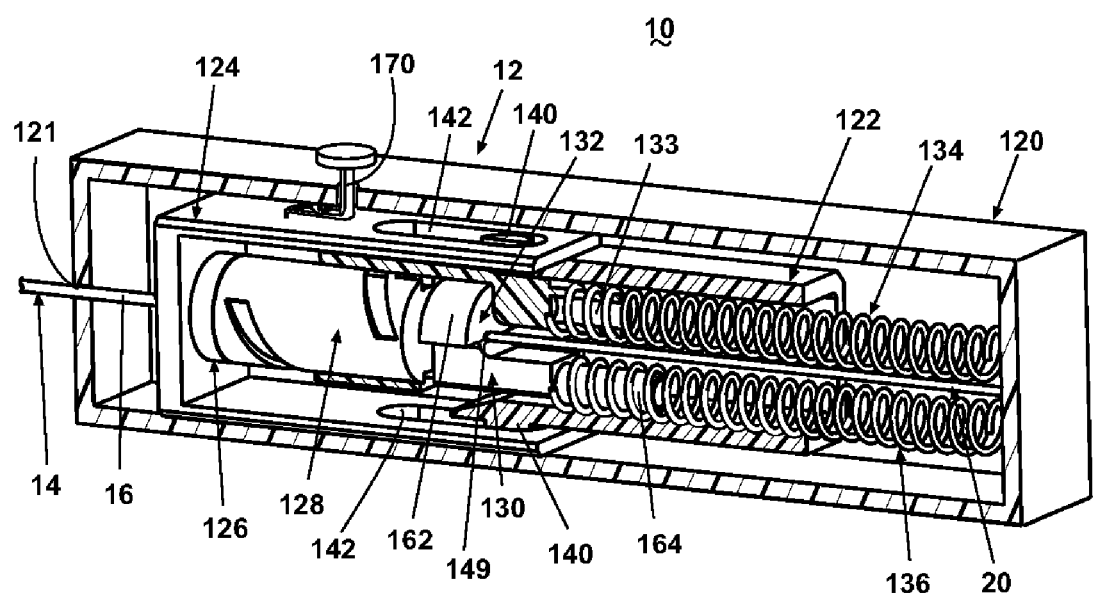
FIG. 13 is a cutaway perspective view of a first embodiment of an actuator assembly for controlling the operation of the cannula assembly for obtaining a core biopsy sample from the lesion, taken along view line 13-13 of FIG. 1.

FIG. 13 illustrates the actuator assembly 12 comprising an actuator enclosure 120 having a portion removed along a longitudinal medial plane for convenience in illustrating and describing the structure and operation of the internal components. The actuator enclosure 120 is illustrated as a generally box-like structure provided with an aperture 121 through which the cannula assembly 14 can slidably extend. The actuator assembly 12 also functions as a handle for the biopsy device 10. Thus, the actuator enclosure 120 can, and preferably will, have a shape which can accommodate the internal components while providing suitable ergonomics for a user to readily and comfortably grip and operate the device. As illustrated in FIGS. 13 and 19-22, the enclosure 120 is provided with a trigger mechanism 170 for initiating the firing and rotation of the cannula assembly 14 into the lesion, and a cocking lever 166 extending through a slot 168 in a wall of the enclosure 120 (FIGS. 19-21) for setting the actuator assembly 12 into the "ready to fire" position, which corresponds to the cocked position for the cannula assembly. The trigger mechanism and cocking lever are illustrated for exemplary purposes only, and other suitable mechanisms for setting and initiating the operation of the actuator assembly can be utilized.

Figure 14:
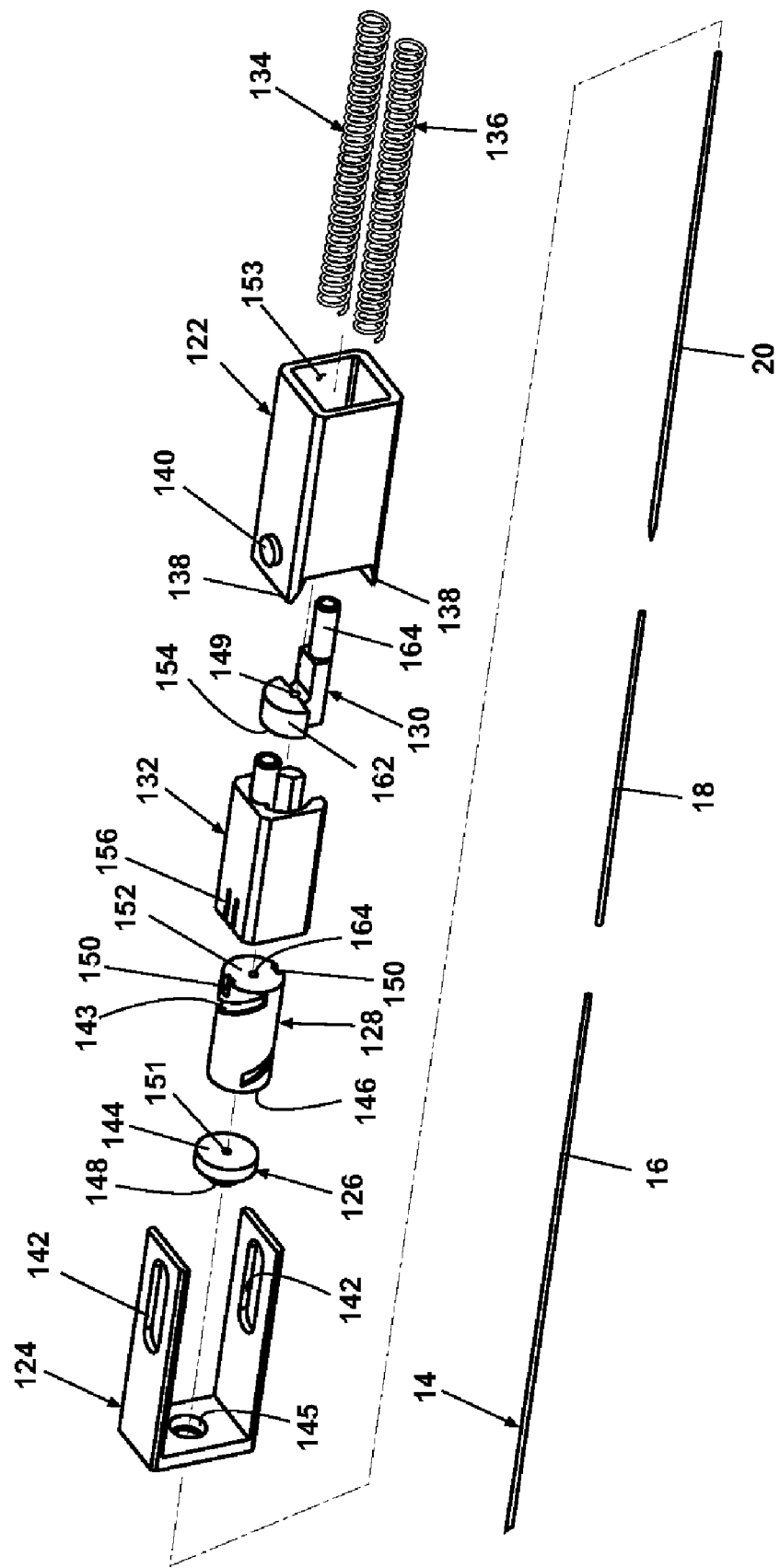
FIG. 14 is an exploded view of the actuator assembly illustrated in FIG. 13.
Figure 15:
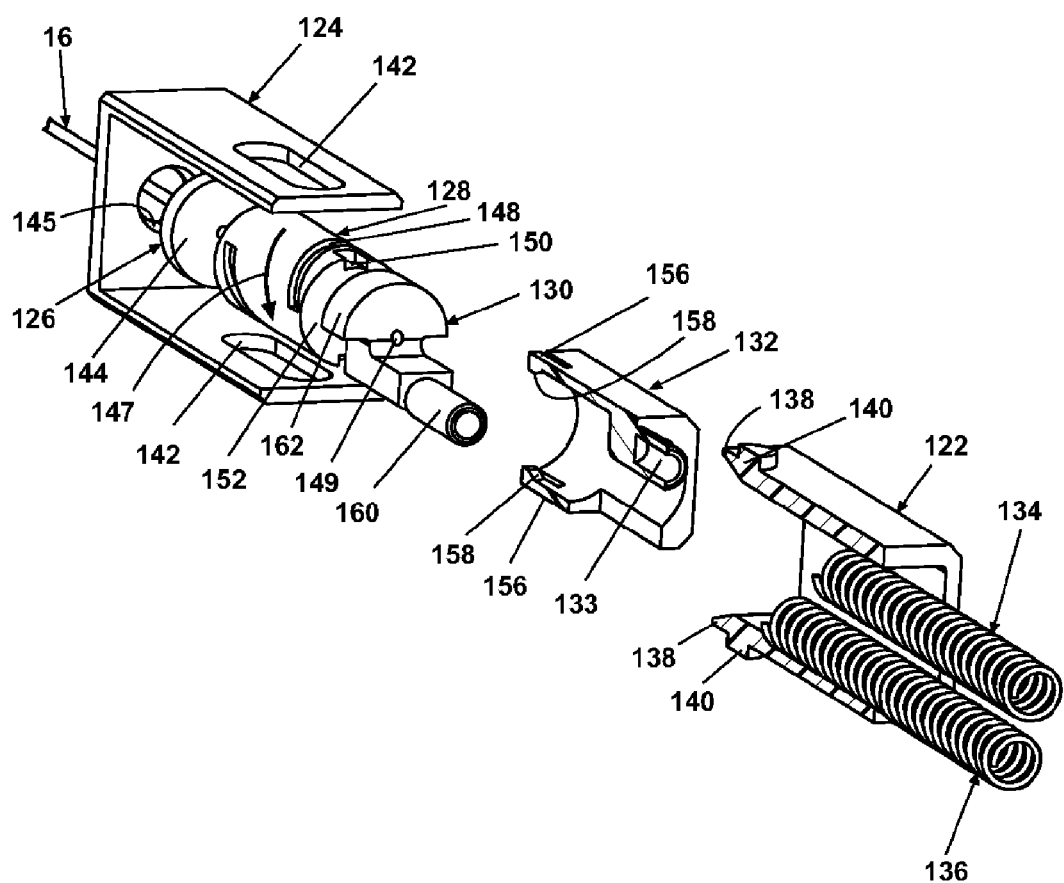
FIG. 15 is an enlarged exploded view of the actuator assembly illustrated in FIG. 14.
Figure 17A:
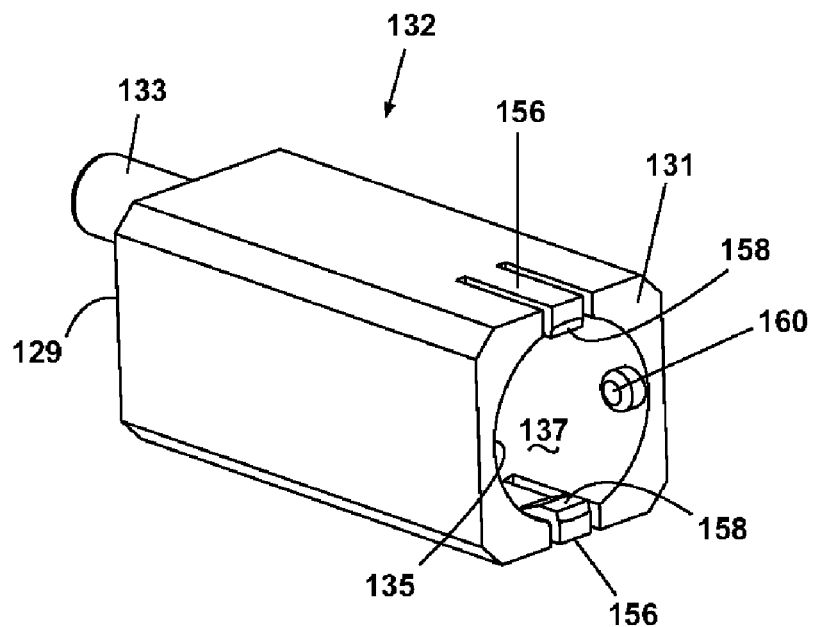
FIGS. 17A-F are alternate views of a driving sleeve comprising a portion of the actuator assembly illustrated in FIG. 13.
Figures 17E, 17F:
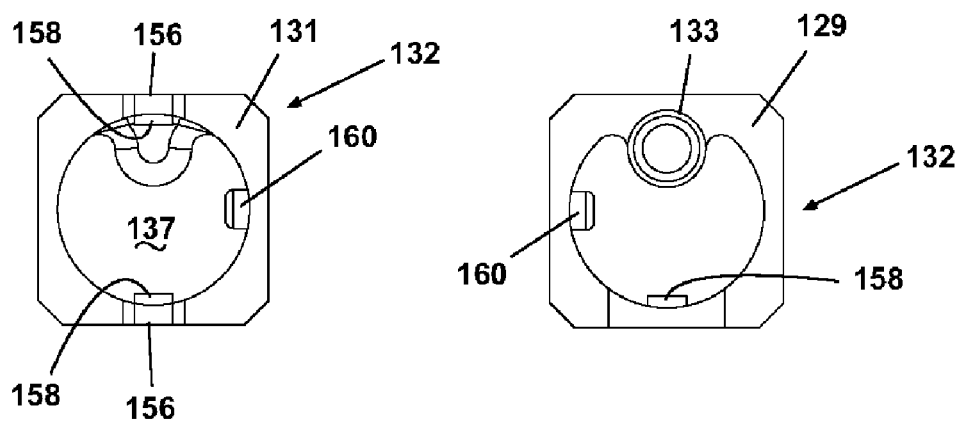
Figure 17B:
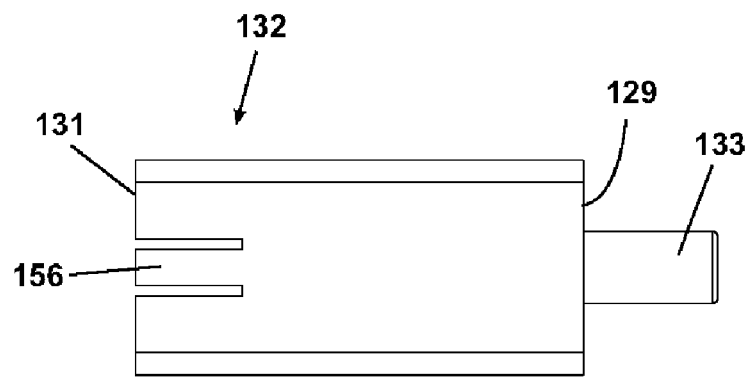
Figure 17C:
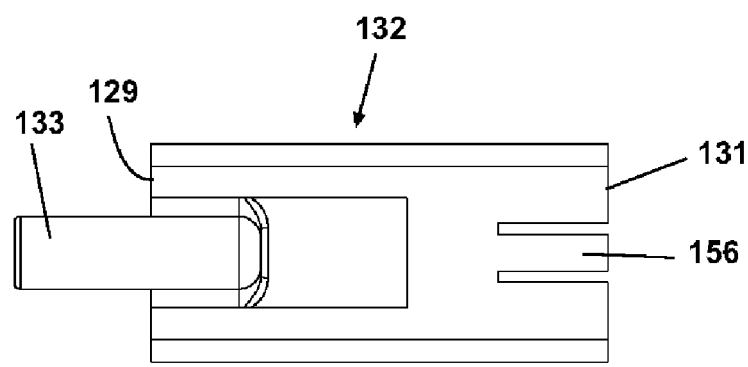
Figure 17D:
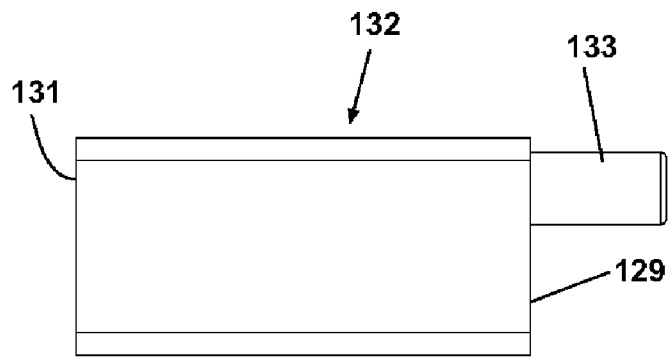

Referring also to FIGS. 14 and 15, the actuator enclosure 120 encloses a retraction body 122 which is fixedly attached thereto. The actuator enclosure 120 also encloses a translating body 124 adapted for linear movement relative to the actuator enclosure 120 and the retraction body 122, a clutch 126, a rotating cylinder 128, a cannula block 130, a driving sleeve 132, a rotation spring 134, and a drive spring 136.

Referring to FIGS. 16A-D, the retraction body 122 is a generally rectilinear, box-like body having a generally square cross-section, an open proximal end 139, and an open distal end 141. The distal end 141 terminates in a pair of opposed, wedge-shaped flanges 138, and a pair of opposed stop bosses 140 extending laterally outwardly therefrom. A rectilinear duct 155 extends longitudinally through the retraction body 122 to define a driving sleeve opening 153.

Referring to FIGS. 14 and 15, the translating body 124 is a rectilinear, generally U-shaped body having a pair of opposed slots 142 at a proximal end thereof. The slots 142 are sized for slidable register with the stop bosses 140. The clutch 126 is a circular, plate-like body having an axial cylindrical stub shaft 143 adapted for fixed reception into a mating circular opening 145 in the translating body 124. The clutch 26 has a clutch face 144 at a proximal end thereof, and is provided with a circular clutch aperture 151 extending axially therethrough and adapted for rotation of the cannula assembly 14 therein.

Figure 18:
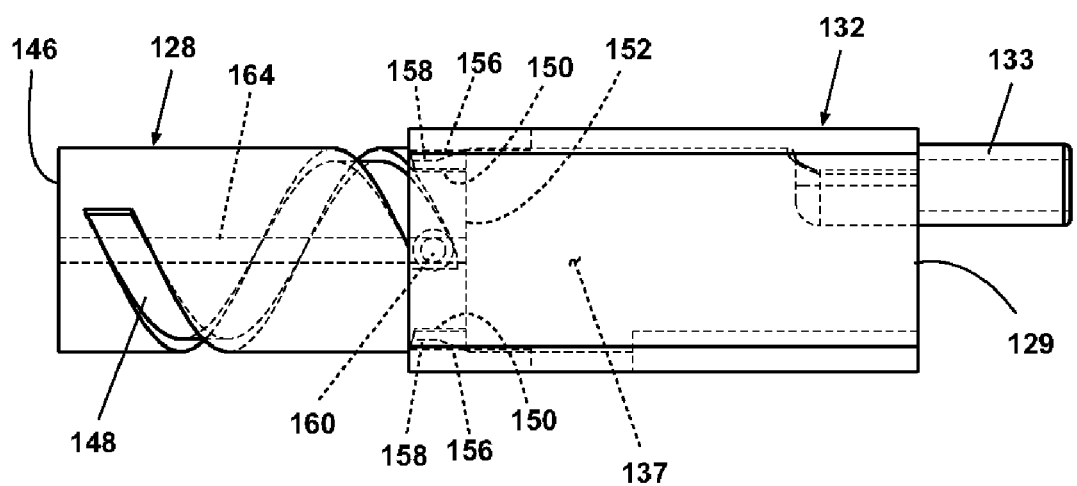
FIG. 18 is an elevation view of the driving sleeve and a rotating cylinder comprising a portion of the actuator assembly of FIG. 13 with portions in phantom to illustrate the operable engagement of the driving sleeve with the rotating cylinder.

Referring to FIGS. 14, 15, and 18, the rotating cylinder 128 is a generally solid cylindrical body comprising a helical slot 148 extending therearound and having a cylinder aperture 164 extending axially therethrough adapted for fixed communication with the coring cannula 16 at a distal end thereof and for rotation of the spoon cannula 18 proximal of the coring cannula 16. The rotating cylinder 128 is provided with a first cylinder face 146 at a distal end thereof adapted for operable register with the clutch face 144, and a second cylinder face 152 at a proximal end thereof. The coring cannula 16 is fixedly received in the cylinder aperture 164. A pair of diametrically opposed detents 150 extend radially inwardly at a proximal end thereof.

Figure 19:
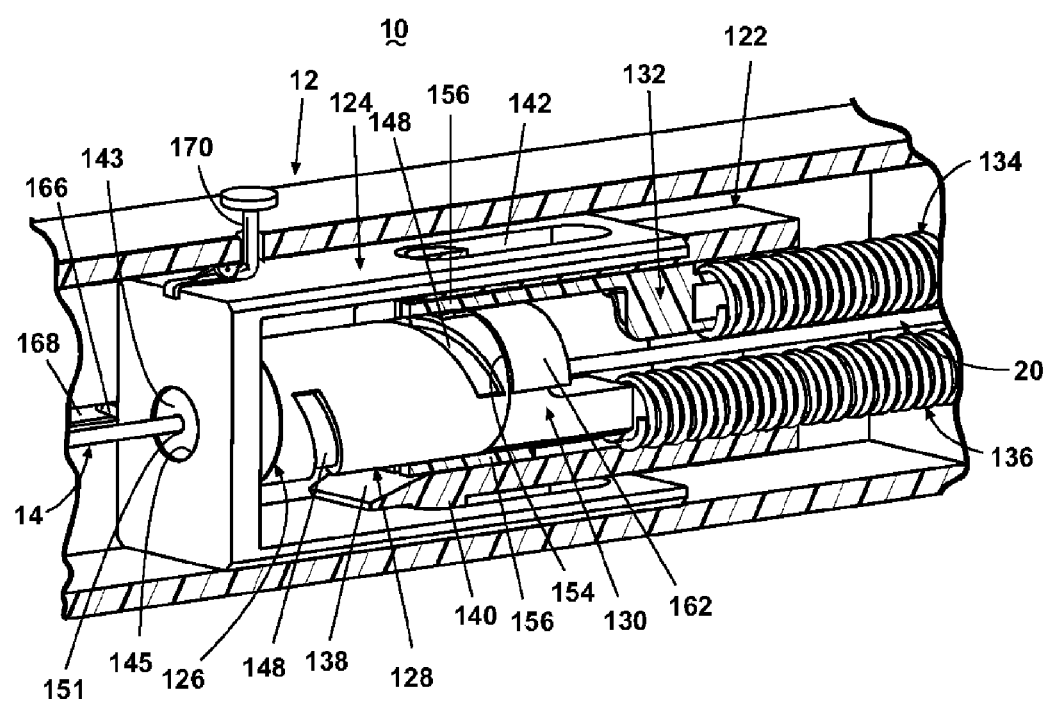
FIG. 19 is an enlarged cutaway perspective view of the actuator assembly illustrated in FIG. 13.

As illustrated in FIGS. 14, 15, and 19, the cannula block 130 is an irregularly shaped body comprising a semi-circular shoe 162 having a cannula block face 154 at a distal end thereof, and a coaxial stylet aperture 149 adapted for coaxial fixed communication with the proximal end of the spoon cannula 18 therein. The spoon cannula is fixedly mounted within the stylet aperture. The cannula block 130 is also adapted with a columnar spring support 164 which is inserted into the drive spring 136 to retain the drive spring 136 in a selected operable configuration.

The stylet 20 extends through the rotating cylinder 128 and the cannula block 130 for fixed engagement with the actuator enclosure 120, such as by seating a proximal end of the stylet 20 into a proximal end wall of the actuator enclosure 120, so that the stylet is fixed against movement relative to the cannulae 16, 18.

As illustrated in FIGS. 14 and 17A-F, the driving sleeve 132 is a generally rectilinear-shaped body having a generally square cross-section, and a circular coaxial bore 135 defining a cylinder passageway 137 therethrough. The driving sleeve 132 has an open proximal end 129, and an open distal end 131, and the cylinder passageway 137 is adapted for partial slidable envelopment of the cannula block 130 and the rotating cylinder 128. The distal end 131 terminates in a pair of opposed cantilevered flexure flanges 156. The flexure flanges 156 are biased to an outward position and comprise a pair of radially inwardly-directed, diametrically-opposed bosses 158 adapted for cooperating register with the detents 150. The driving sleeve 132 is also provided with a radially inwardly-directed rotation pin 160 adapted for cooperating register with the helical slot 148 and preferably spaced 90 degrees from the bosses 158. The driving sleeve 132 is also adapted with a columnar spring support 133 which is inserted into the rotation spring 134 to retain the rotation spring 134 in a selected operable configuration. Both the rotation spring 134 and the drive spring 136 are fixedly attached to the actuator enclosure 120, such as by columnar spring supports (not shown), sockets (not shown), or other suitable means, such as welding or an adhesive.

The cannula block 130 and the driving sleeve 132 are adapted for independent linear translation, but not rotation. The rotating cylinder 128 is also capable of linear translation independent of the cannula block 130, and is adapted for counterclockwise rotation, as illustrated by the rotation vector 147 in FIG. 15. The clutch face 144 and the cylinder face 146 are adapted for cooperating register to enable counterclockwise rotation of the rotating cylinder 128 but prevent clockwise rotation of the rotating cylinder 128, such as by a ratchet-type engagement that allows relative rotation in only one direction.

Referring again to FIGS. 13-15, the clutch 126 is fixedly attached to the translating body 124 by inserting the stub shaft 143 into the opening 145, with the cannula assembly 14 extending coaxially through the clutch aperture 151 for rotation of the cannula assembly 14 relative to the clutch 126. With the coring cannula 16 fixedly received in the cylinder aperture 164 in the rotating cylinder 128, and the spoon cannula 18 extending therethrough and fixedly received into the cannula block 130, the rotating cylinder 128 and coring cannula 16 can rotate about the spoon cannula 18. When the cylinder face 146 is in contact with the clutch face 144, the rotating cylinder 128 can rotate in a counterclockwise direction, but not a clockwise direction.

The driving sleeve 132 slidably envelops the rotating cylinder 128 and the cannula block 130 within the cylinder passageway 137 so that the bosses 158 engage the detents 150 and the rotation pin 160 engages the helical slot 148. The driving sleeve 132 with the rotating cylinder 128 and the cannula block 130 are slidably received in the driving sleeve opening 153 of the retraction body 122. The translating body 124 is slidably attached to the retraction body 122 by insertion of the stop bosses 140 in the slots 142.

The operation of the actuator assembly 12 will now be described. Referring again to FIG. 13 and to FIG. 19, as assembled, the translating body 124 can move linearly relative to the retraction body 122 within limits defined by the engagement of the stop bosses 140 with the slots 142. The rotating cylinder 128 and the coring cannula 16 can translate linearly with and independently of the spoon cannula 18, and can rotate independently of the spoon cannula 18. The rotating cylinder 128 can also translate linearly independently of the cannula block 130. When the driving sleeve 132 is received fully into the retraction body 122, the flexure flanges 156 will be urged inwardly so that the bosses 158 engage the detents 150 to prevent the rotation of the rotating cylinder 128. When the driving sleeve 132 translates distally away from the retraction body 122, the inclined faces of the flanges 138 enable the flexure flanges 156 to flex outwardly due to their resilient outward bias so that the bosses 158 disengage from the detents 150 to enable rotation of the rotating cylinder 128.

Figure 20:
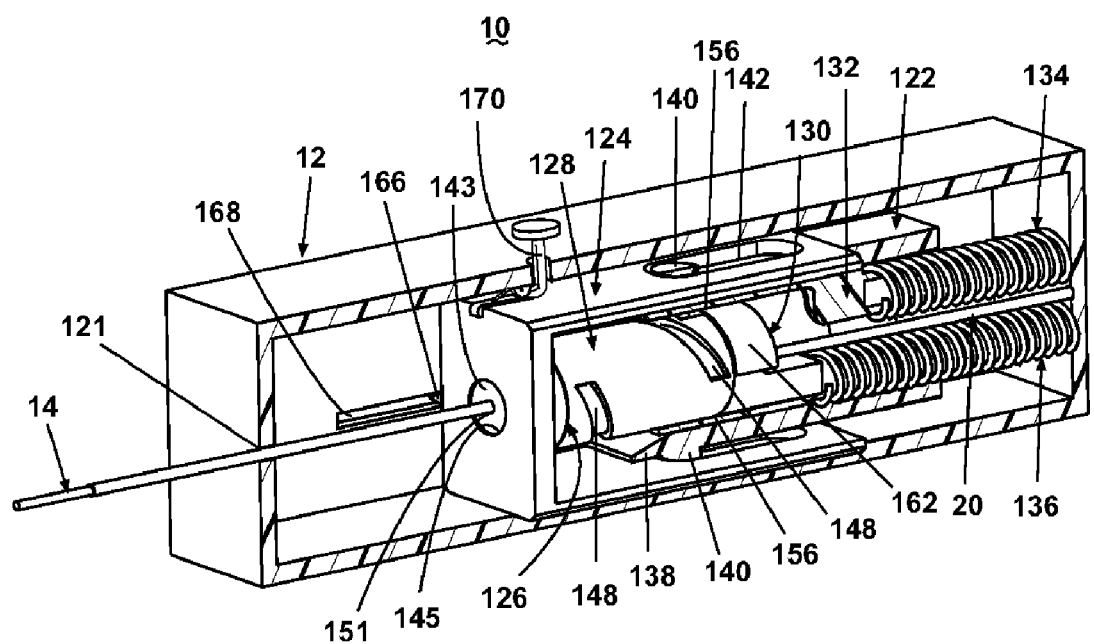
FIG. 20 is a cutaway perspective view of the actuator assembly illustrated in FIG. 13 in a first, cocked position.
Figure 21:
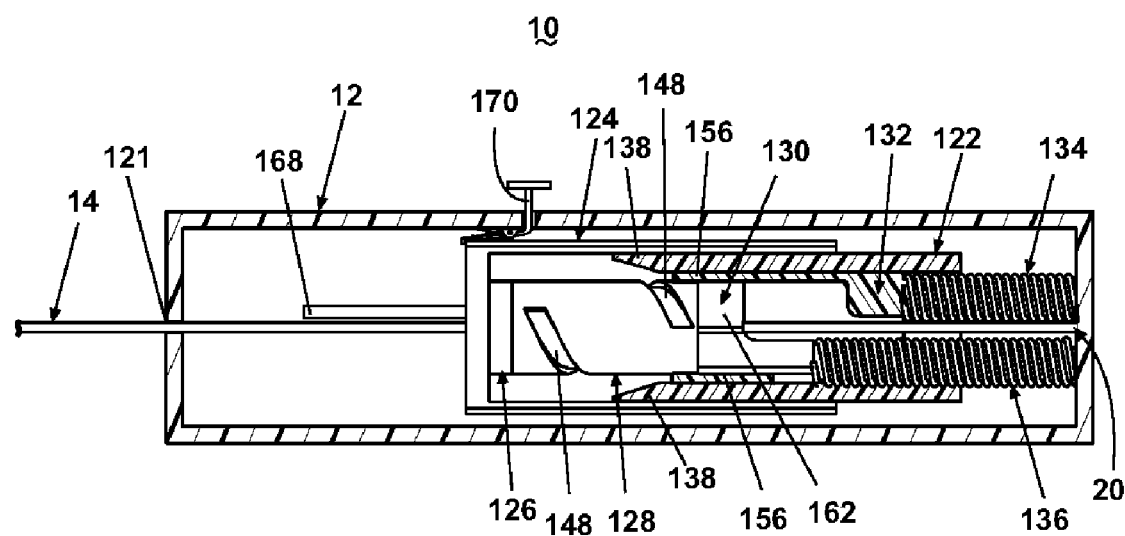
FIG. 21 is a cutaway side elevation view of the actuator assembly illustrated in FIG. 20.

Referring to FIGS. 20 and 21, when the actuator assembly 12 is in a ready position that corresponds to the cocked condition of the cannula assembly, the driving sleeve 132 is fully received in the retraction body 122, which urges the flexure flanges 156 inwardly so that the bosses 158 engage the detents 150, thereby preventing rotation of the rotating cylinder 128. The pin 160 engages the helical slot 148. The cannula block 130 is also received within the retraction body 122 and the springs 134, 136 are compressed. The translating body 124 is held against the spring force of the springs 134, 136 by the trigger 170. The stop bosses 140 engage the distal end of the slots 142 and the rotating cylinder 128 is in contact with both the clutch 126 and the cannula block 130. In this cocked position, as also illustrated in FIG. 8A, the cannulae 16, 18 are retracted proximally so that the penetration tip 34 of the stylet 20 extends somewhat distally of the spoon section 42 of the spoon cannula 18, and the excising finger 70 is in resilient contact with the arcuate wall 46 of the spoon cannula 18 somewhat distally of the insertion tip 48. The enclosed section 60 of the coring cannula 16 extends distally of the enclosed section 48 of the spoon cannula 18 to define the semi-annular gap 88 illustrated in FIG. 7A.

As described previously herein and illustrated in FIG. 9A, with the actuator assembly 12 in the cocked condition, the cannula assembly 14 is inserted into the tissue mass 22 so that the penetration tip 34 is adjacent to the lesion 24. The actuator assembly 12 is then fired by operation of the trigger mechanism 170 for excision of a biopsy sample.

To release the actuator from the ready position to move the cannula assembly from the cocked to the excising position, the trigger 170 is depressed, permitting the translating body to move in response to the spring force. The springs 134, 136 propel the cannula block 130 and the driving sleeve 132 forward, resulting in the corresponding movement of the rotating cylinder 128 forward, which propels the translating body 124 forward. The forward movement of the rotating cylinder 128 and the cannula block 130 advance the coring cannula 16 and the spoon cannula 18, respectively, into the lesion 24 (FIGS. 9B, 22, and 23).

At a point in this movement, the drive spring 136 reaches the limit of its extension, thereby preventing further advancement of the spoon cannula 18. This corresponds to the intermediate position as illustrated in FIG. 9B. During this movement, the rotating cylinder 128 is prevented from rotating by the bosses 158 engaging the detents 150. It is within the scope of the invention to provide a positive stop for the cannula block 130 to stop the advancement of the spoon cannula, instead of relying on the expansion limit of the spring.

The rotation spring 134 continues to propel the driving sleeve 132 forward to move the cannula assembly into the excising position by moving the excising finger 70 until it clears the insertion tip 48 of the spoon cannula 18 (FIG. 9C). During the movement from the intermediate position to the excising position, the flexure flanges 156 clear the flanges 138, and the bosses 158 disengage from the detents 150 (FIG. 23) to permit the rotation of the rotating cylinder as the excising finger reaches the excising position. It is highly preferred that the rotation of the excising finger not begin until the excising finger has reached its longitudinal extent. This prevents the rotation of the excising finger from cutting a helical path in the sample.

Figure 22:
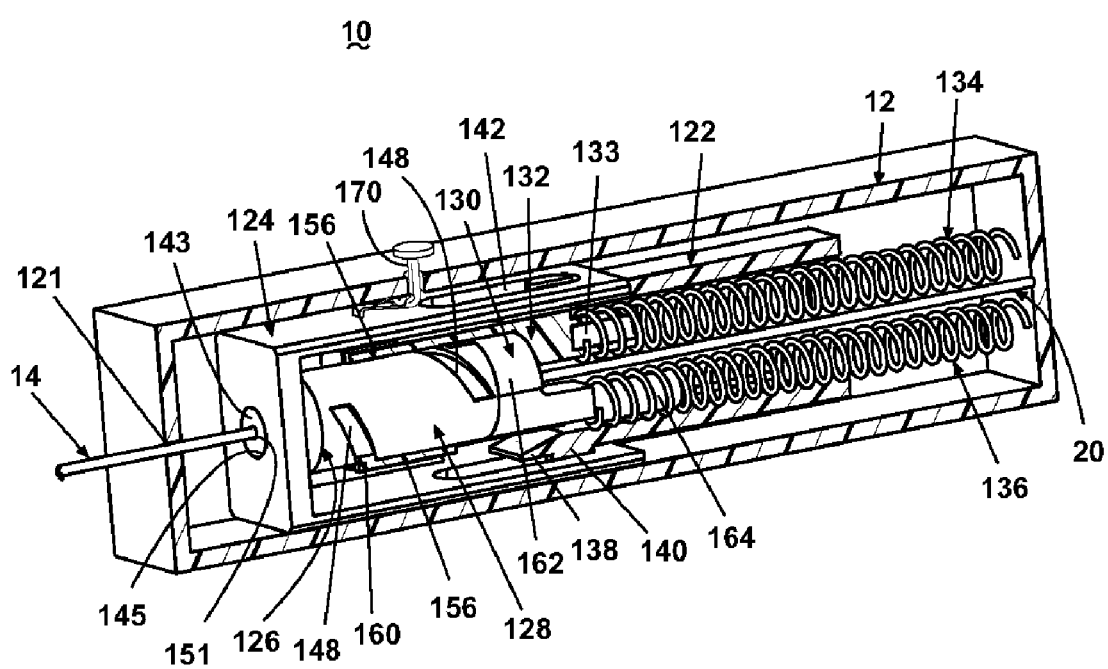
FIG. 22 is a cutaway perspective view of the actuator assembly illustrated in FIG. 13 in a second, fired position.
Figure 23:
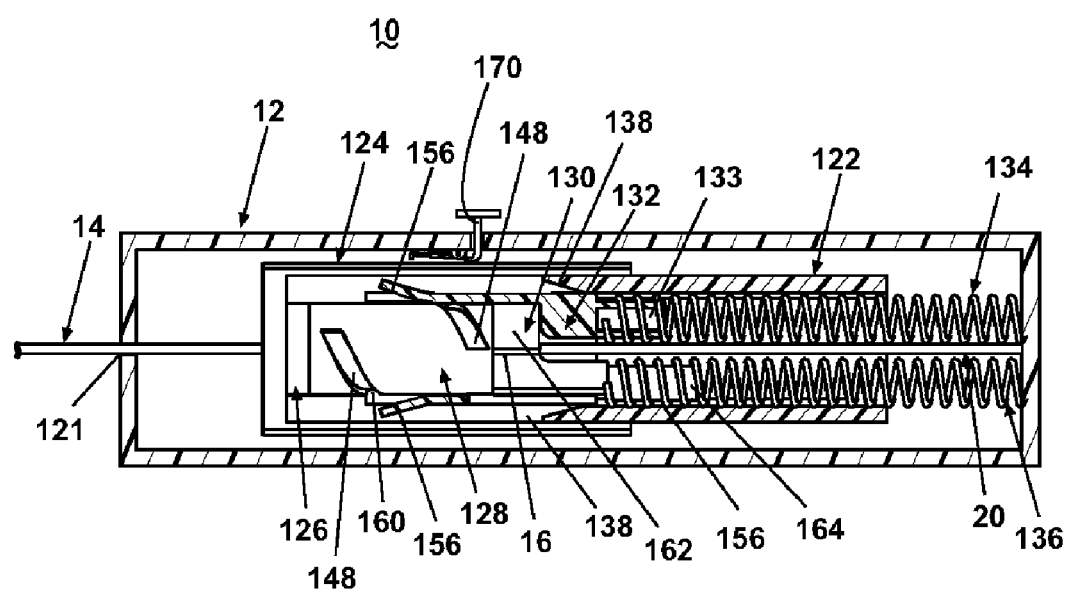
FIG. 23 is a cutaway side elevation view of the actuator assembly illustrated in FIG. 22.

In the excising position, the translating body 124 is prevented from further longitudinal movement by the engagement of the stop bosses 140 with the proximal end of the slots 142 (FIG. 22). Likewise, the rotating cylinder is prevented from further longitudinal movement since it is in contact with the translating body via the clutch 26. However, the driving sleeve 132 can continue to move forward under the influence of the rotation spring 134. Further forward translation of the driving sleeve 132 urges the counterclockwise rotation of the rotating cylinder 128 as the rotation pin 160 travels along the helical slot 148 (FIG. 9D). That is, since the pin 160 is rotationally fixed to the driving sleeve, the forward movement of the driving sleeve causes the helical slot to follow the pin, which necessarily requires the cylinder 128 to rotate in place, without any forward movement. The helical slot 148, the driving sleeve 132, and the rotation pin 160 are preferably adapted so that the rotating cylinder 128 and the coring cannula 16 rotate 1½ turns with a complete stroke of the driving sleeve 132. More than one complete revolution increases the likelihood that the sample is completely severed.

FIGS. 24-49B illustrate a second embodiment of an actuator assembly 220, also referred to as a "biopsy gun," for both translating the cannula assembly 14 to the excising position and then rotating the coring cannula 16. As used herein, the term "distal" or "forward" refers to or in a direction toward that end of the biopsy gun 220 and its component parts that is directed toward the cannula assembly 14. "Proximal" or "rearward" thus refers to or in a direction toward that end of the biopsy gun 220 and its component parts that is directed away from the cannula assembly 14. Additionally, "dorsal" or "upper" refers to or in a direction toward the top of the biopsy gun 220 when oriented as illustrated in FIG. 24, and "ventral" or "lower" refers to or in a direction toward the bottom of the biopsy gun 220 when oriented as illustrated in FIG. 24.

Figure 24:
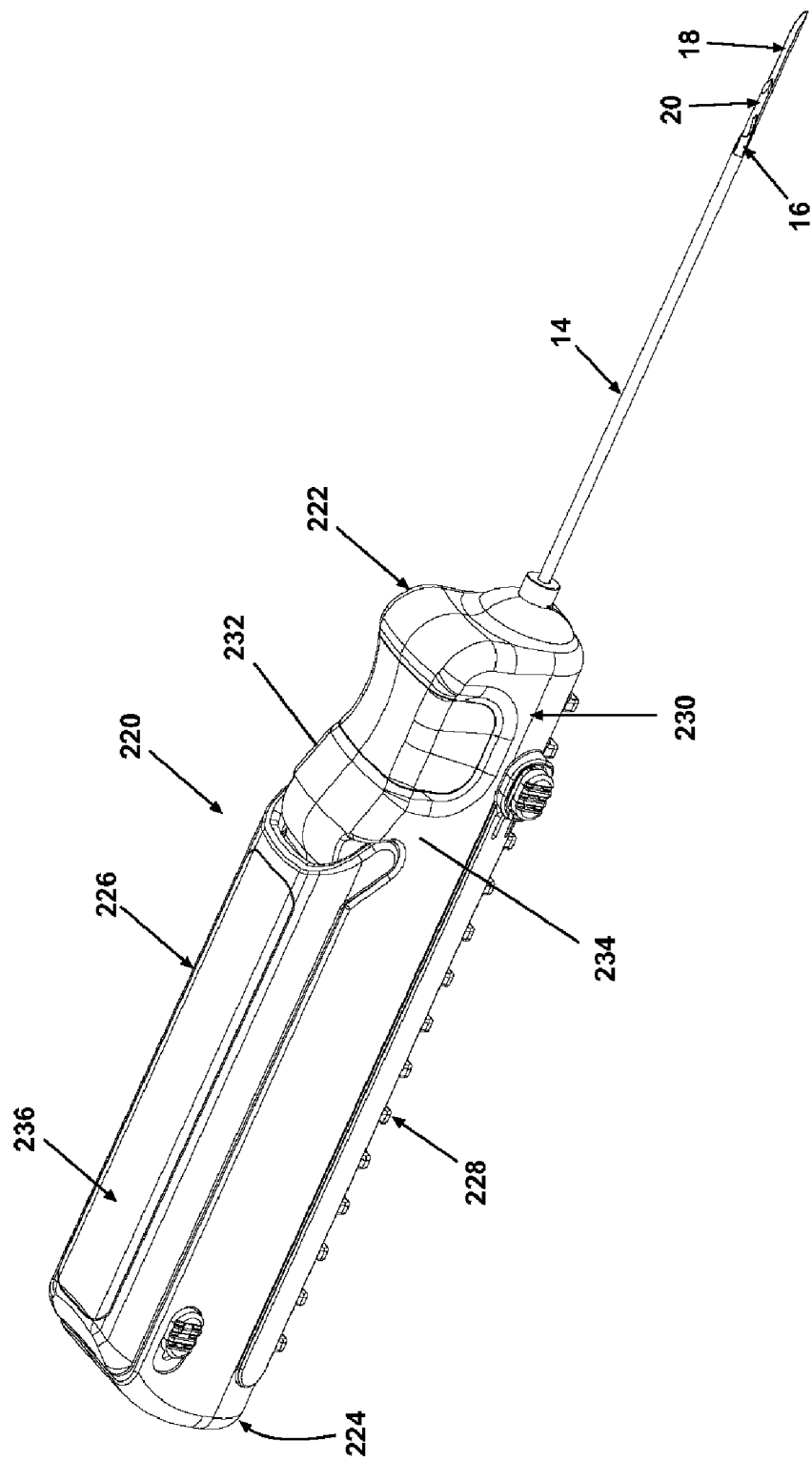
FIG. 24 is a perspective view of a second embodiment of a core biopsy device comprising a second embodiment of an actuator assembly and a cannula assembly according to the invention.
Figure 25:
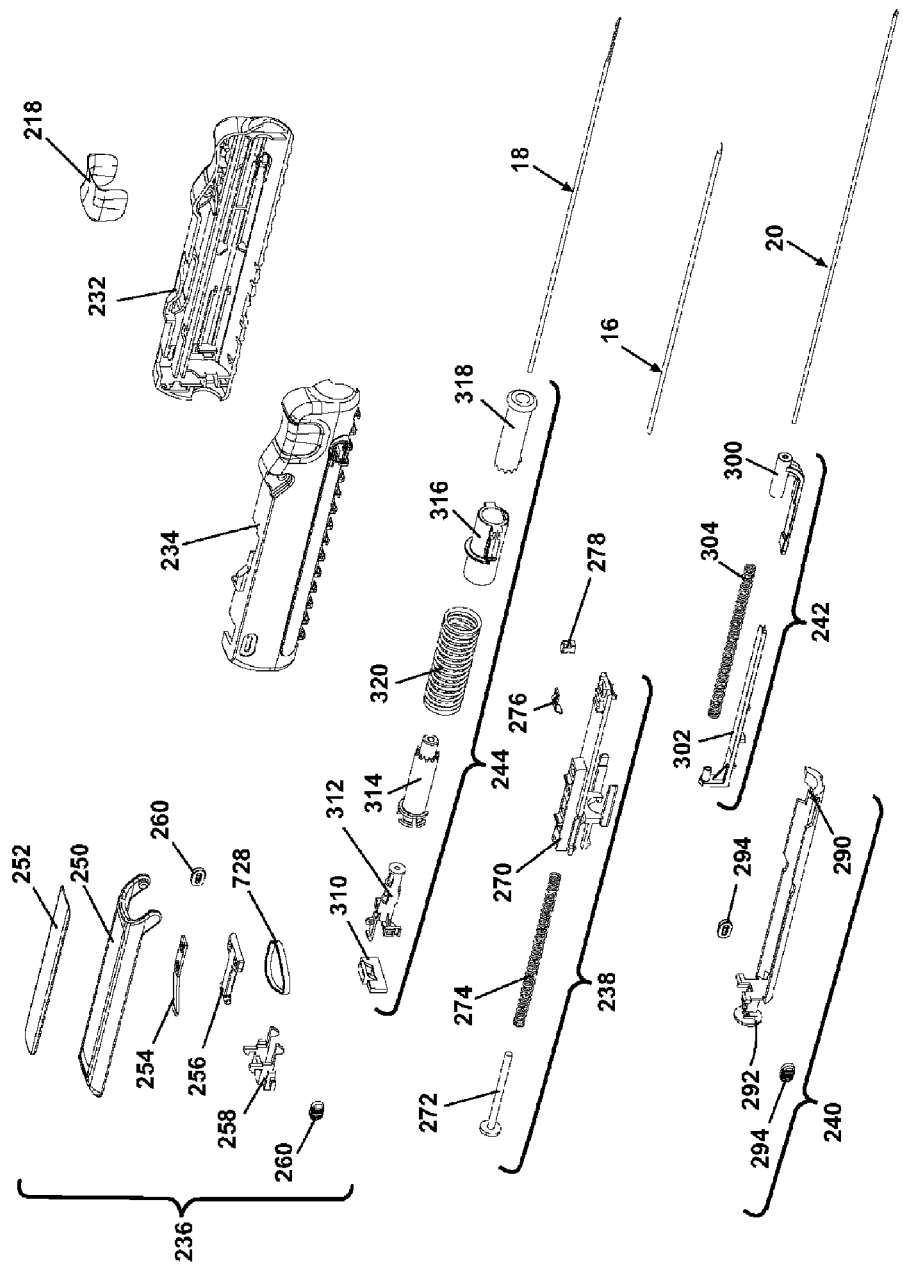
FIG. 25 is an exploded view of the core biopsy device illustrated in FIG. 24, illustrating a cocking handle assembly, a shuttle assembly, a trigger assembly, a sample size control assembly, and a cannula operation assembly.

FIG. 24 illustrates the biopsy gun 220 operably connected to the cannula assembly 14. The biopsy gun 220 has a distal end 222, a proximal end 224, a dorsal side 226 supporting a cocking handle assembly 236, and a ventral side 228. Referring also to FIG. 25, the biopsy gun 220 comprises an outer housing 230 comprising a left housing shell 232 and a right housing shell 234 adapted for cooperative registry, and a housing grip 218, to provide an ergonomic, functional handle for facilitating the insertion of the cannula assembly 14 in a lesion 24 and the recovery of a biopsy sample 26.

The biopsy gun 220 comprises the cocking handle assembly 236, a shuttle assembly 238, a trigger assembly 240, a sample size control assembly 242, and a cannula operation assembly 244. The cocking handle assembly 236 comprises a handle 250, a grip pad 252, a spring 254, a swing arm 256, a latch 258, and a pair of latch buttons 260. The shuttle assembly 238 comprises a shuttle 270, a spring retainer 272, a spring 274, a cam spring 276, and a cam block 278. The trigger assembly 240 comprises a firing cage 290 terminating proximally in a firing plunger 292 and a pair of firing buttons 294. The sample size control assembly 242 comprises a nosepiece 300, an adjustment member 302, and a spring 304. The cannula operation assembly 244 comprises a latch plate 310, a spoon cannula carriage 312, a cutting cannula carriage 314, a helical drive member 316, a rotating driven member 318, and a spring 320. These elements are interconnected and supported within the housing 230 in and on various seats, slots, and rails facilitating the precisely controlled movement of the elements during the sample recovery process.

FIGS. 26A-C and 27 illustrate the right housing shell 234. The housing shell 234 is an irregularly-shaped, elongated body comprising an elongated side wall 330 joined to a top wall 332, a bottom wall 334, a proximal wall 336, and a distal wall 338. The walls 330-338 are contoured, and configured with openings, bosses, rails, and the like, for operational support of the elements comprising the biopsy gun 220.

Figure 26A:
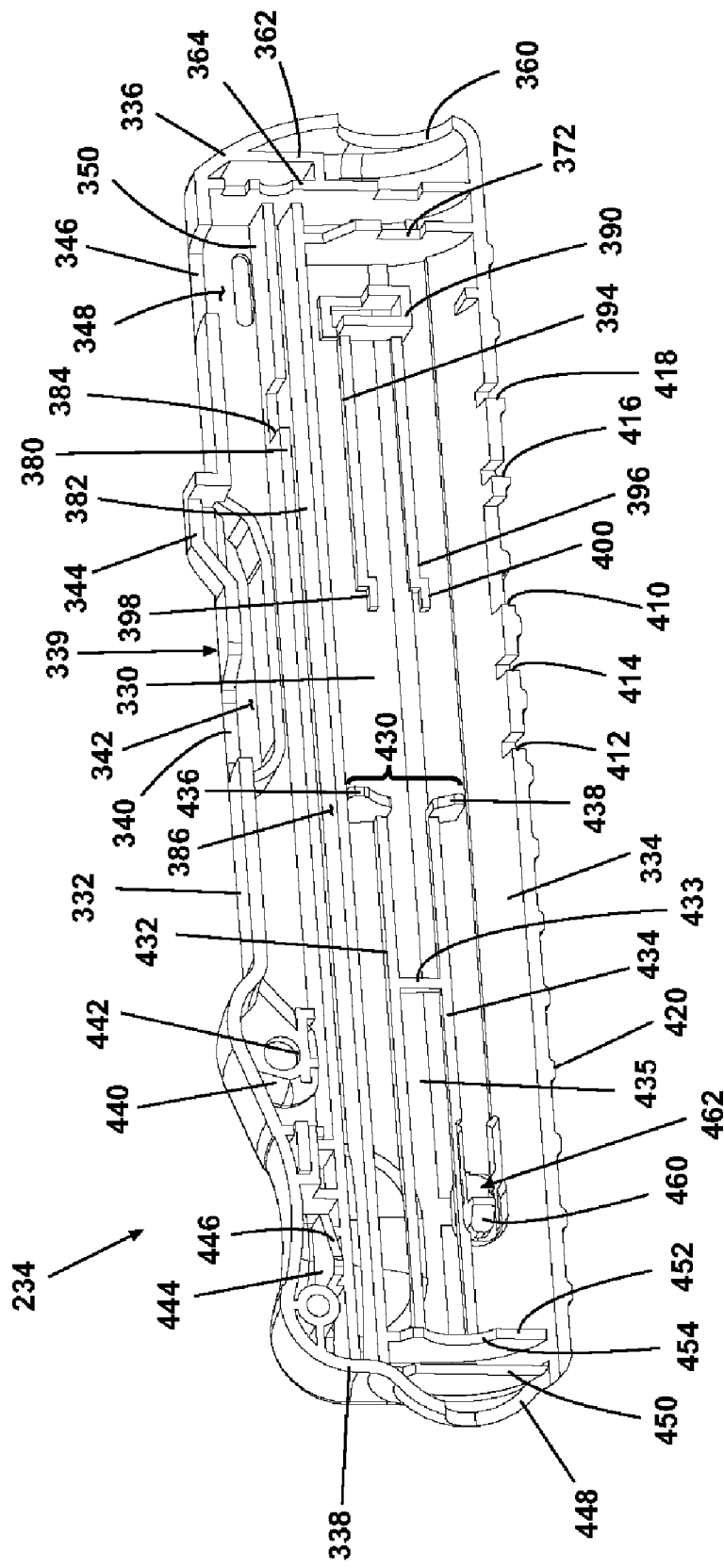
FIGS. 26A-C are perspective and enlarged partial views of a right housing shell comprising an element of the core biopsy device illustrated in FIG. 24.
Figure 26B:
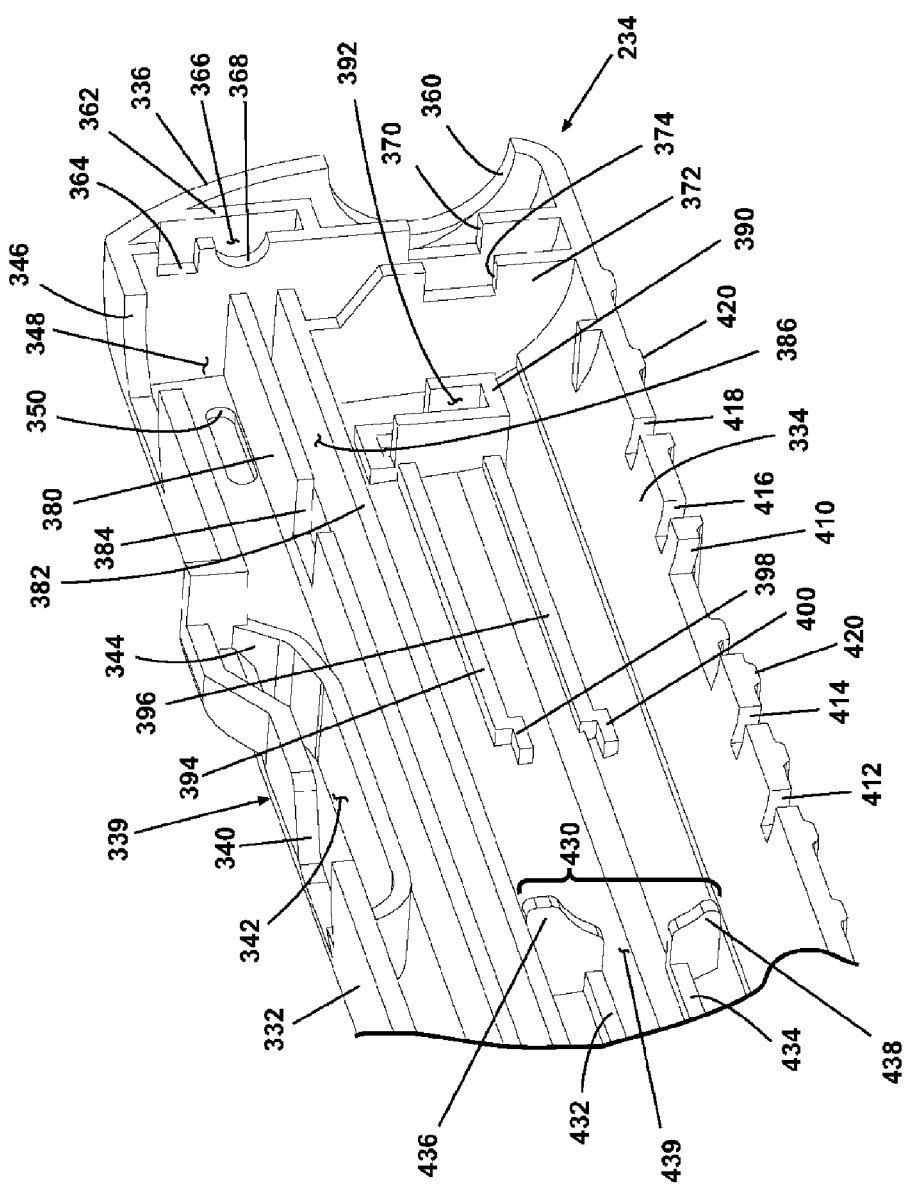

Referring specifically to FIG. 26B, the top wall 332 is provided with a swing arm opening 340 therethrough entering into a swing arm cage 339 comprising an elongated, somewhat curved swing arm chamber 342 terminating in a proximal end 344 inclined upwardly away from the swing arm opening 340. Proximal of the swing arm opening 340, the top wall 332 is provided with an upper latch opening 346 therethrough entering into a latch chamber 348. A latch slot 350 communicates with the latch chamber 348 through the side wall 330.

The proximal wall 336 curves somewhat outwardly from the top wall 332 to the bottom wall 334, and is inset with a semicircular trigger opening 360 at a lower portion thereof. Extending inwardly from the side wall 330, and depending from an upper portion of the proximal wall 336, is an abbreviated outer wall 362. Extending inwardly from the side wall 330, and from the top wall 332 to the bottom wall 334, parallel to the outer wall 362, is an intermediate wall 364. An upper portion of the intermediate wall 364 is joined to the outer wall 362 to form a narrow spring retainer chamber 366. The intermediate wall 364 is inset with a semicircular spring retainer opening 368 at an upper portion thereof in communication with the spring retainer chamber 366, and with a rectilinear intermediate trigger opening 370 at a lower portion thereof in axial alignment with the trigger opening 360. Extending inwardly from the side wall 330, and upwardly from the bottom wall 334, parallel to the intermediate wall 364, is an inner wall 372. The inner wall 372 is inset with a rectilinear distal trigger opening 374 in axial alignment with the intermediate trigger opening 370 and the trigger opening 360.

Extending inwardly from the sidewall 330 generally parallel to the top wall 332, and from the intermediate wall 364 toward the distal wall 338, are an upper interior wall 380 and a lower interior wall 382 in parallel, spaced-apart juxtaposition. The upper interior wall 380 is inset with a rectilinear lower latch opening 384 therethrough at a proximal end thereof. The upper interior wall 380 and the lower interior wall 382 define an elongated shuttle slot 386 therebetween.

Extending inwardly from the side wall 330, distally of the inner wall 372 and ventrally of the lower interior wall 382, is a rectilinear latch plate support 390 defining a latch plate channel 392. Extending inwardly from the side wall 330 and distally from the latch plate support 390 are an upper spoon cannula carriage rail 394 and a lower spoon cannula carriage rail 396 in parallel, spaced-apart juxtaposition. The upper spoon cannula carriage rail 394 terminates in an upper stop 398. The lower spoon cannula carriage rail 396 terminates in a lower stop 400. The carriage rails 394, 396 are generally parallel to the upper interior wall 380 and the lower interior wall 382. A cutting cannula carriage cradle 430 comprises an upper cradle piece 436 and a lower cradle piece 438 extending inwardly from an intermediate location on the side wall 330 and defining an arcuate, inward-facing surface. The cradle pieces 436, 438 are separated by a slot 439.

Figure 26C:
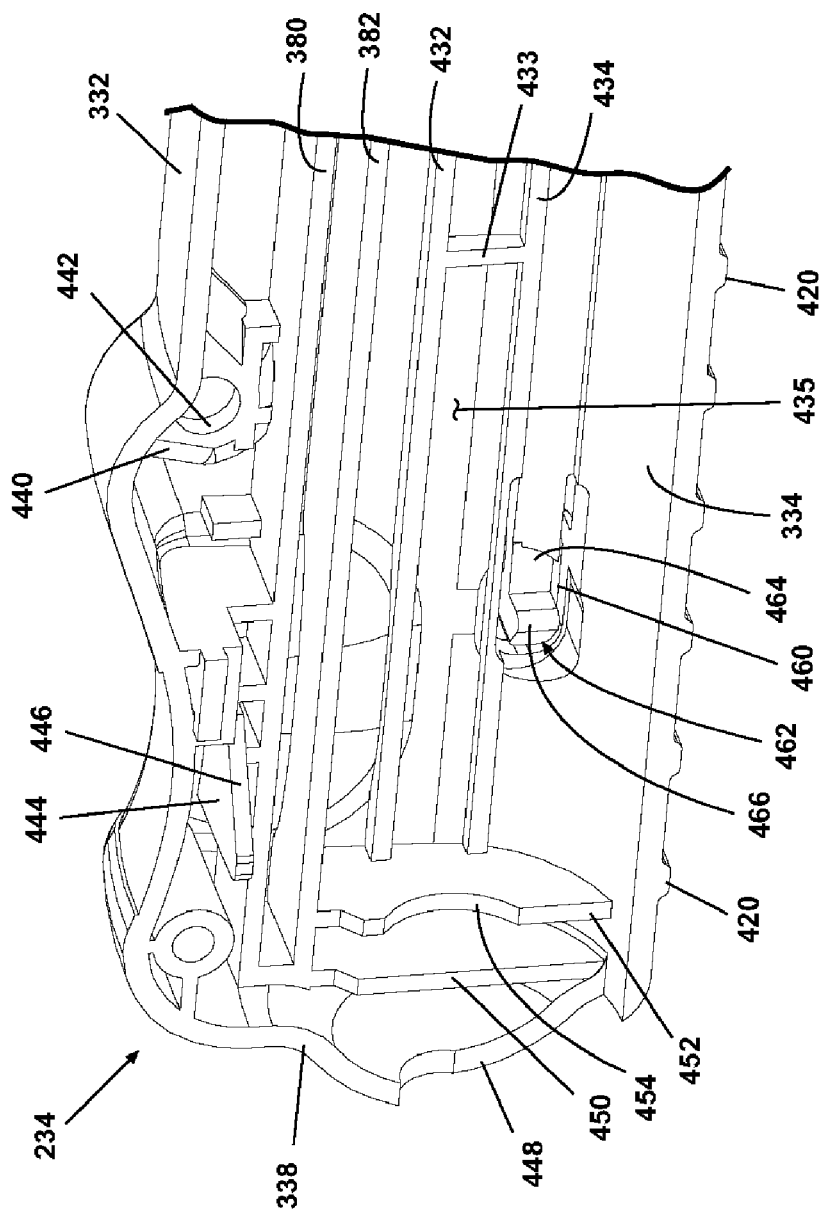

Referring now to FIG. 26C, the upper interior wall 380 and the lower interior wall 382 extend distally to an intermediate wall 450 extending inwardly from the side wall 330 and upwardly from the bottom wall 334. An inner wall 452 extends inwardly from the side wall 330 and upwardly from the bottom wall 334 parallel to the intermediate wall 450. The inner wall 452 is inset with a nosepiece opening 454 therethrough. Referring again to FIG. 26B, an upper rib 432 and a lower rib 434 extend inwardly from the side wall 330 from the cutting cannula carriage cradle 430 to the inner wall 452 in parallel, spaced-apart juxtaposition, ventrally of and generally parallel to the lower interior wall 382 to define a slot 435.

A stop rib 433 extends orthogonally from the upper rib 432 to the lower rib 434 intermediate the ends of the ribs 432, 434.

Figure 27:
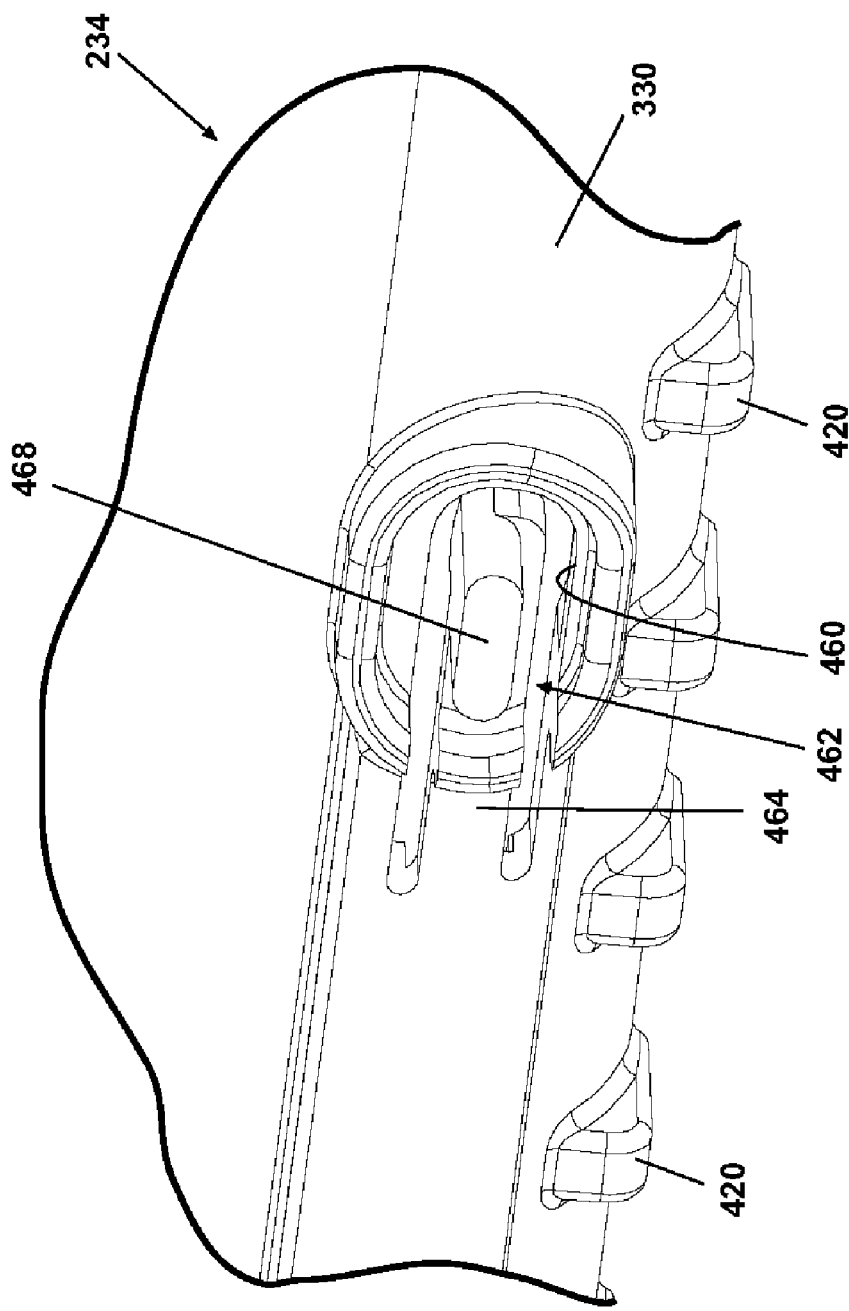
FIG. 27 is an enlarged view of a portion of the right housing shell illustrated in FIGS. 26A-C.

Referring also to FIG. 27, an elongated front trigger opening 460 penetrates the side wall 330 at a lower, distal region thereof, ventrally of the lower rib 434. Extending distally into the opening 460 from the proximal end thereof is a cantilevered release arm 462. The release arm 462 comprises a resilient, cantilever member 464 terminating in an inwardly-extending tooth 466. Extending outwardly from the cantilever member 464 in opposed disposition to the tooth 466 is a button boss 468.

Referring again to FIG. 26C, the distal wall 338 extends from the top wall 332 to the bottom wall 334 and has an irregular compound curvature. The distal wall 338 is inset with an irregularly-shaped nosepiece opening 448 in axial alignment with the nosepiece opening 454 in the inner wall 452.

Referring again to FIG. 26A, the bottom wall 334 extends from the distal wall 338 to the proximal wall 336 in generally parallel juxtaposition with the top wall 332. The bottom wall 334 is provided along its length with an array of regularly-spaced, laterally extending ribs 420. An elongated, rectilinear sample size selector slot 410 is inset in the bottom wall 334 proximally of the midpoint thereof. A pair of rectilinear distal slots 412, 414 is inset in the bottom wall 334 distally of the sample size selector slot 410. A pair of rectilinear proximal slots 416, 418 is inset in the bottom wall 334 proximally of the sample size selector slot 410. The spacing of the distal slots 412, 414 is equal to the spacing of the proximal slots 416, 418.

The side wall 330 and the top wall 332 transition toward the distal end of the housing shell 234 in a laterally outwardly-opening pivot receptacle 440 provided with a circular pivot aperture 442 extending therethrough. Extending inwardly from the side wall 330 intermediate the pivot receptacle 440 and the distal wall 338 is a horizontally disposed, plate-like distal cam block wedge 444 having a rearward facing inclined face 446.

Figure 28A:
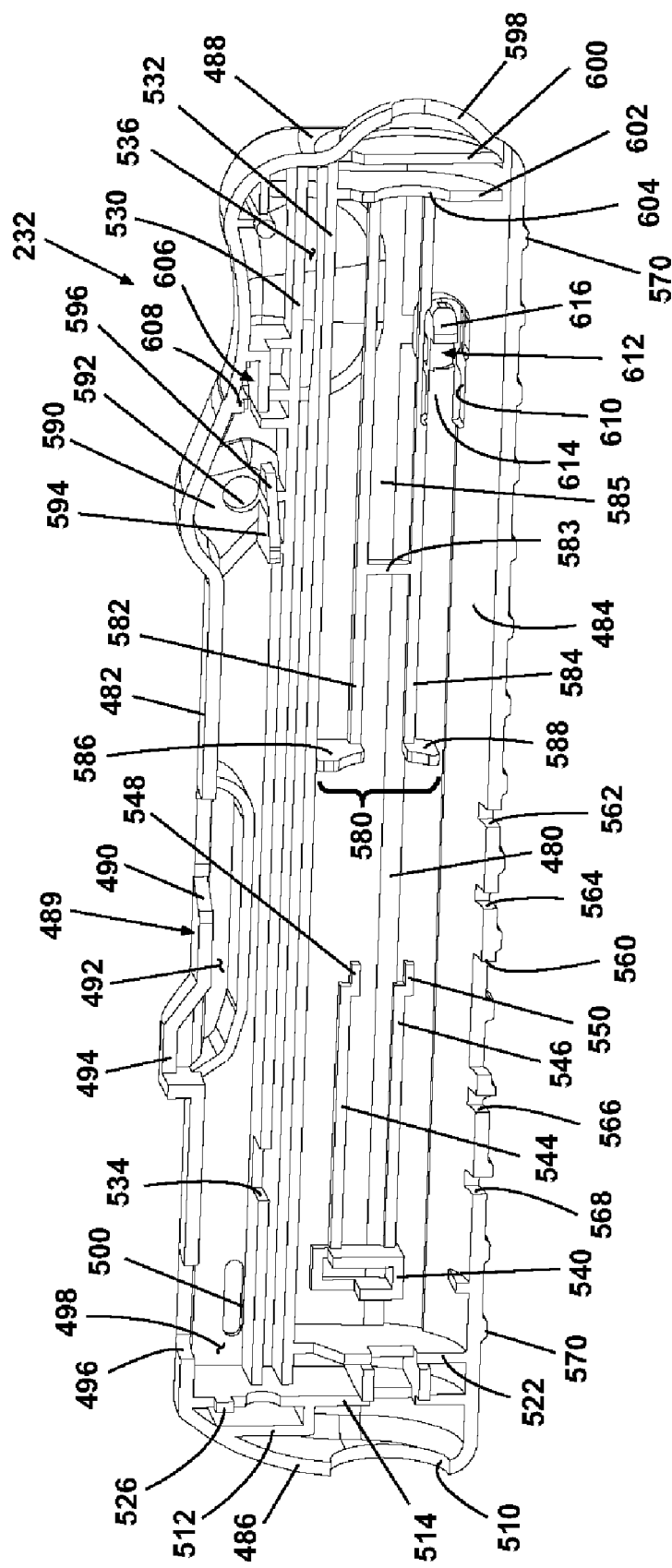
FIGS. 28A-C are perspective and enlarged partial views of a left housing shell comprising an element of the core biopsy device illustrated in FIG. 24.
Figure 28B:
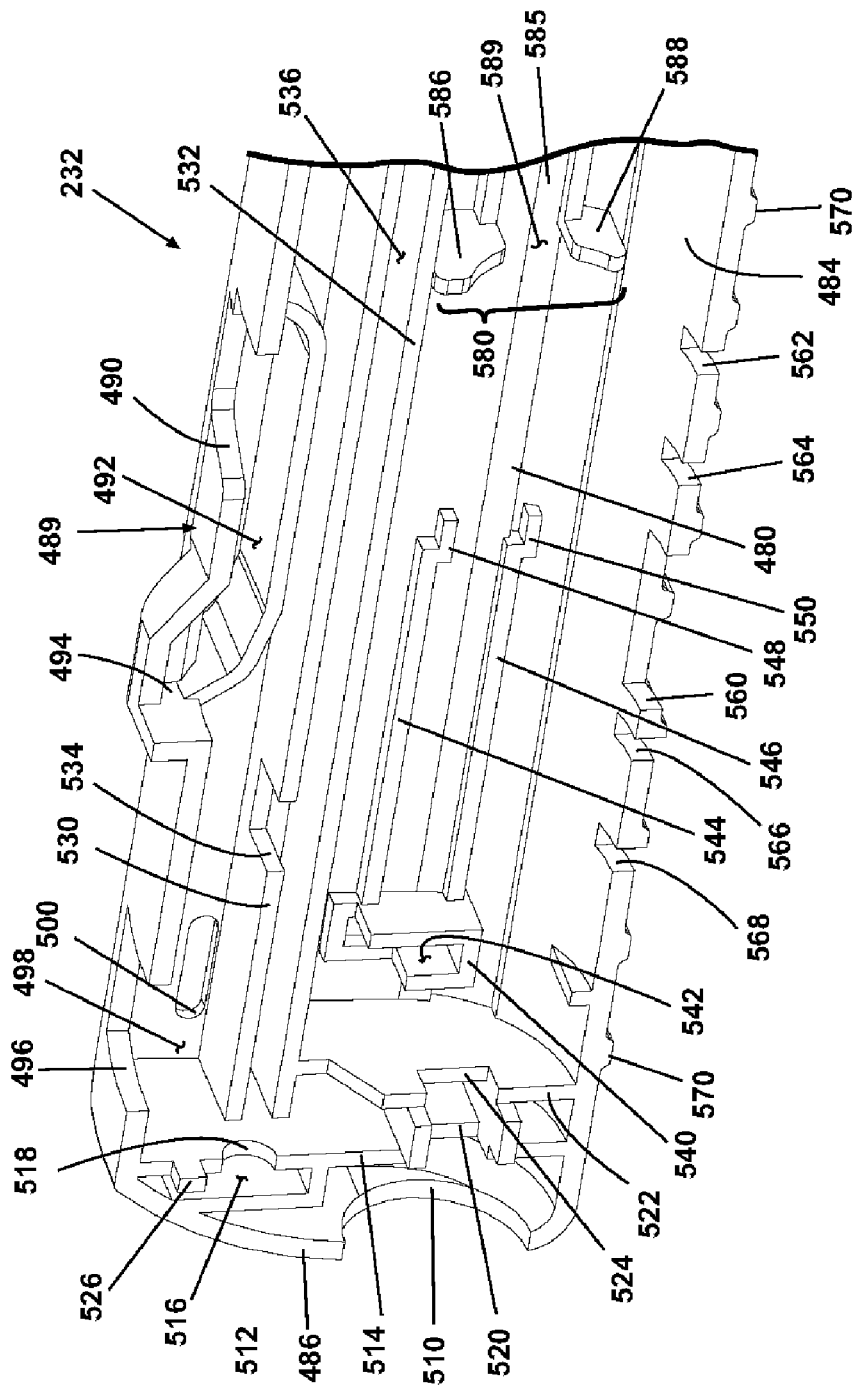

The left housing shell 232 is generally a mirror image, and has many of the same structural elements, of the right housing shell 234 arranged for cooperative registry of the structural elements in both shells 232, 234 to provide support and movement functionality to the assembled housing 230. FIGS. 28A-C and 29 illustrate the left housing shell 232. The left housing shell 232 is an irregularly-shaped, elongated body comprising an elongated side wall 480 joined to a top wall 482, a bottom wall 484, a proximal wall 486, and a distal wall 488. The walls 480-488 are contoured, and configured with openings, bosses, rails, and the like, for operational support of the elements comprising the biopsy gun 220. Referring specifically to FIG. 28B, the top wall 482 is provided with a swing arm opening 490 therethrough entering into a swing arm cage 489 comprising an elongated, somewhat curved swing arm chamber 492 terminating in a proximal end 494 inclined upwardly away from the swing arm opening 490. Proximal of the swing arm opening 490, the top wall 482 is provided with an upper latch opening 496 therethrough entering into a latch chamber 498. A latch slot 500 communicates with the latch chamber 498 through the side wall 480.

The proximal wall 486 curves somewhat outwardly from the top wall 482 to the bottom wall 484, and is inset with a semicircular trigger opening 510 at a lower portion thereof. Extending inwardly from the side wall 480, and depending from an upper portion of the proximal wall 486, is an abbreviated outer wall 512. Extending inwardly from the side wall 480, and from the top wall 482 to the bottom wall 484, parallel to the outer wall 512, is an intermediate wall 514. An upper portion of the intermediate wall 514 is joined to the outer wall 512 to form a narrow spring retainer chamber 516. The intermediate wall 514 is inset with a semicircular spring retainer opening 518 at an upper portion thereof in communication with the spring retainer chamber 516, and with a rectilinear intermediate trigger opening 520 at a lower portion thereof in axial alignment with the trigger opening 510. Extending inwardly from the intermediate wall 514 dorsally of the spring retainer opening 518 is a rectilinear retainer boss 526. Extending inwardly from the side wall 480, and upwardly from the bottom wall 484, parallel to the intermediate wall 514, is an inner wall 522. The inner wall 522 is inset with a rectilinear distal trigger opening 524 in axial alignment with the intermediate trigger opening 520 and the trigger opening 510.

Extending inwardly from the sidewall 480 generally parallel to the top wall 482, and from the intermediate wall 514 toward the distal wall 488, are an upper interior wall 530 and a lower interior wall 532 in parallel, spaced-apart juxtaposition. The upper interior wall 530 is inset with a rectilinear lower latch opening 534 therethrough at a proximal end thereof. The upper interior wall 530 and the lower interior wall 532 define an elongated shuttle slot 536 therebetween.

Extending inwardly from the side wall 480, distally of the inner wall 522 and ventrally of the lower interior wall 532, is a rectilinear latch plate support 540 defining a latch plate channel 542. Extending inwardly from the side wall 480 and distally from the latch plate support 540 are an upper spoon cannula carriage rail 544 and a lower spoon cannula carriage rail 546 in parallel, spaced-apart juxtaposition. The upper spoon cannula carriage rail 544 terminates in an upper stop 548. The lower spoon cannula carriage rail 546 terminates in a lower stop 550. The carriage rails 544, 546 are generally parallel to the upper interior wall 530 and the lower interior wall 532. A cutting cannula carriage cradle 580 comprises an upper cradle piece 586 and a lower cradle piece 588 extending inwardly from an intermediate location on the side wall 480 and defining an arcuate, inward-facing surface. The cradle pieces 586, 588 are separated by a slot 589.

Figure 28C:
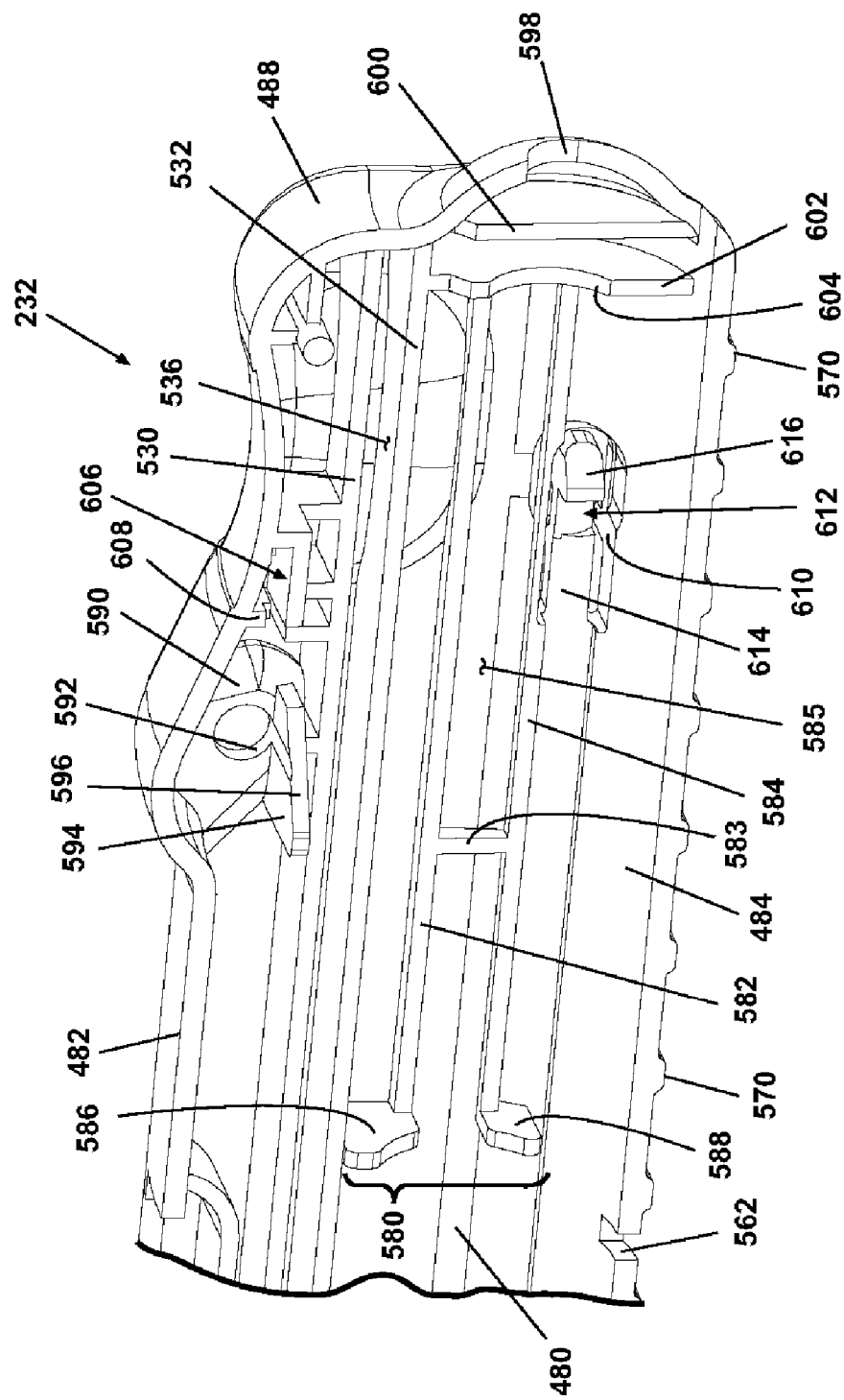

Referring now to FIG. 28C, the upper interior wall 530 and the lower interior wall 532 extend distally to an intermediate wall 600 extending inwardly from the side wall 480 and upwardly from the bottom wall 484. An inner wall 602 extends inwardly from the side wall 480 and upwardly from the bottom wall 484 parallel to the intermediate wall 600. The inner wall 602 is inset with a nosepiece opening 604 therethrough. Referring again to FIG. 28B, an upper rib 582 and a lower rib 584 extend inwardly from the side wall 480 from the cutting cannula carriage cradle 580 to the inner wall 602 in parallel, spaced-apart juxtaposition, ventrally of and generally parallel to the lower interior wall 532 to define a slot 585. A stop rib 583 extends orthogonally from the upper rib 582 to the lower rib 584 intermediate the ends of the ribs 582, 584.

Figure 29:
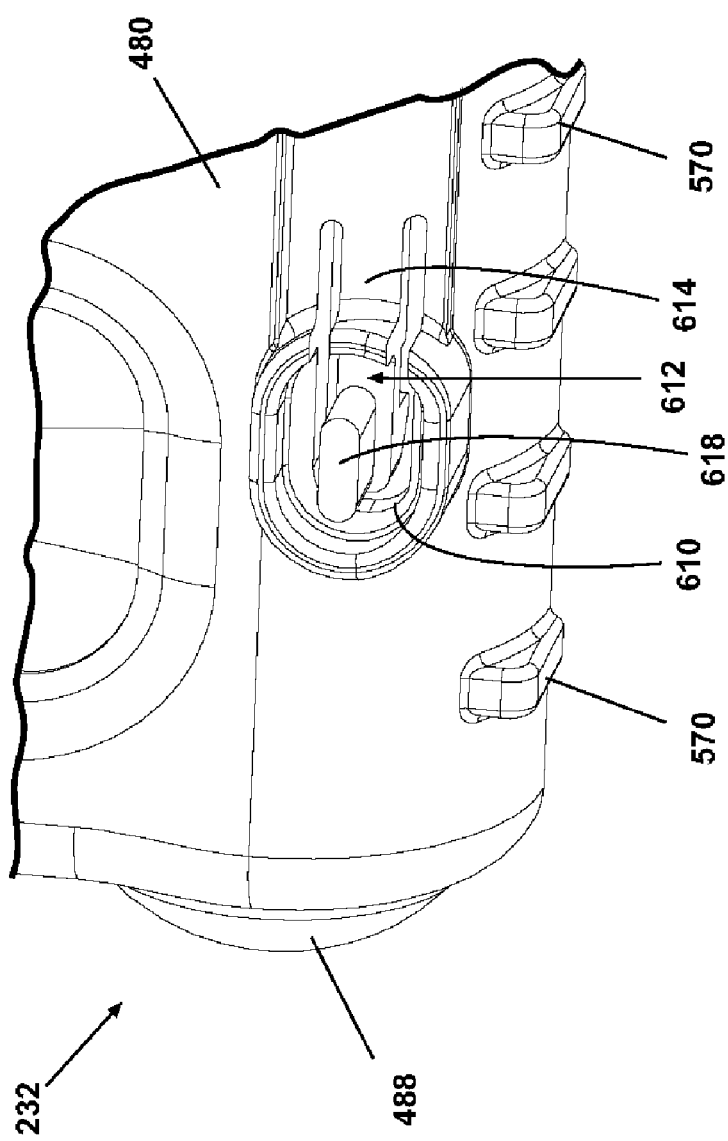
FIG. 29 is an enlarged view of a portion of the right housing shell illustrated in FIGS. 26A-C.

Referring also to FIG. 29, an elongated front trigger opening 610 penetrates the side wall 480 at a lower, distal region thereof, ventrally of the lower rib 584. Extending distally into the opening 610 from the proximal end thereof is a cantilevered release arm 612. The release arm 612 comprises a resilient, cantilever member 614 terminating in an inwardly-extending tooth 616. Extending outwardly from the cantilever member 614 in opposed disposition to the tooth 616 is a button boss 618.

Referring again to FIG. 28C, the distal wall 488 extends from the top wall 482 to the bottom wall 484 and has an irregular compound curvature. The distal wall 488 is inset with an irregularly-shaped nosepiece opening 598 in axial alignment with the nosepiece opening 604 in the inner wall 602.

Referring again to FIG. 28A, the bottom wall 484 extends from the distal wall 488 to the proximal wall 486 in generally parallel juxtaposition with the top wall 482. The bottom wall 484 is provided along its length with an array of regularly-spaced, laterally extending ribs 570. An elongated, rectilinear sample size selector slot 560 is inset in the bottom wall 484 proximally of the midpoint thereof. A pair of rectilinear distal slots 562, 564 is inset in the bottom wall 484 distally of the sample size selector slot 560. A pair of rectilinear proximal slots 566, 568 is inset in the bottom wall 484 proximally of the sample size selector slot 560. The spacing of the distal slots 562, 564 is equal to the spacing of the proximal slots 566, 568.

The side wall 480 and the top wall 482 transition toward the distal end of the housing shell 232 in a laterally outwardly-opening pivot receptacle 590 provided with a circular pivot aperture 592 extending therethrough. Extending inwardly from the pivot receptacle 590 immediately below the pivot aperture 592 is a horizontally disposed, plate-like proximal cam block wedge 594 having a forward facing inclined face 596. Distally of the pivot receptacle 590 is a rectilinear cam spring housing 606 having a stop wall 608 depending from the top wall 482. The stop wall 608 is separated from the cam spring housing 606 so that the cam spring housing 606 opens proximally toward the pivot receptacle 590.

The housing shells 232, 234 are provided with a suitable number of connecting elements, such as snapfit retainers, post and seat structures, threaded fastener apertures and seats, and the like, for fixedly interconnecting the housing shells 232, 234 to form the housing 230.

Figure 30:
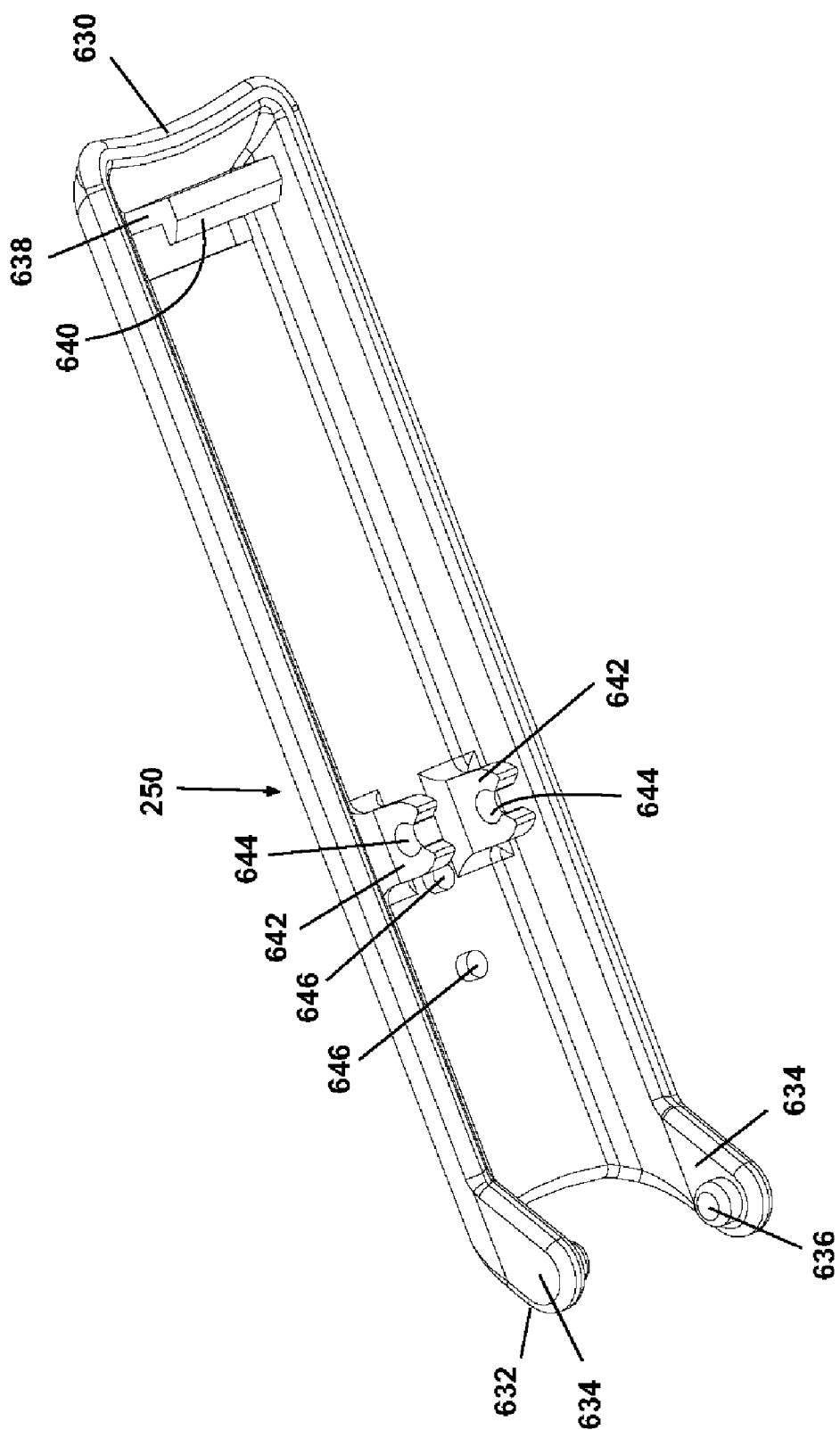
FIG. 30 is a perspective view of the underside of a handle comprising an element of the cocking handle assembly illustrated in FIG. 24.

Referring now to FIG. 30, the handle 250 is an elongated, beam-like member having a proximal end 630 and a distal end 632. The distal end 632 terminates in a pair of parallel, spaced-apart, inclined pivot extensions 634, each of which terminates in an inwardly extending pivot boss 636. The pivot extensions 634 and pivot bosses 636 are adapted for receipt in the pivot receptacles 440, 590 and the pivot apertures 442, 592, respectively, with the housing shells 232, 234 in an assembled configuration. The pivot receptacles 440, 590 are adapted for pivotal movement of the handle 250 about an axis coaxial with the pivot apertures 442, 592.

A latch extension 638 extends orthogonally from the underside of the handle 250 at the proximal end 630 thereof, terminating in a hook 640 extending toward the distal end 632. A pair of parallel, spaced-apart swing arm supports 642 extends from the underside of the handle 250 intermediate the proximal end 630 and the distal end 632. The swing arm supports 642 are provided with pivot openings 644 defining a rotational axis orthogonal to the longitudinal axis of the handle 250. Intermediate the swing arm supports 642 and the distal end 632 is a pair of cylindrical spring mounting bosses 646 extending from the underside of the handle 250.

Figure 31:
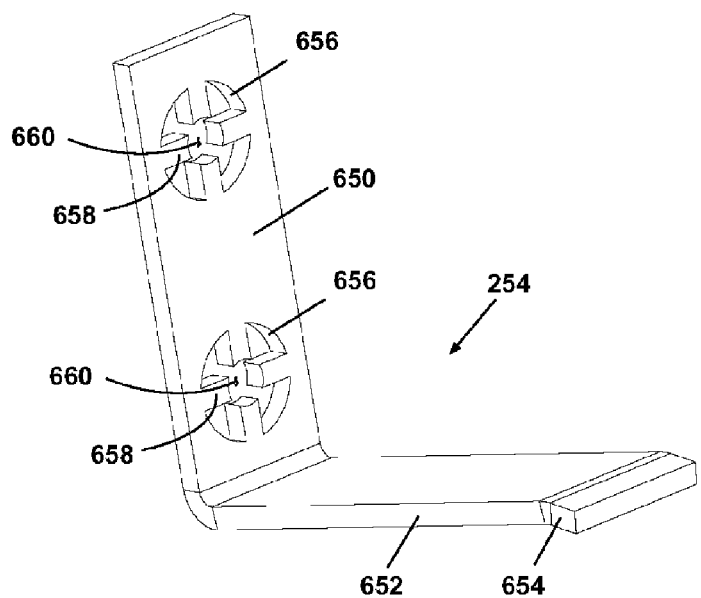
FIG. 31 is a perspective view of a spring comprising an element of the cocking handle assembly illustrated in FIG. 24.

Referring now to FIG. 31, the spring 254 is a resilient, generally L-shaped member comprising a mounting arm 650 and a contact arm 652 extending generally orthogonally therefrom. The contact arm 652 terminates in a flange 654 inclined somewhat away from the mounting arm 650. A spaced pair of mounting openings 656 having a generally circular configuration extends through the mounting arm 650. A plurality, illustrated in FIG. 31 as numbering four, of mounting fingers 658 extends in cantilevered fashion radially inwardly from the perimeter of each mounting opening 656 to terminate in spaced disposition to define a center aperture 660 coaxial with the center of the mounting opening 656. The ends of each finger 658 can be provided with a curved tip to define a circular center aperture 660. The size of the center apertures 660 is adapted for insertion of the spring mounting bosses 646 therethrough for fixed frictional attachment of the spring 254 to the handle 250. The spring 254 is fabricated of a suitable material, such as steel or high strength plastic, having sufficient strength and resiliency for the purposes described herein.

Figure 32:
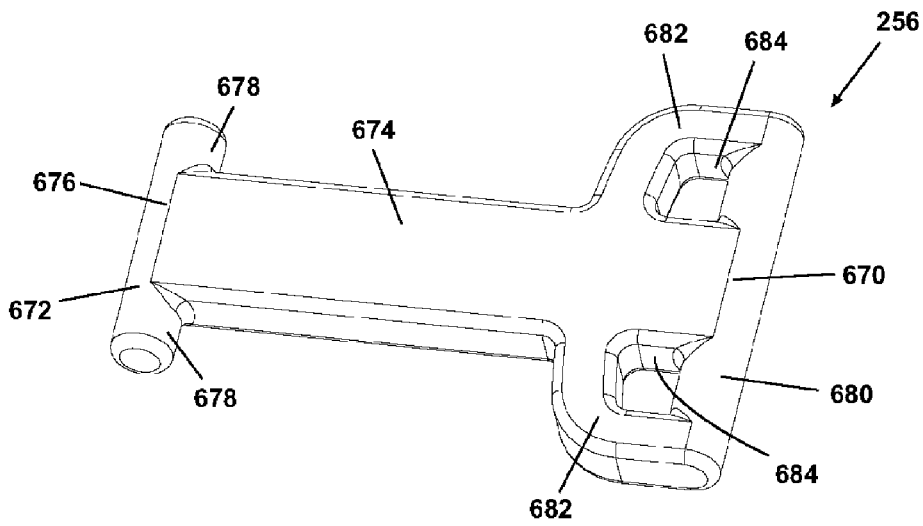
FIG. 32 is a perspective view of a swing arm comprising an element of the cocking handle assembly illustrated in FIG. 24.

As illustrated in FIG. 32, the swing arm 256 is a generally flattened, somewhat T-shaped member having a pivot end 670 and a sliding end 672 interconnected by a center beam 674. The sliding end 672 comprises a cylindrically shaped sliding rod 676 orthogonal to the longitudinal axis of the center beam 674 and extending laterally away from the center beam 674 to define a pair of opposed end bosses 678. The pivot end 670 comprises a cylindrically shaped pivot rod 680 orthogonal to the longitudinal axis of the center beam 674 and extending laterally away from the center beam 674, parallel to the sliding rod 676. A pair of curved buttresses 682 extend from the ends of the pivot rod 680 to join the center beam 674 at an intermediate region thereof, to define with the pivot rod 680 and the center beam 674 a pair of spaced-apart openings 684. The sections of the pivot rod 680 adjacent the openings 684 are adapted for insertion into the pivot openings 644 of the swing arm supports 642 of the handle 250 for pivotal mounting of the swing arm 256 to the handle 250. Preferably, the swing arm supports 642 are adapted so that the pivot rod 680 is snapped into the pivot openings 644.

Figure 33A:
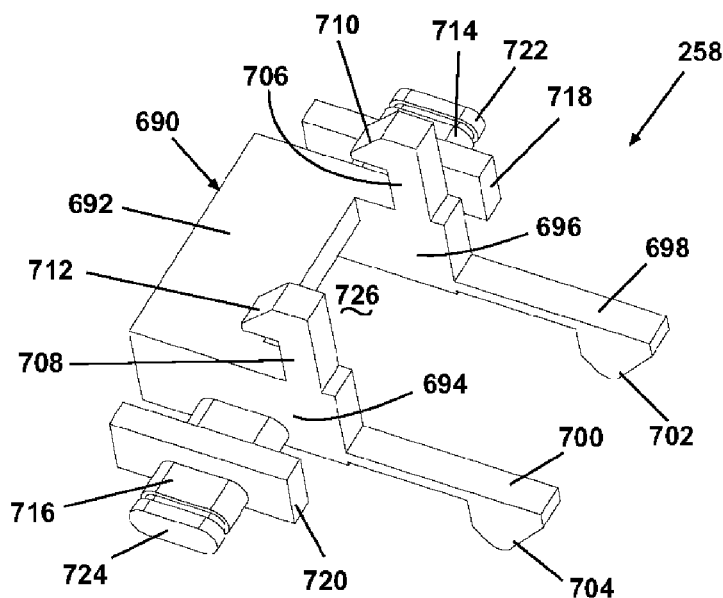
FIGS. 33A-C are perspective views of a latch comprising an element of the cocking handle assembly illustrated in FIG. 24.
Figure 33B:
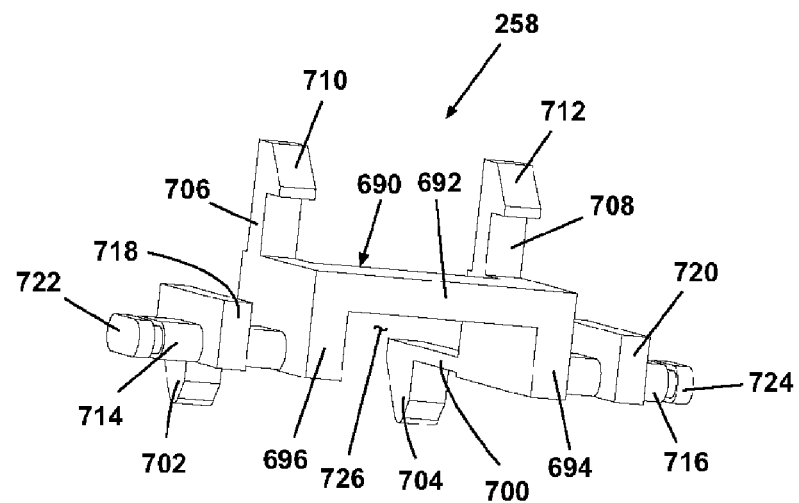
Figure 33C:
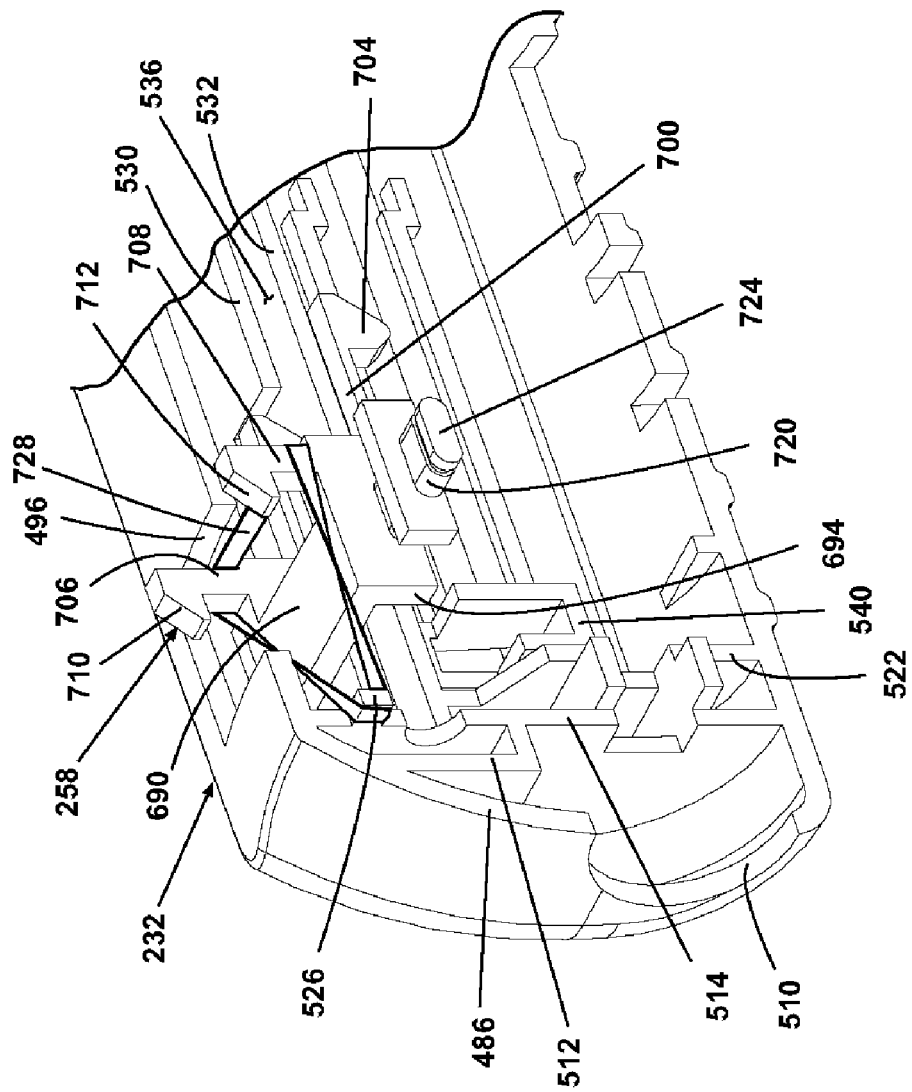

Referring now to FIGS. 33A-C, the latch 258 is a carriage-like body comprising a rectilinear frame portion 690 having a center wall 692 joining a pair of orthogonally-depending, spaced-apart sidewalls 694, 696. The center wall 692 and side walls 694, 696 define a rectilinear shuttle cavity 726. Extending away from the side wall 694 in cantilever fashion and coplanar therewith is a flex arm 700 terminating away from the side wall 694 in a downwardly depending tooth 704. Parallel to the flex arm 700, extending away from the side wall 696 in cantilever fashion and coplanar therewith is a flex arm 698 terminating away from the side wall 696 in a downwardly depending tooth 702. Extending away from the center wall 692 in cantilever fashion coplanar with the side wall 694 is a latch arm 708 terminating away from the center wall 692 in a hook 712 extending above the center wall 692. Extending away from the center wall 692 in cantilever fashion coplanar with the side wall 696 is a latch arm 706 terminating away from the center wall 692 in a hook 710 extending above the center wall 692. A flattened lateral beam 714 extends outwardly away from the side wall 696 to terminate in a button mount 722. An elongated flange plate 718 intersects the lateral beam 714 parallel to and spaced away from the side wall 696. A flattened lateral beam 716 extends outwardly away from the side wall 694 to terminate in a button mount 724. An elongated flange plate 720 intersects the lateral beam 716 parallel to and spaced away from the side wall 694. The lateral beams 714, 716 are coaxially aligned.

As illustrated in FIG. 33C, the latch 258 is provided with an elastic band 728 adapted to encircle the latch arms 706, 708 and the retainer boss 526 when the latch 258 is installed in the housing 230, as hereinafter described.

Figure 34A:
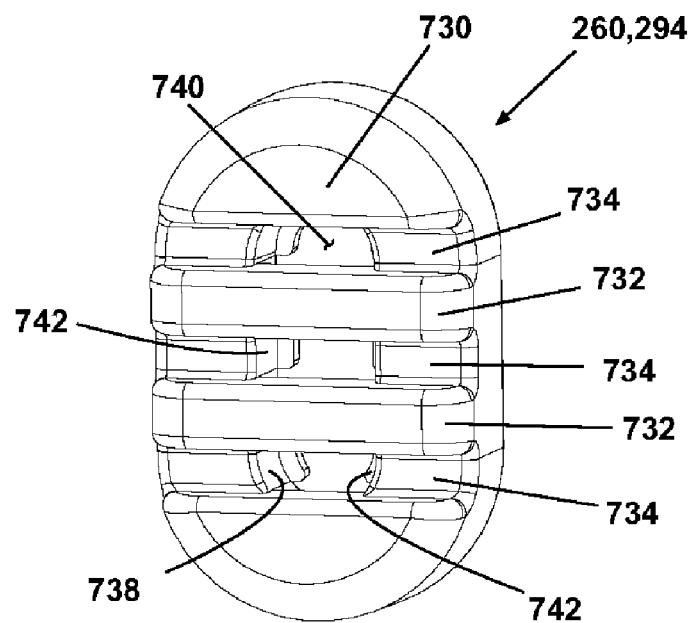
FIGS. 34A-B are perspective views of a button comprising an element of the cocking handle assembly and trigger assembly illustrated in FIG. 24.
Figure 34B:
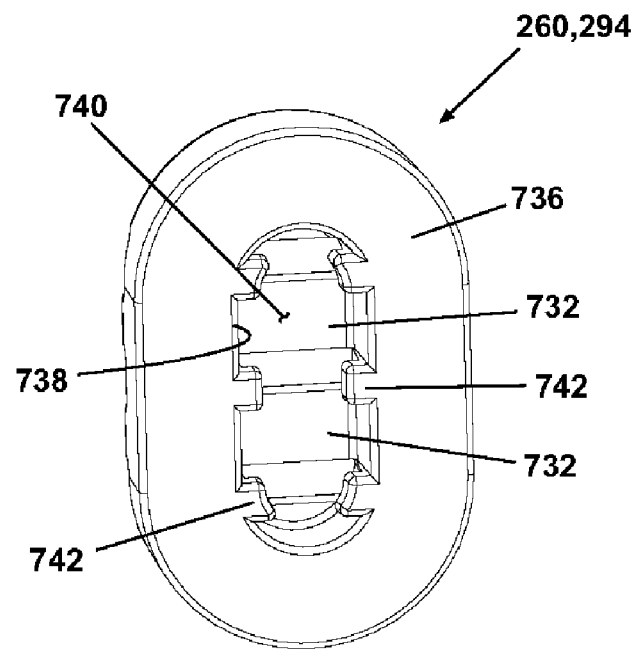

Referring now to FIGS. 34A-B, the button 260, 294 is a somewhat oval-shaped, rounded body having an outer surface 730 and an opposed inner surface 736. The outer surface 730 is divided into ribs 732 by an array of regularly-spaced slots 734 oriented orthogonal to the longitudinal axis of the button 260, 294. A somewhat oval-shaped perimeter wall 738 depends from the inner surface 736 to the ribs 732 to define a cavity 740. The cavity 740 is adapted for slidable insertion of a button mount 722, 724, or a button boss 318, 468, therein. A plurality of inwardly extending pegs 742 is spaced around the perimeter wall 738 to facilitate the fixed attachment of the button 260 to the button mount 722, 724, and the button boss 318, 468.

As illustrated in FIGS. 35A-G, the shuttle 270 is an elongated carriage-like body having a proximal end 750 and a distal end 752, and comprising a plate portion 754 and a box portion 756. The plate portion 754 extends from the distal end 752 into cooperative registry with the box portion 756, terminating in a plate proximal end 755 at approximately the mid-line of the box portion 756. The box portion 756 extends from the plate portion 754 to the proximal end 750. The plate portion 754 is an elongated, plate-like member having an upper surface 758 and a lower surface 760. A rectilinear opening 762 extends through the plate portion 754 near the distal end 752.

Figure 35A:
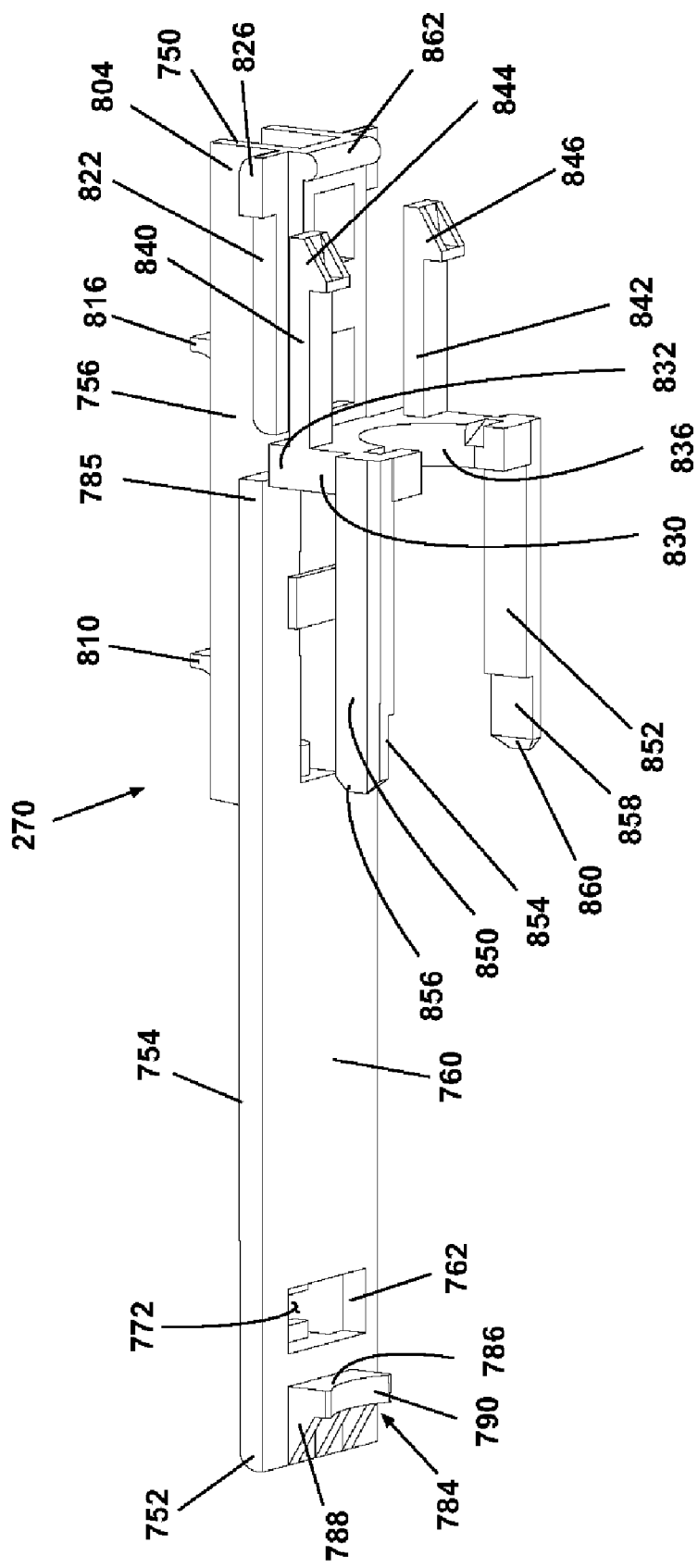
FIGS. 35A-G are perspective and enlarged partial views of a shuttle comprising an element of the shuttle assembly illustrated in FIG. 24.
Figure 35B:
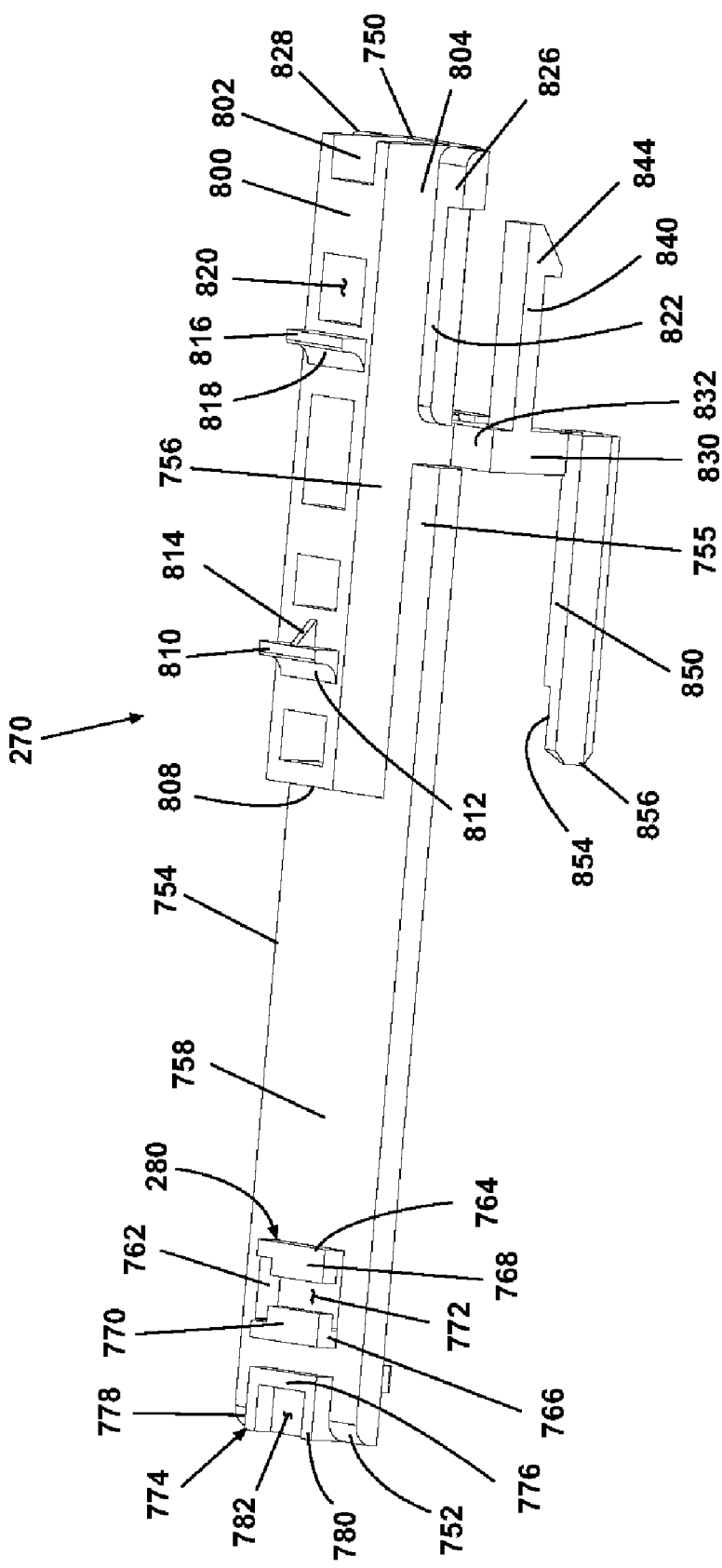
Figure 35C:
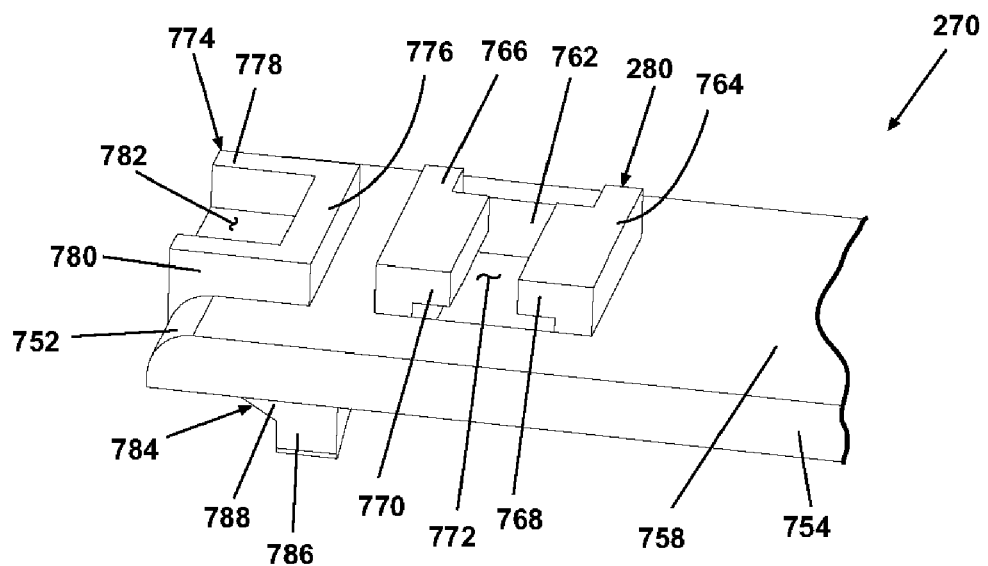

Referring to FIG. 35C, a cam block retainer 280 comprises an inner wall 764 extending laterally along the opening 762 orthogonally away from the upper surface 758, and an outer wall 766 extending laterally along the opening 762 orthogonally away from the upper surface 758 parallel to the inner wall 764. An inner flange 768 extends orthogonally along the top of the inner wall 764 over the opening 762, and an outer flange 770 extends orthogonally along the top of the outer wall 766 over the opening 762 coplanar with the inner flange 768 in spaced disposition therewith to define a gap 772 therebetween.

Figure 35D:
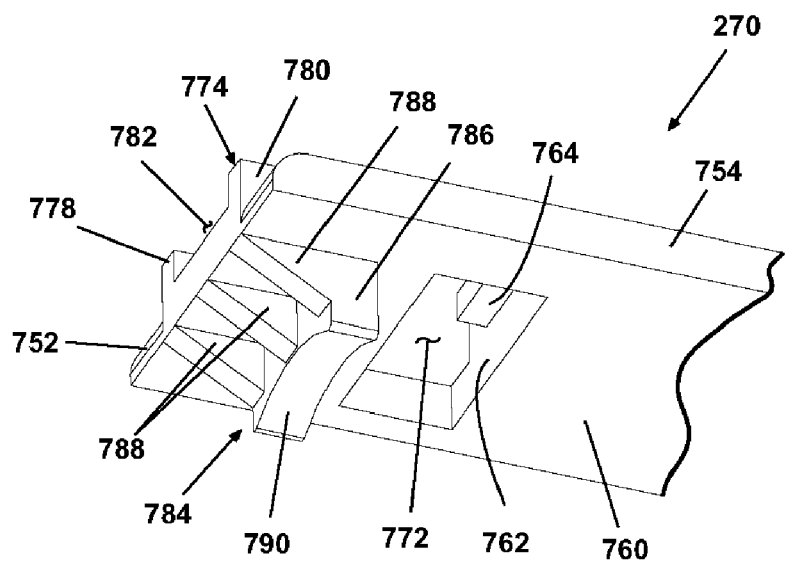

An end box 774 extends distally of the cam block retainer 280 and comprises an inner wall 776 extending orthogonally away from the upper surface 758, and a pair of side walls 778, 780 extending orthogonally away from the upper surface 758 and the inner wall 776 in parallel, spaced-apart juxtaposition. The walls 776-780 define a rectilinear chamber 782 opening toward the distal end 752. Referring to FIG. 35D, depending from the lower surface 760 intermediate the distal end 752 and the opening 762 is a cradle 784 comprising a cradle wall 786 terminating in an arcuate surface 790 opening away from the lower surface 760. The cradle wall 786 is reinforced with a plurality of triangular braces 788 between the cradle wall 786 and the distal end 752. The distal end 752 terminates in a rounded edge depending from the upper surface 758.

Figure 35E:
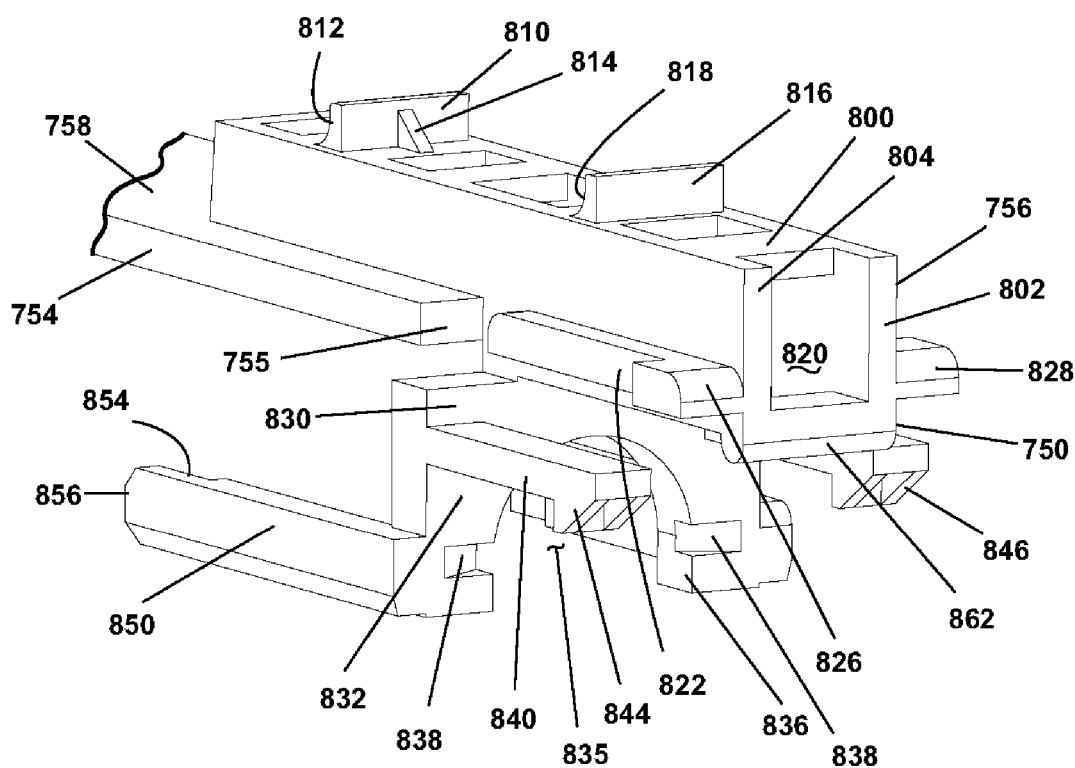

Referring to FIGS. 35E and F, the box portion 756 is an elongated, rectilinear structure comprising a top wall 800 parallel to and spaced away from the upper surface 758 of the plate portion 754, and a bottom wall 806 parallel to and spaced away from the top wall 800 parallel to the plate portion 754. A pair of parallel, spaced-apart side walls 802, 804 depends orthogonally from the top wall 800 for connection, in part, with the plate portion 754 and, in part, with the bottom wall 806. An inner end wall 808 extends orthogonally away from the upper surface 758 of the plate portion 754 to join the side walls 802, 804 to enclose a distal end of the box portion 756. The walls 800-808 define an elongated, rectilinear chamber 820. As illustrated in FIG. 24G, a cylindrical spring boss 864 extends orthogonally from the inner end wall 808 into the chamber 820.

Referring again to FIGS. 35E and F, an inner bearing wall 810 extends orthogonally away from the top wall 800 adjacent the inner end wall 808. The inner bearing wall 810 is provided with an arcuate surface 812 on the distal side of the wall 810. A triangular brace 814 extends from the proximal side of the inner bearing wall 810 to the top wall 800. An outer bearing wall 816 extends orthogonally away from the top wall 800 intermediate the inner bearing wall 810 and the proximal end 750. The outer bearing wall 816 is provided with an arcuate surface 818 on the distal side of the wall 816.

An elongated side rib 822 extends laterally away from the side wall 804 coplanar with the plate portion 754. An end boss 826 extends laterally away from the proximal end of the side rib 822. An elongated side rib 824 extends laterally away from the side wall 802 coplanar with the plate portion 754. An end boss 828 extends laterally away from the proximal end of the side rib 824. The proximal end of each end boss 826, 828 is rounded. Depending from the proximal end of the bottom wall 806 is a semicylindrical end boss 862 disposed transversely of the longitudinal axis of the shuttle 270.

Figure 35F:
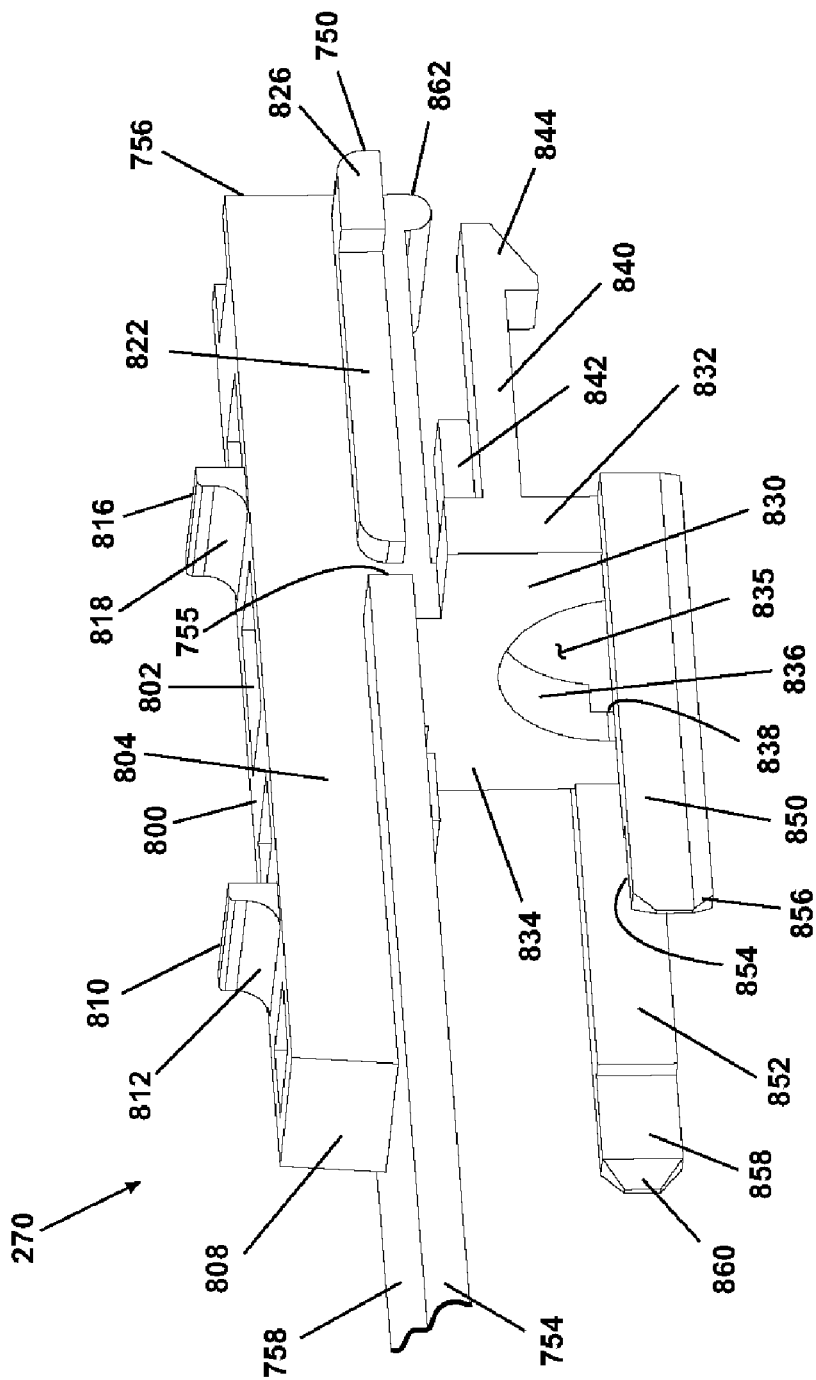
Figure 35G:
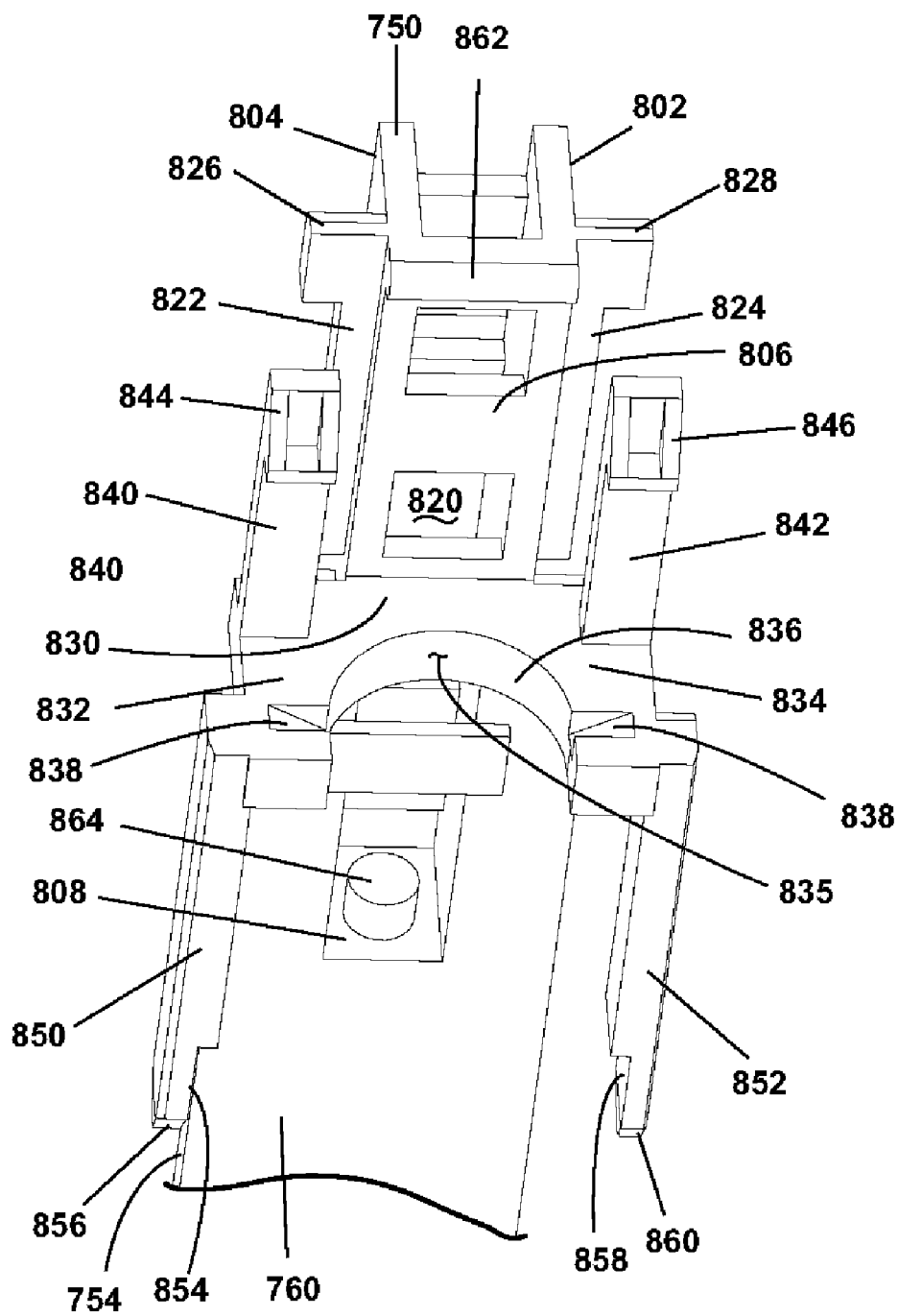

Referring to FIGS. 35E-G, depending orthogonally from the bottom wall 806 proximally of the plate proximal end 755 is an intermediate wall 830 inset with a cradle opening 835 opening ventrally away from the box portion 756 and defined by an arcuate surface 836. The lateral sides of the cradle 835 define a pair of downwardly-depending wings 832, 834. The proximal side of each wing 832, 834 is inset with a chamfered notch 838 inclined inwardly toward the cradle opening 835. Extending proximally from each wing 832, 834 parallel to the side walls 802, 804, respectively, is a cantilevered flex arm 840, 842, respectively, terminating proximally in a downwardly-depending hook 844, 846. Each flex arm 840, 842, terminates somewhat distally of the adjacent end boss 826, 828. Extending distally from a lower lateral portion of each wing 832, 834, parallel to the side walls 802, 804 is a cantilevered lower rail 850, 852. The lower rail 850 terminates in an inset end portion 854 having a tapered tip 856. The lower rail 852 terminates in an inset end portion 858 having a tapered tip 860.

Figure 36:
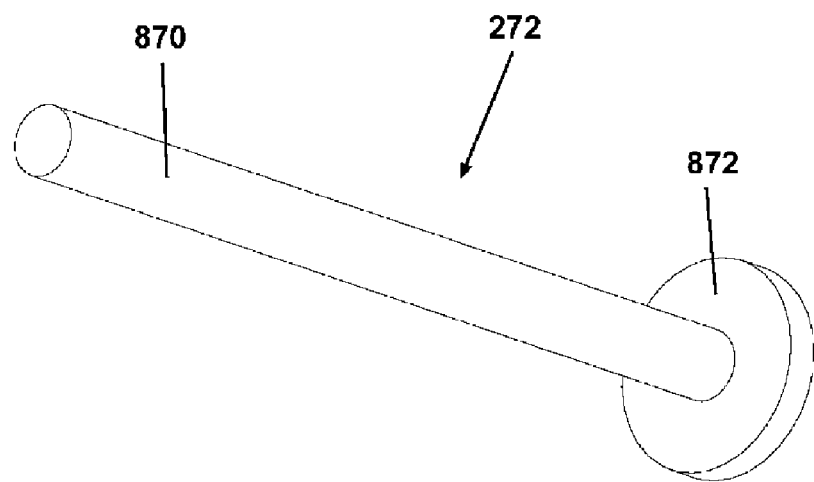
FIG. 36 is a perspective view of a spring retainer comprising an element of the shuttle assembly illustrated in FIG. 24.

As illustrated in FIG. 36, the spring retainer 272 is an elongated, somewhat nail-shaped member comprising a cylindrical rod 870 terminating at one end in a circular flange 872 coaxial with the rod 870. The rod 870 is adapted for slidable receipt in the spring retainer openings 368, 518 with the flange 872 received in the spring retainer chambers 366, 516.

Figure 37:
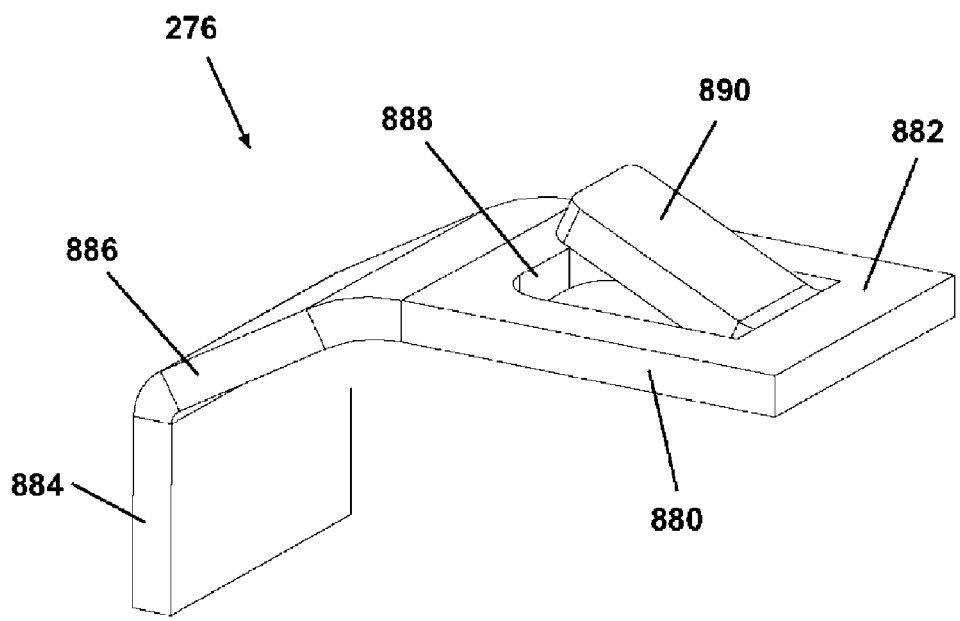
FIG. 37 is a perspective view of a cam spring comprising an element of the shuttle assembly illustrated in FIG. 24.

Referring to FIG. 37, the cam spring 276 is a somewhat L-shaped member having an upper leg 880 and a lower leg 884 angled away from the upper leg 880, the upper leg 880 and the lower leg 884 being interconnected by an inclined member 886. The upper leg 880 has an upper surface 882. A generally rectilinear opening 888 extends through the upper leg 880. A finger 890 extends in cantilevered fashion into the opening 888 toward the inclined member 886, and is inclined above the upper surface 882 to form a somewhat hook-like structure. The cam spring 276 is fabricated of a suitable material, such as steel or high strength plastic, having sufficient strength and resiliency for the purposes described herein.

Figure 38A:
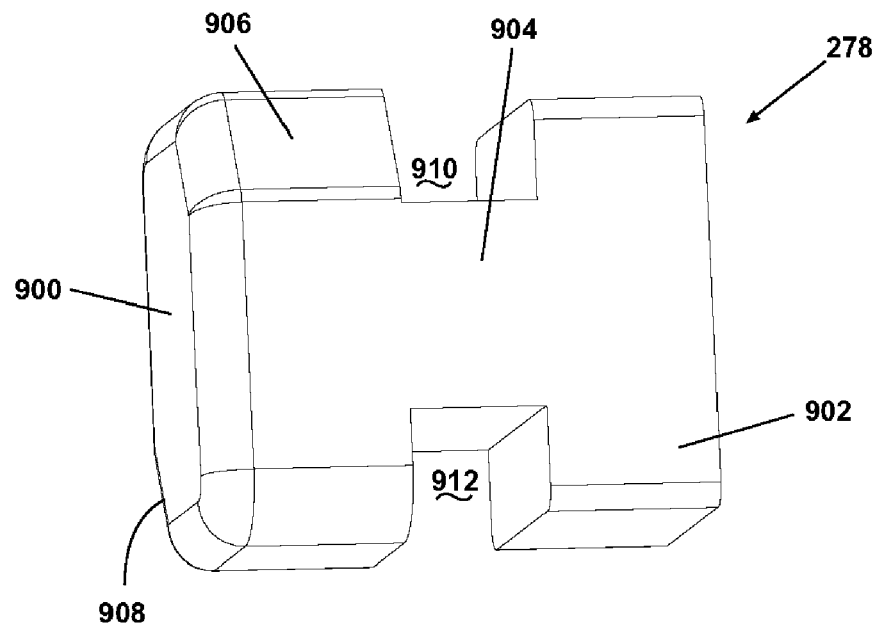
FIGS. 38A-B are perspective views of a cam block comprising an element of the shuttle assembly illustrated in FIG. 24.
Figure 38B:
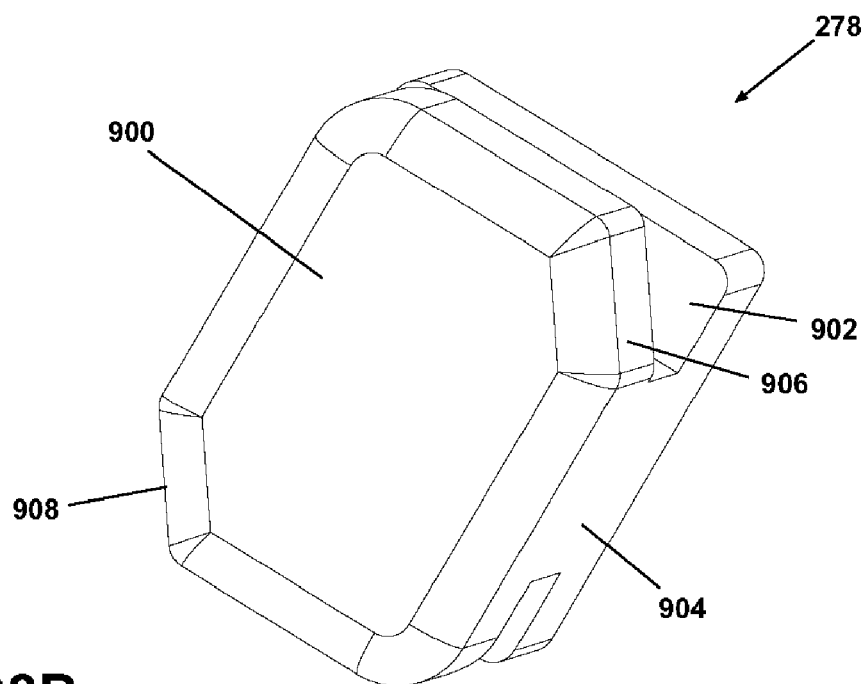

As illustrated in FIGS. 38A-B, the cam block 278 is a generally rectilinear body comprising an upper block 900 and a lower block 902 interconnected by a center beam 904. The upper block 900 is provided with a pair of diagonally juxtaposed inclined faces 906, 908 interrupting the rectilinear perimeter of the upper block 900. Laterally of the center beam 904 is a pair of parallel channelways 910, 912 separating the upper block 900 from the lower block 902. The cam block 278 is adapted for slidable receipt in the cam block retainer 280 with the beam 904 received in the gap 772 and the upper block 900 supported dorsally of the inner flange 768 and the outer flange 770.

Referring now to FIGS. 39A-D, the firing cage 290 is an elongated member having a proximal end 920 and a distal end 922 joined by a center portion 924. The center portion 924 comprises a pair of parallel, spaced-apart side rails 926, 928 having a semicircular cross-section and extending ventrally between a distal end wall 930 and a proximal end wall 932. The side rails 926, 928 defined a semicylindrical, upwardly-opening channelway 948 between the distal end wall 930 and the proximal end wall 932. Each rail 926, 928 is inset with an upwardly opening center notch 934, 936, respectively, intermediate the end walls 930, 932, and an upwardly-opening end notch 938, 940, respectively, adjacent the end wall 930. The spacing of the rails 926, 928 defines a slot 950 extending longitudinally between the end walls 930, 932. The proximal end of the slot 950 expands laterally to define a rectilinear expanded slot 954.

Figure 39A:
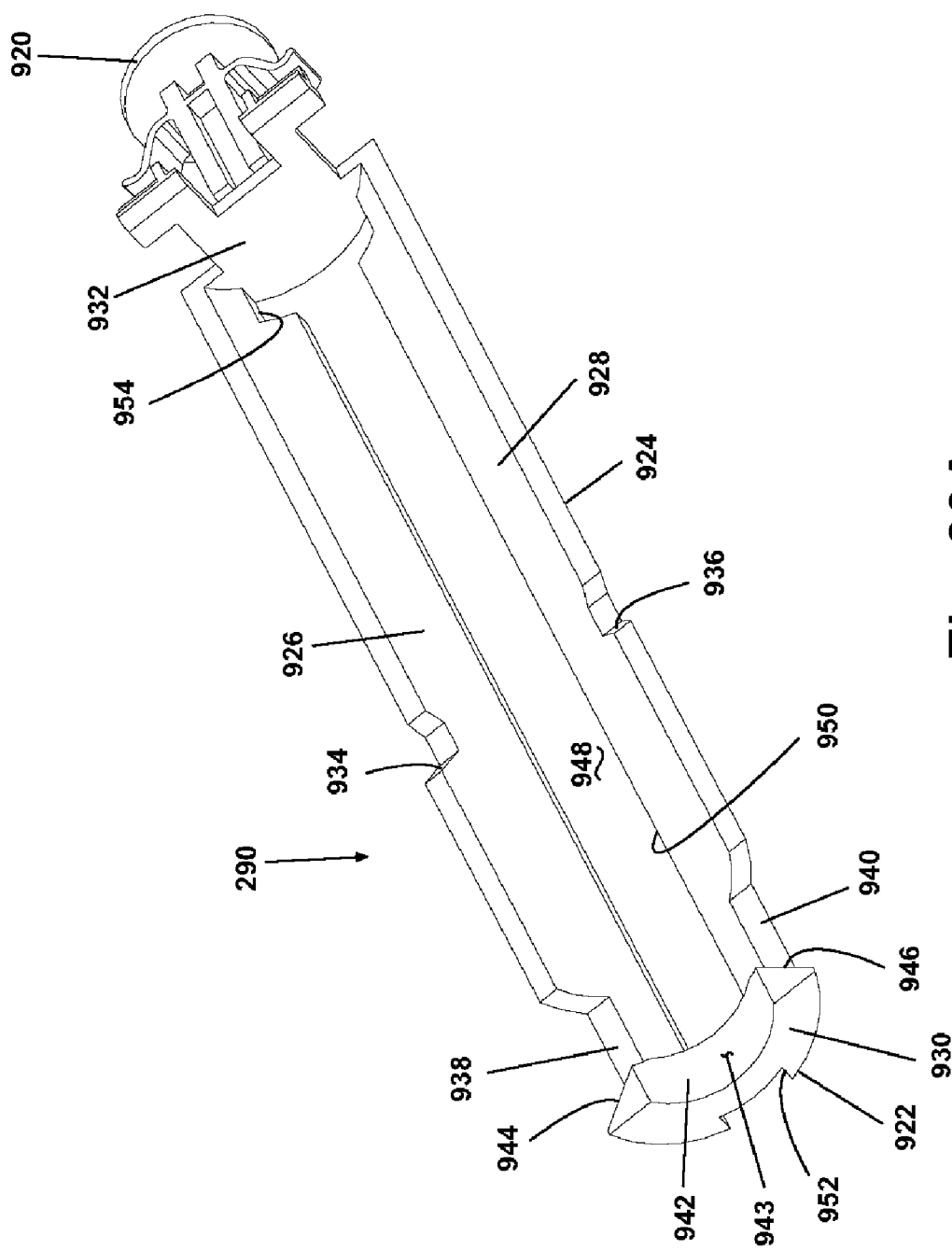
FIGS. 39A-D are perspective and enlarged partial views of a firing cage comprising an element of the trigger assembly illustrated in FIG. 24.
Figure 39B:
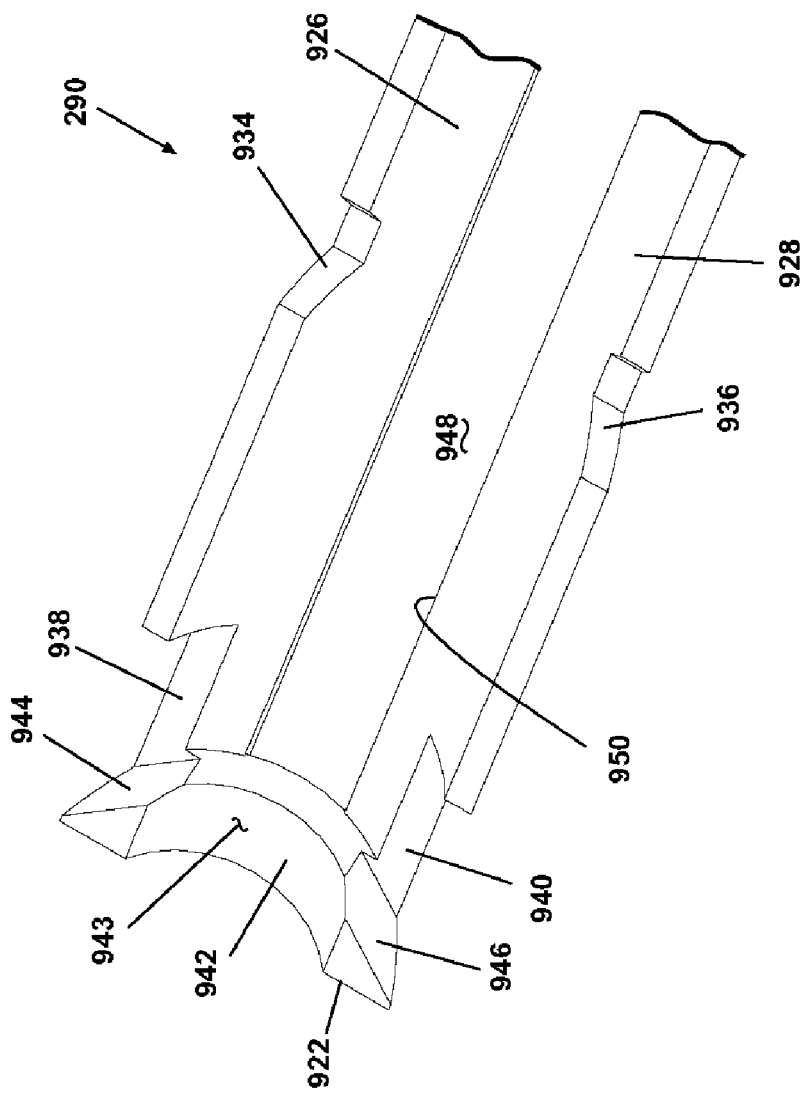
Figure 39C:
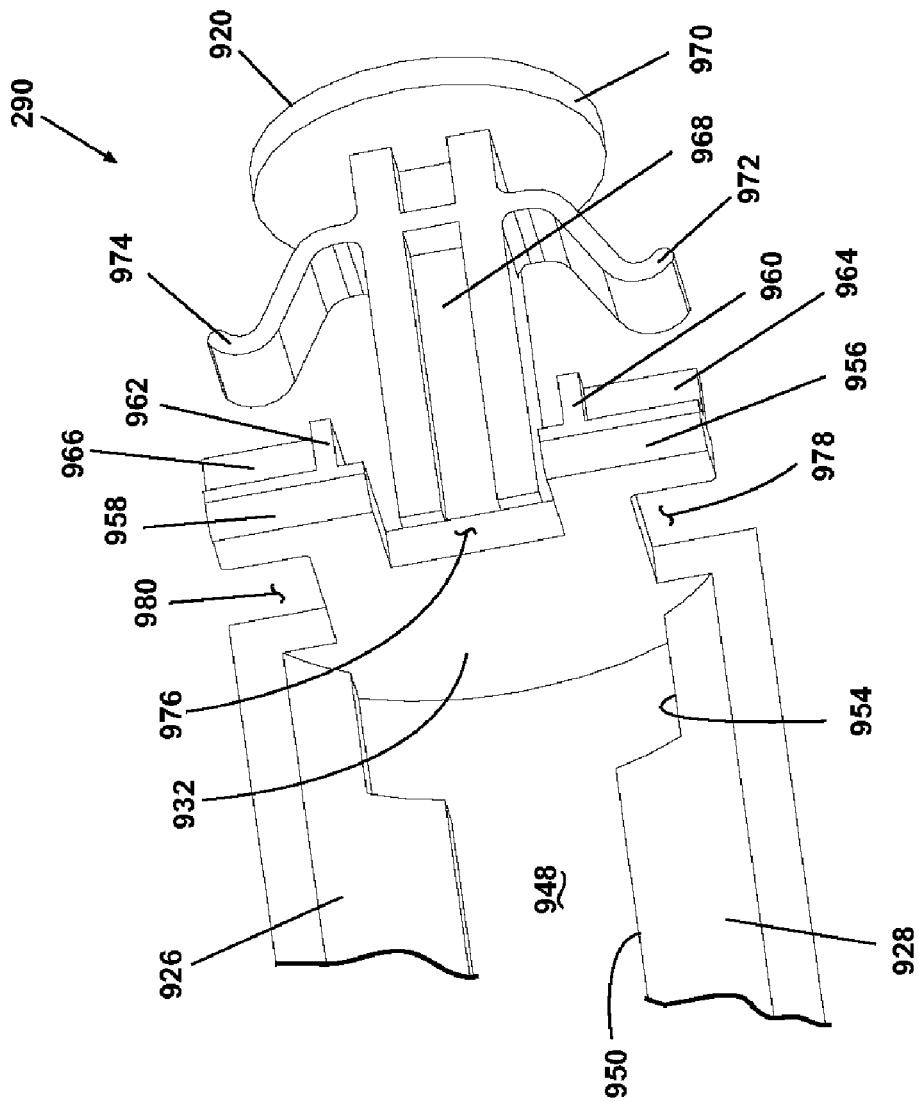
Figure 39D:
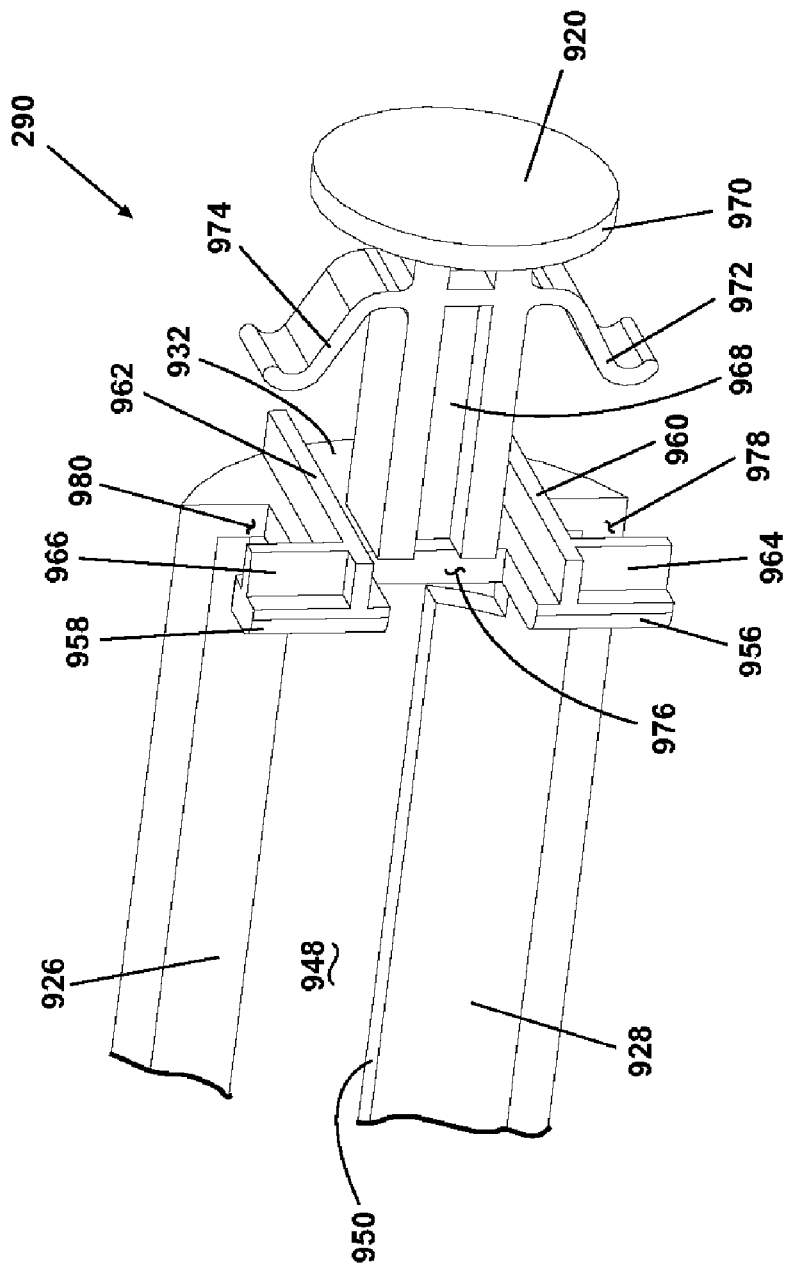

Referring to FIG. 39B, the distal end wall 930 is a somewhat arch-shaped body extending orthogonally from the side rails 926, 928, and having an arcuate surface 942 opening dorsally to define a cradle opening 943. The distal end wall 930 is also provided with an end wall slot 952 extending therethrough coextensive with the slot 950. A pair of outwardly chamfered inclined faces 944, 946 abuts the ended notches 938, 940, respectively. Referring to FIG. 39C, the proximal end wall 932 is a somewhat T-shaped body inset with an upper notch 976 opening dorsally, and a pair of side notches 978, 980 opening laterally to define a pair of L-shaped flanges 956, 958, respectively, along a dorsal portion of the proximal end wall 934. Referring also to FIG. 39D, the proximal side of the proximal end wall 932 is provided with a pair of vertical braces 960, 962 and horizontal braces 964, 966 for strengthening the flanges 956, 958. Extending orthogonally away from the proximal side of the proximal end wall 932 is a somewhat I-beam shaped beam 968 terminating in a circular, plate-like plunger 970. Extending laterally from the beam 968 adjacent the plunger 970, parallel to the flanges 956, 958, is a pair of ogee-shaped spring arms 972, 974.

Figure 40A:
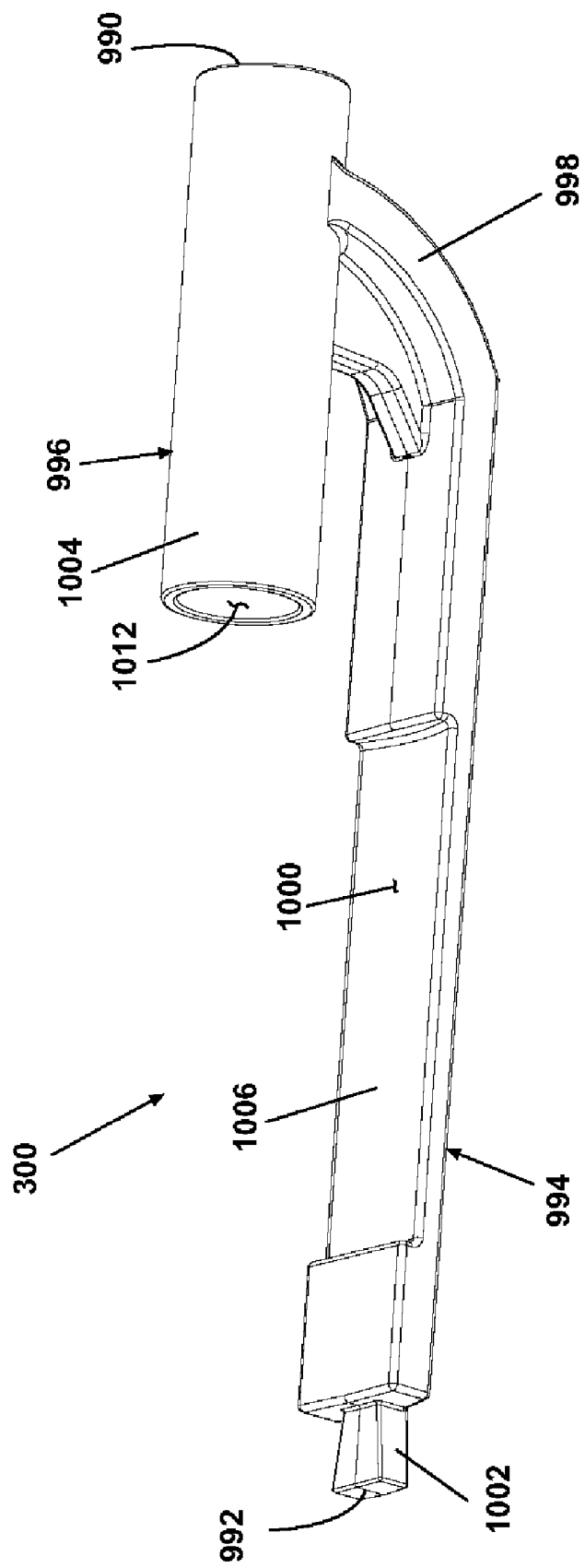
FIGS. 40A-C are perspective and enlarged partial views of a nosepiece comprising an element of the sample size control assembly illustrated in FIG. 24.
Figure 40B:
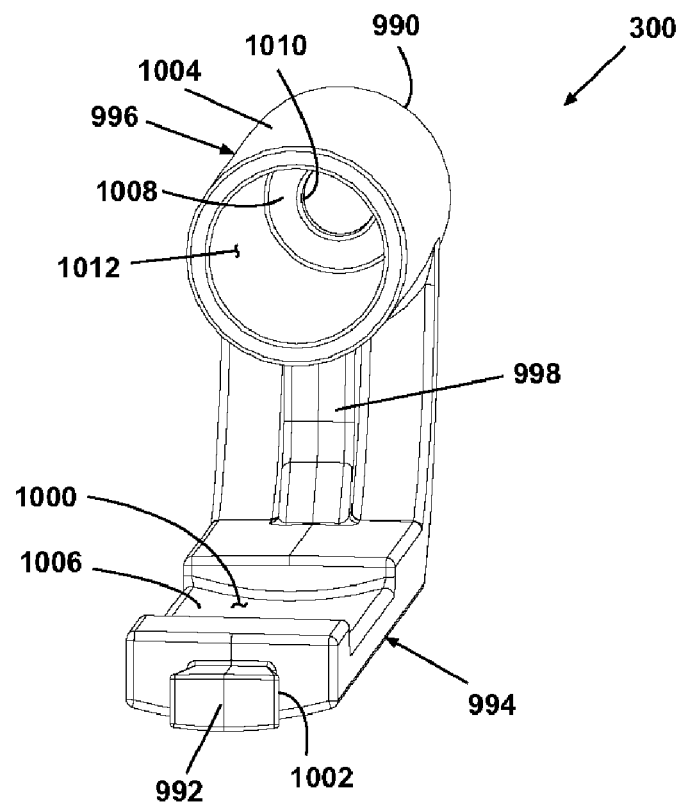
Figure 40C:
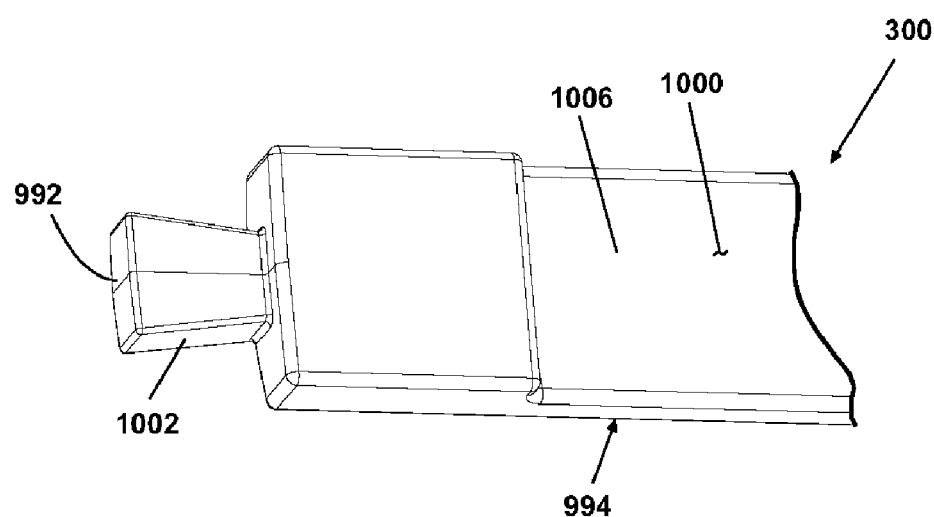

Referring now to FIGS. 40A-C, the nosepiece 300 is an elongated member having a distal end 990 and a proximal end 992, and comprising an elongated beam 994 interconnected in parallel, spaced-apart disposition with an elongated cylindrical collar 996 through a support member 998. The beam 994 is a generally strap-like member inset along an intermediate portion thereof with an upwardly-opening elongated mortise 1000 having an arcuate surface 1006, and terminating at the proximal end 992 in a dovetail 1002. The collar 996 comprises an annular wall 1004 terminating at the distal end 990 in a circular end wall 1008 having an aperture 1010 extending coaxially therethrough, and defining a cylindrical chamber 1012.

Figure 41A:
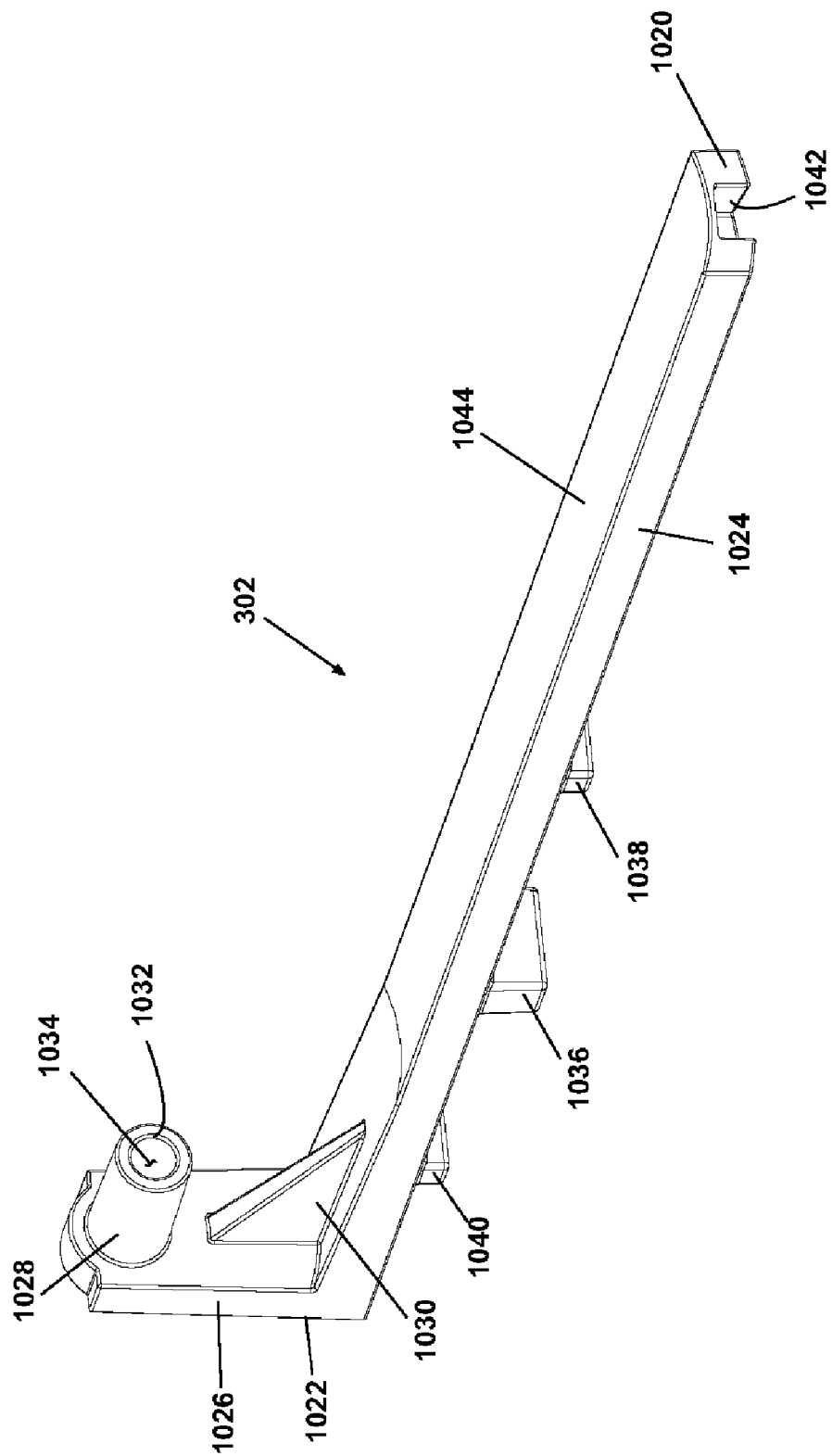
FIGS. 41A-B are perspective views of an adjustment member comprising an element of the sample size control assembly illustrated in FIG. 24.
Figure 41B:
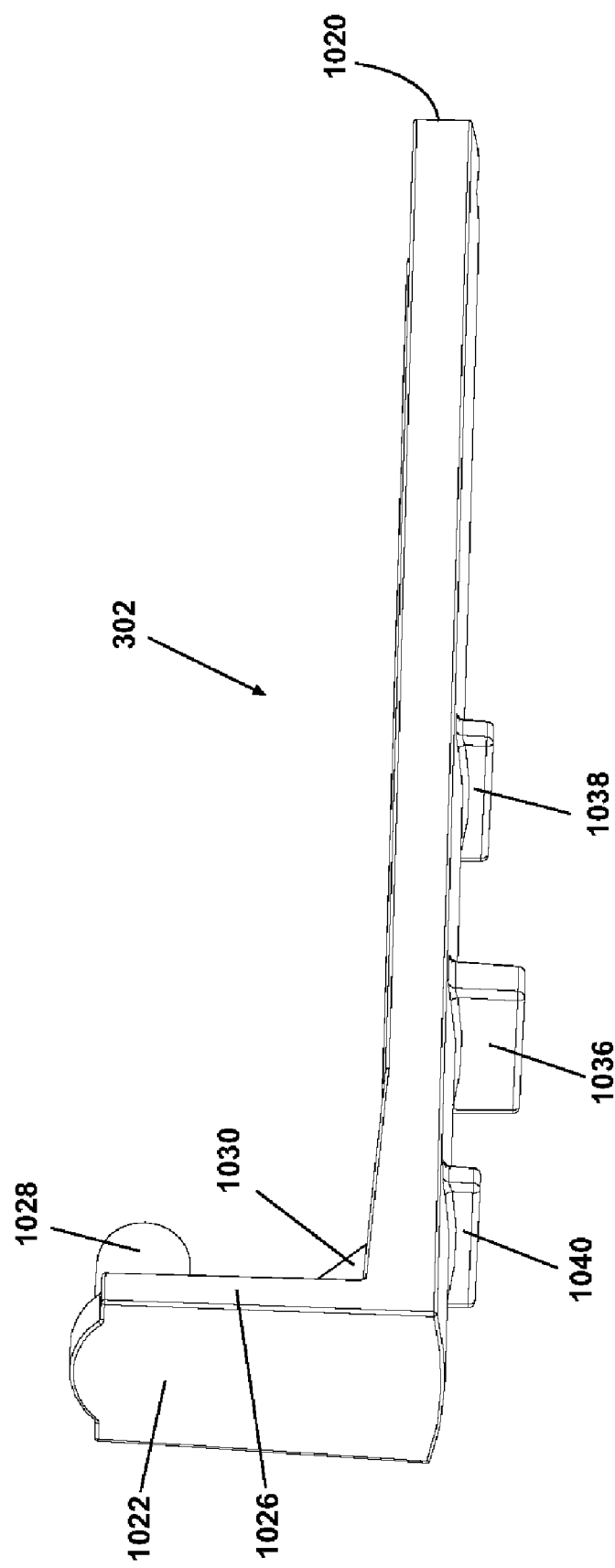

Referring now to FIGS. 41A-B, the adjustment member 302 is an elongated member having a distal end 1020 and a proximal end 1022, and comprising an elongated beam 1024 terminating at the proximal end 1022 in an orthogonally-disposed end wall 1026. The beam 1024 is a generally strap-like member having a cross-section approximating the cross-section of the beam 994, and a dorsal arcuate surface 1044 along its full length. The distal end 1020 is provided with a dovetail cutout 1042 adapted for slidable receipt of the dovetail 1002. The ventral surface of the beam 1024 is provided with a wall-like adjustment lever 1036 extending laterally across the beam 1024 orthogonal to the ventral surface. A wall-like forward stop 1038 extends laterally across the beam 1024 orthogonal to the ventral surface and parallel to the adjustment lever 1036, distally thereof. A wall-like rearward stop 1040 extends laterally across the beam 1024 orthogonal to the ventral surface and parallel to the adjustment lever 1036, proximally thereof.

The end wall 1026 terminates at a dorsal end in a cylindrical stylet seat 1028 comprising an annular wall 1032 defining a cylindrical chamber 1034 opening away from the end wall 1026 toward the distal end 1020. The chamber 1034 is adapted for slidable receipt of the proximal end of the stylet 20 therein. A triangular brace 1030 extends between the end wall 1026 and the beam 1024.

Figure 42:
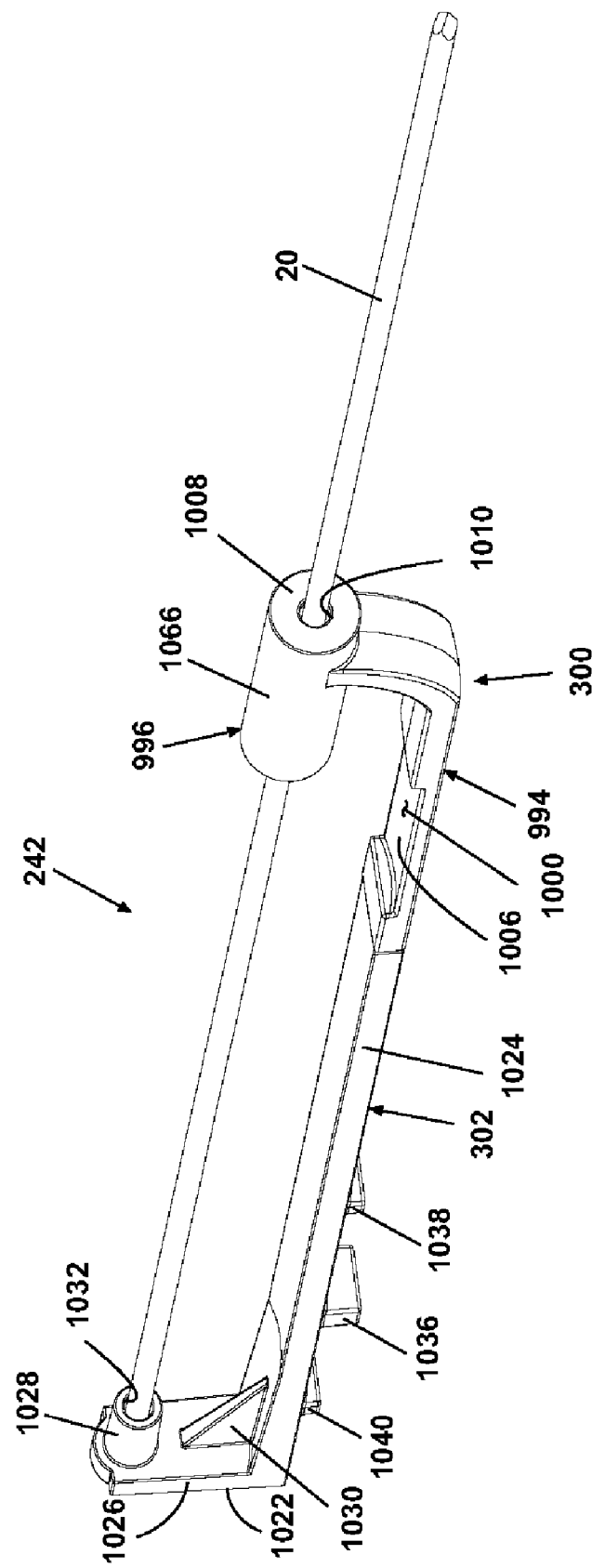
FIG. 42 is a perspective view of the sample size control assembly illustrated in FIG. 24.

As illustrated in FIG. 42, the nosepiece 300 is joined to the adjustment member 302 by insertion of the dovetail 1002 into the dovetail cutout 1042 to form the sample size control assembly 142. The proximal end of the stylet 20 is held in the chamber 1034 so that the stylet 20 extends into the chamber 1012 and through the aperture 1010.

Figure 43A:
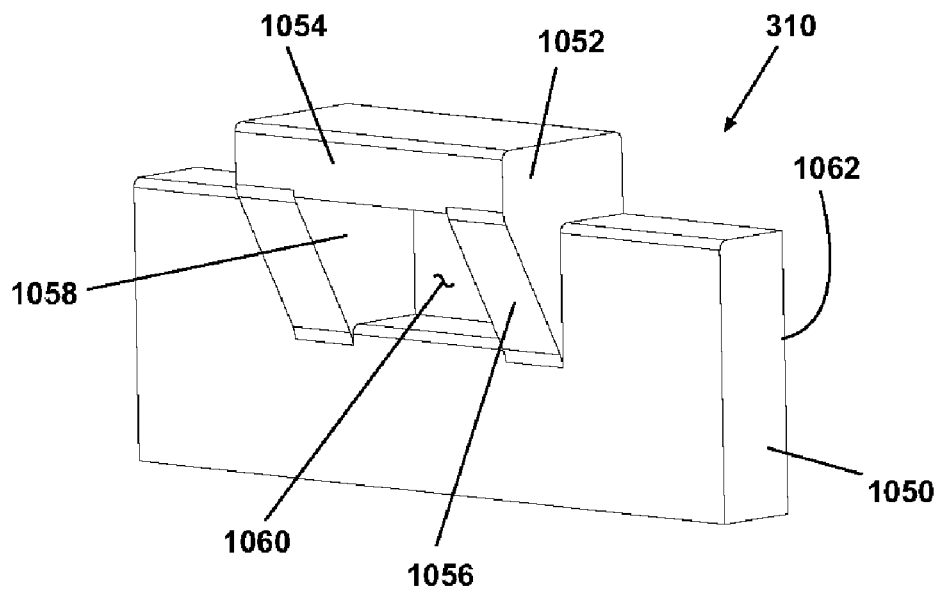
FIGS. 43A-B are perspective views of a latch plate comprising an element of the cannula operation assembly illustrated in FIG. 24.
Figure 43B:
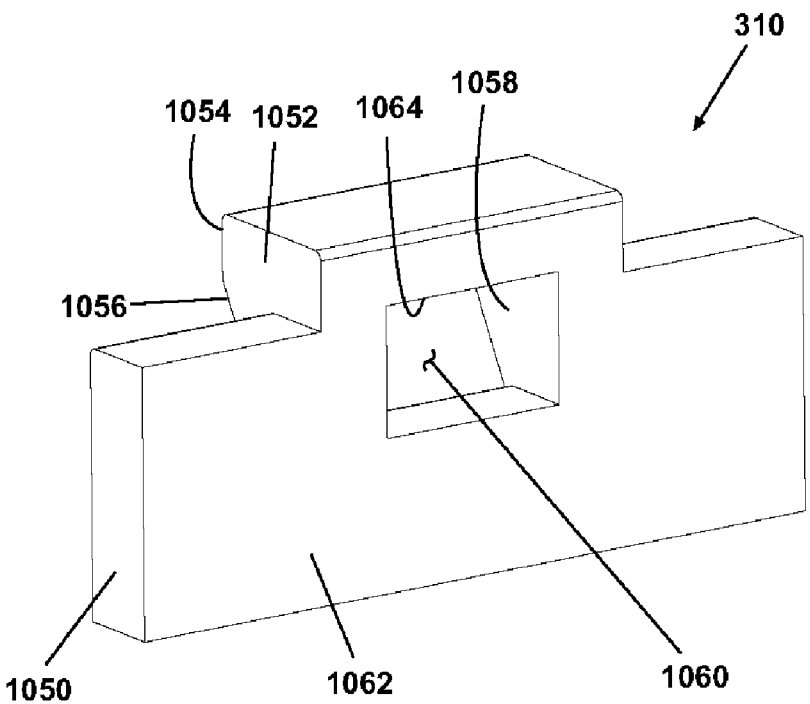

Referring now to FIGS. 43A-B, the latch plate 310 is a wall-like body comprising a plate portion 1050 and a crown portion 1052. The plate portion 1050 has a planar surface 1062 along a distal side thereof. The crown portion 1052 comprises a top wall 1054 disposed proximal and orthogonal to the plate portion 1050 and attached to the plate portion 1050 through a pair of triangular braces 1056, 1058 orthogonally intersecting the plate portion 1050 at an upper portion thereof to define a rectilinear opening 1060 therethrough. The top wall 1054 terminates in a top edge 1064 along an upper portion of the opening 1060.

Figure 44A:
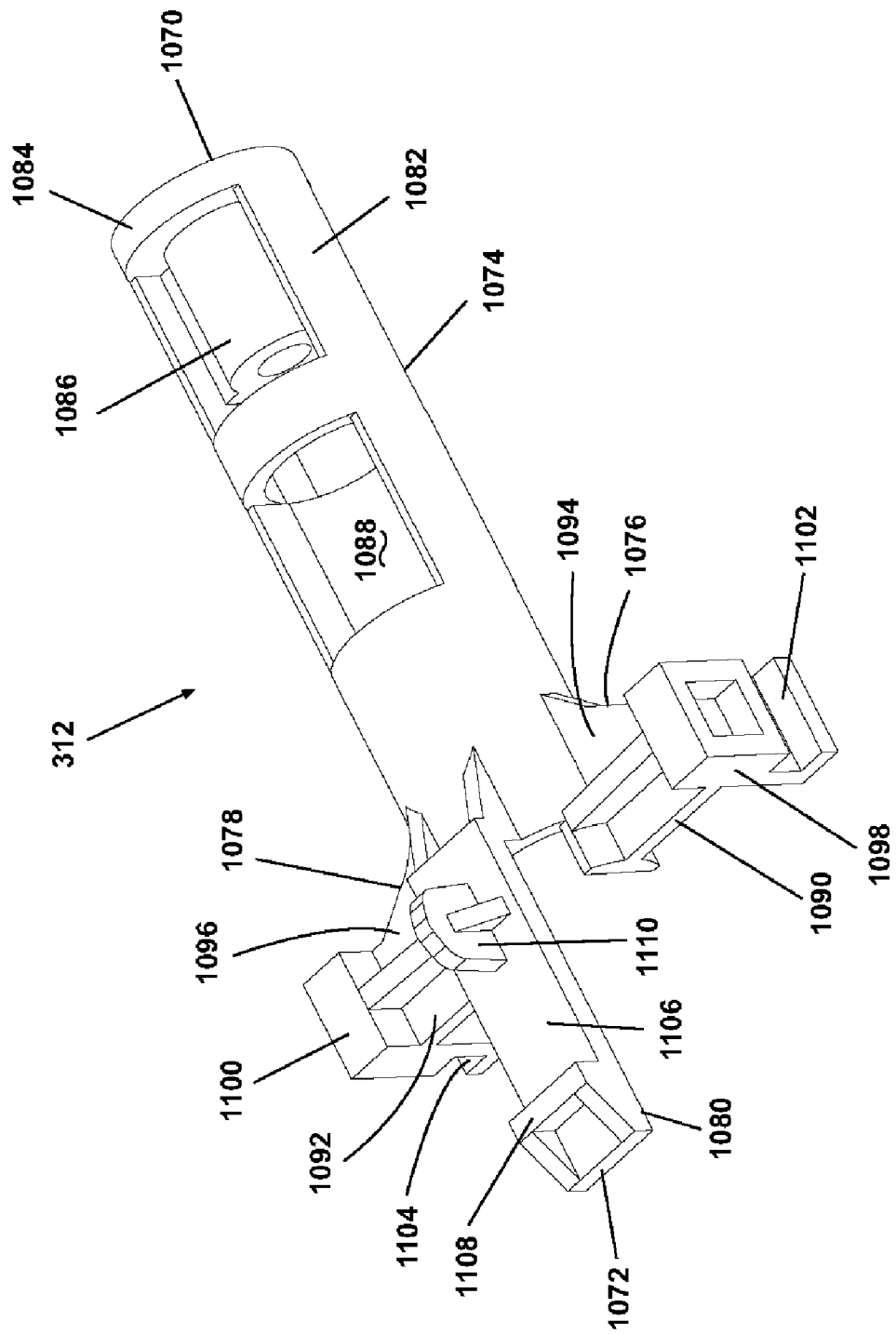
FIGS. 44A-C are perspective view of a spoon cannula carriage comprising an element of the cannula operation assembly illustrated in FIG. 24.
Figure 44B:
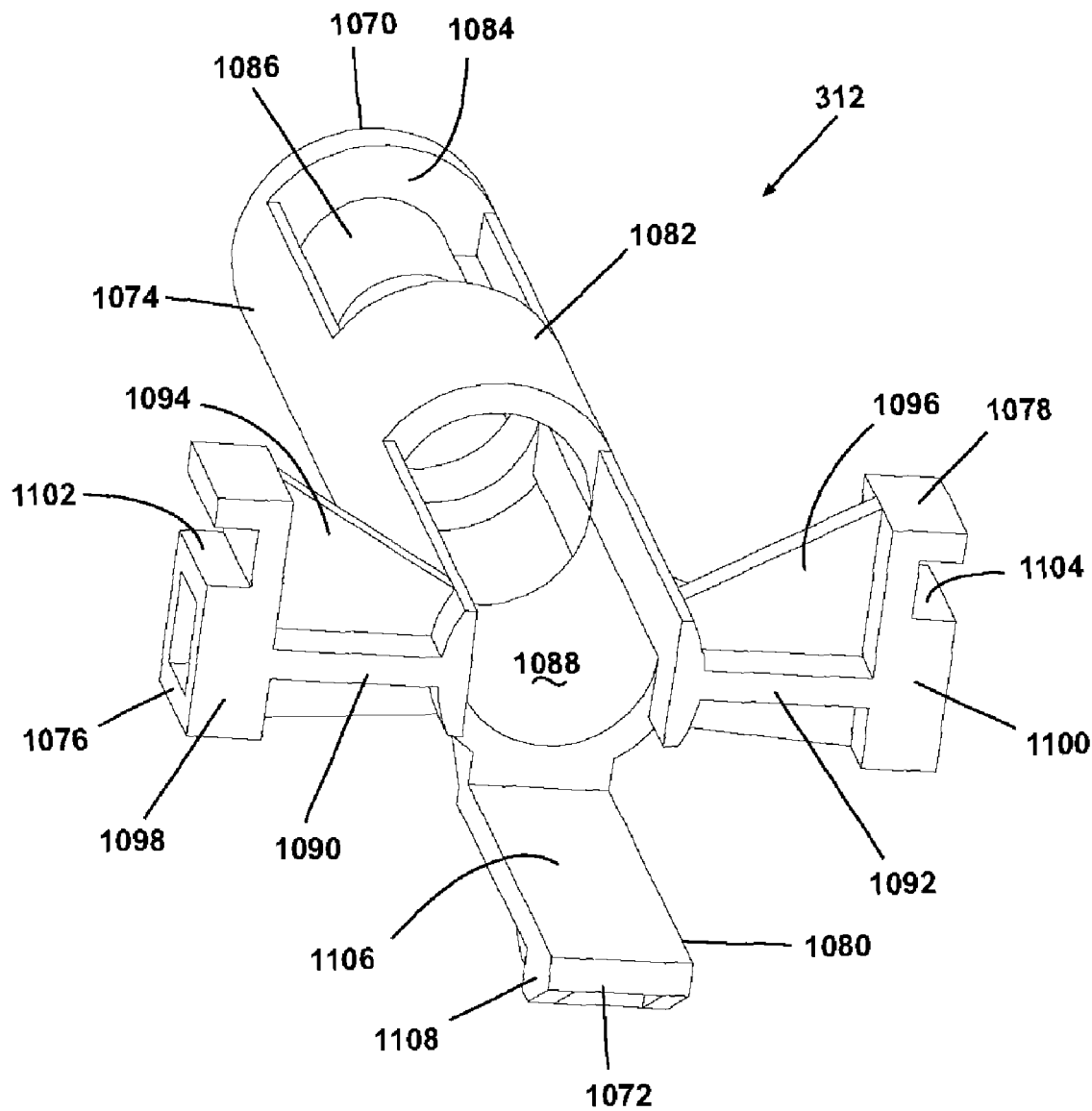
Figure 44C:
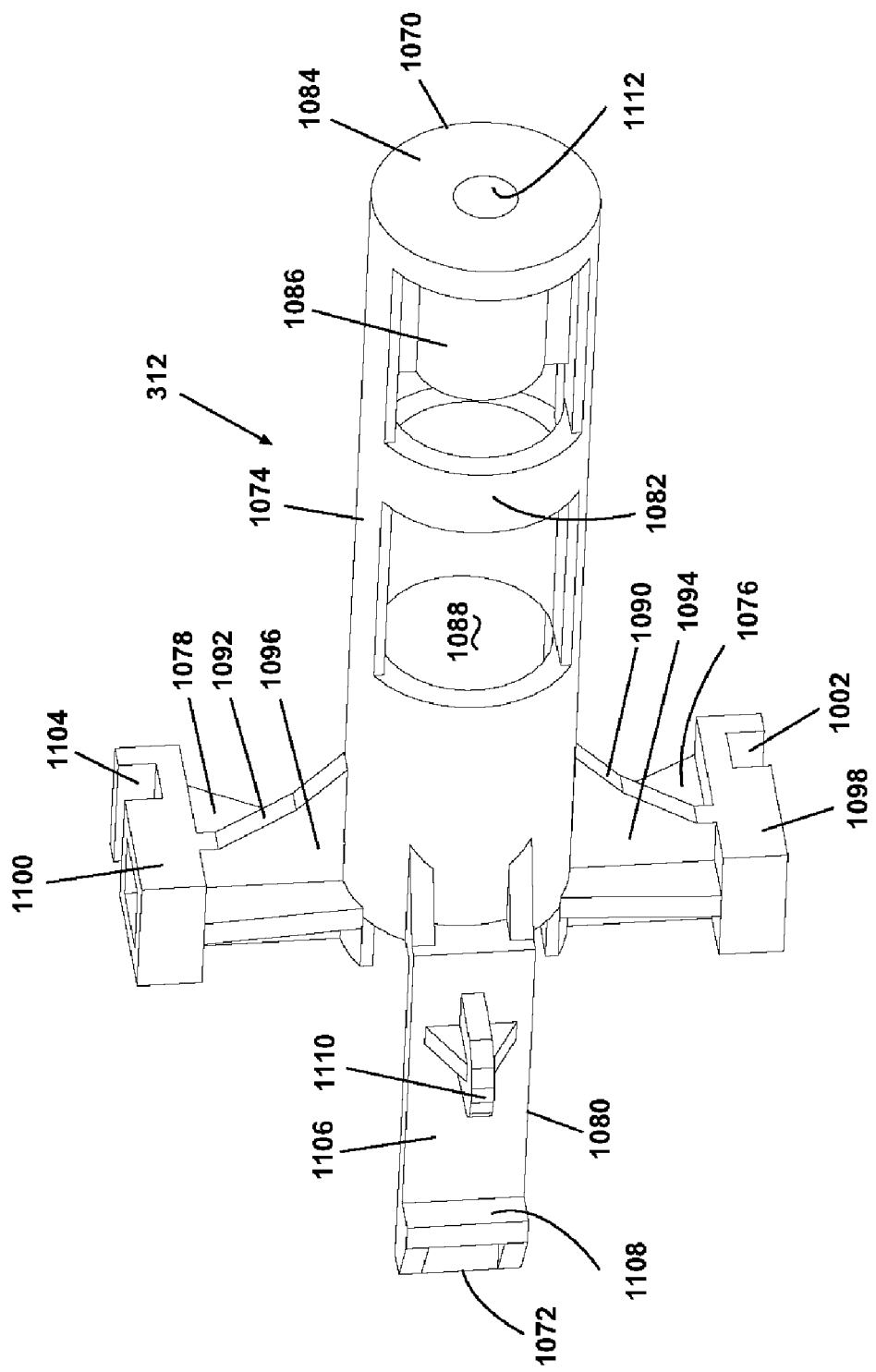

As illustrated in FIGS. 44A-C, the spoon cannula carriage 312 has a distal end 1070 and a proximal end 1072, and comprises a barrel portion 1074, a pair of wing portions 1076, 1078, and a hook portion 1080. The barrel portion 1074 is an elongated, cylindrically-shaped body comprising an annular wall 1082 terminating at the distal end 1070 and a circular end wall 1084. The annular wall 1082 and the end wall 1084 define a cylindrical barrel chamber 1088. Extending orthogonally from the end wall 1084 into the barrel chamber 1088 is a cylindrical spoon cannula seat 1086 having a circular aperture 1112 extending coaxially through the spoon cannula seat 1086 and the end wall 1084.

Each wing portion 1076, 1078 comprises a beam 1090, 1092, respectively, extending diametrically outwardly from a proximal end of the barrel portion 1074. Each beam 1090, 1092 is provided with a triangular brace 1094, 1096, respectively, extending distally of the beam 1090, 1092 to join the barrel portion 1074. Each brace 1094, 1096 terminates in a rectilinear end bearing 1098, 1100, respectively, having an elongated, rectilinear end slot 1102, 1104, respectively, at a lower portion thereof parallel to the longitudinal axis of the barrel portion 1074.

The hook portion 1080 comprises an elongated member extending longitudinally away from a proximal end of the barrel portion 1074, disposed 90° from each wing portion 1076, 1078 parallel to the longitudinal axis of the barrel portion 1074. The hook portion 1080 comprises a strap-like resilient arm 1106 attached to the barrel portion 1074 in cantilevered fashion, terminating in an upwardly-disposed hook 1108. Extending from the resilient arm 1106 adjacent the connection of the arm 1106 with the barrel portion 1074 is an upwardly-disposed, plate-like fin 1110 aligned with the longitudinal axis of the barrel portion 1074. The barrel portion 1074 is adapted for slidable registry with the cradle opening 835 of the shuttle 170, and the braces 1094, 1096 are adapted for slidable receipt in the notches 838 of the wings 832, 834.

Figure 45:
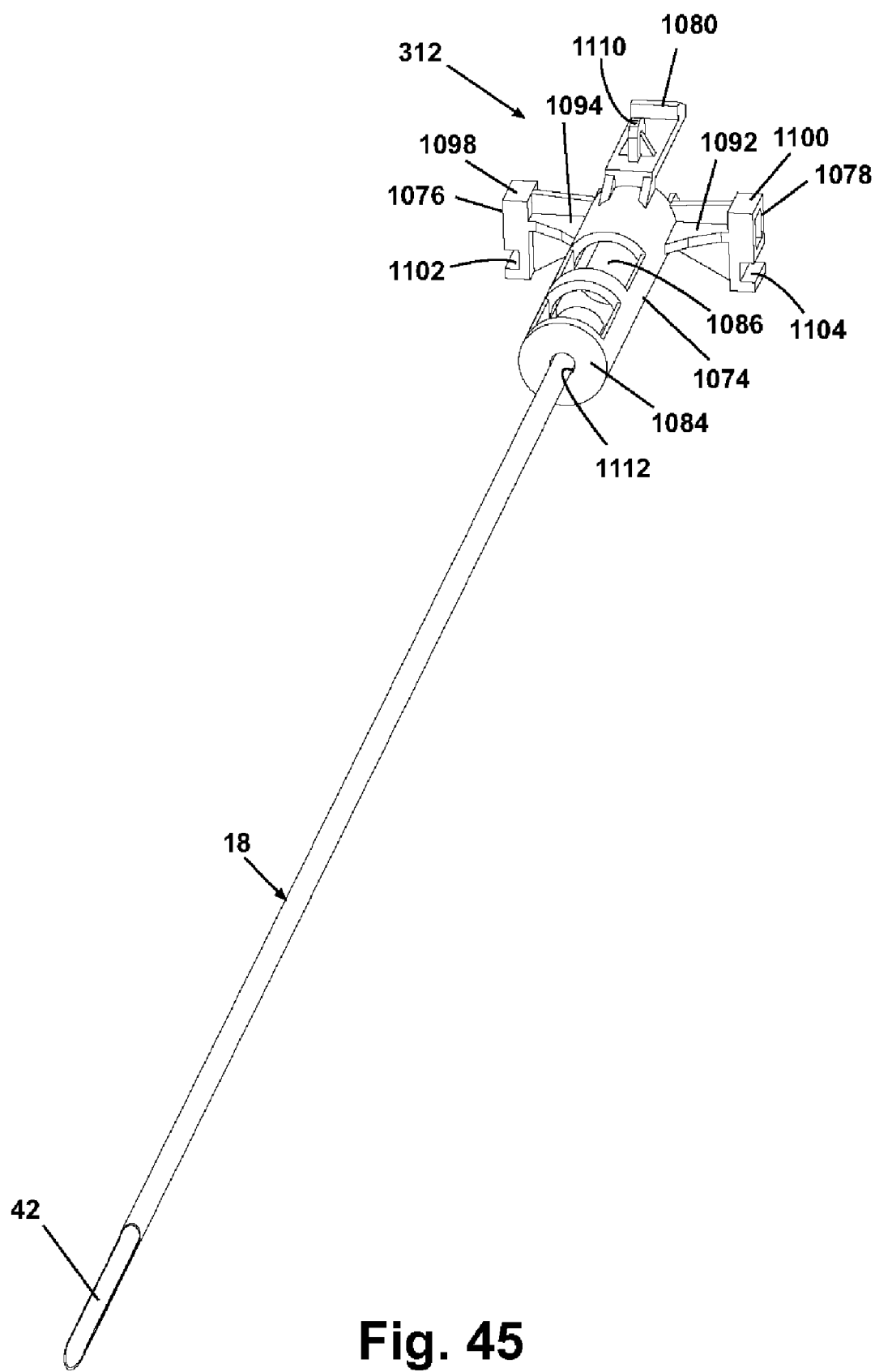
FIG. 45 is a perspective view of the spoon cannula carriage of FIGS. 44A-C with the spoon cannula affixed thereto.
Figure 46A:
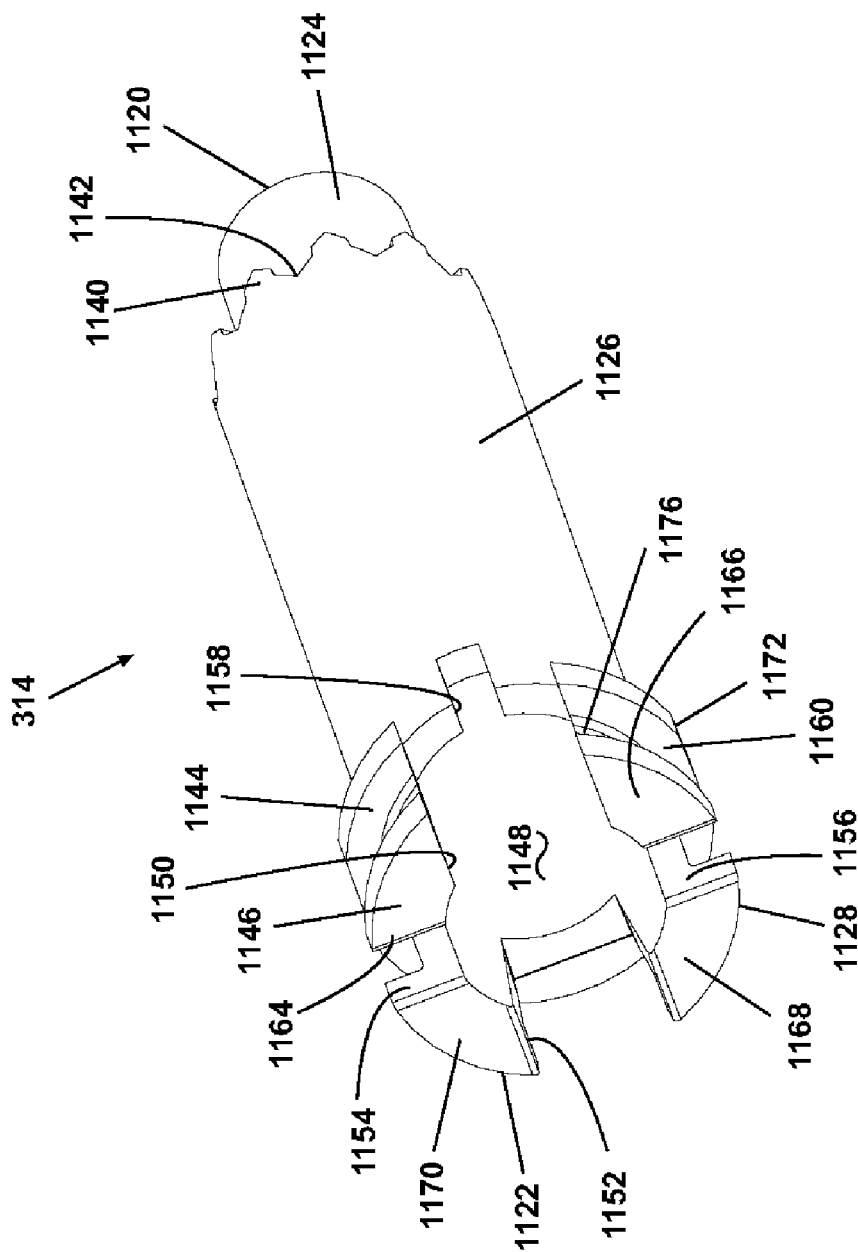
FIGS. 46A-D are perspective and enlarged partial views of a cutting cannula carriage comprising an element of the cannula operation assembly illustrated in FIG. 24.
Figure 46B:
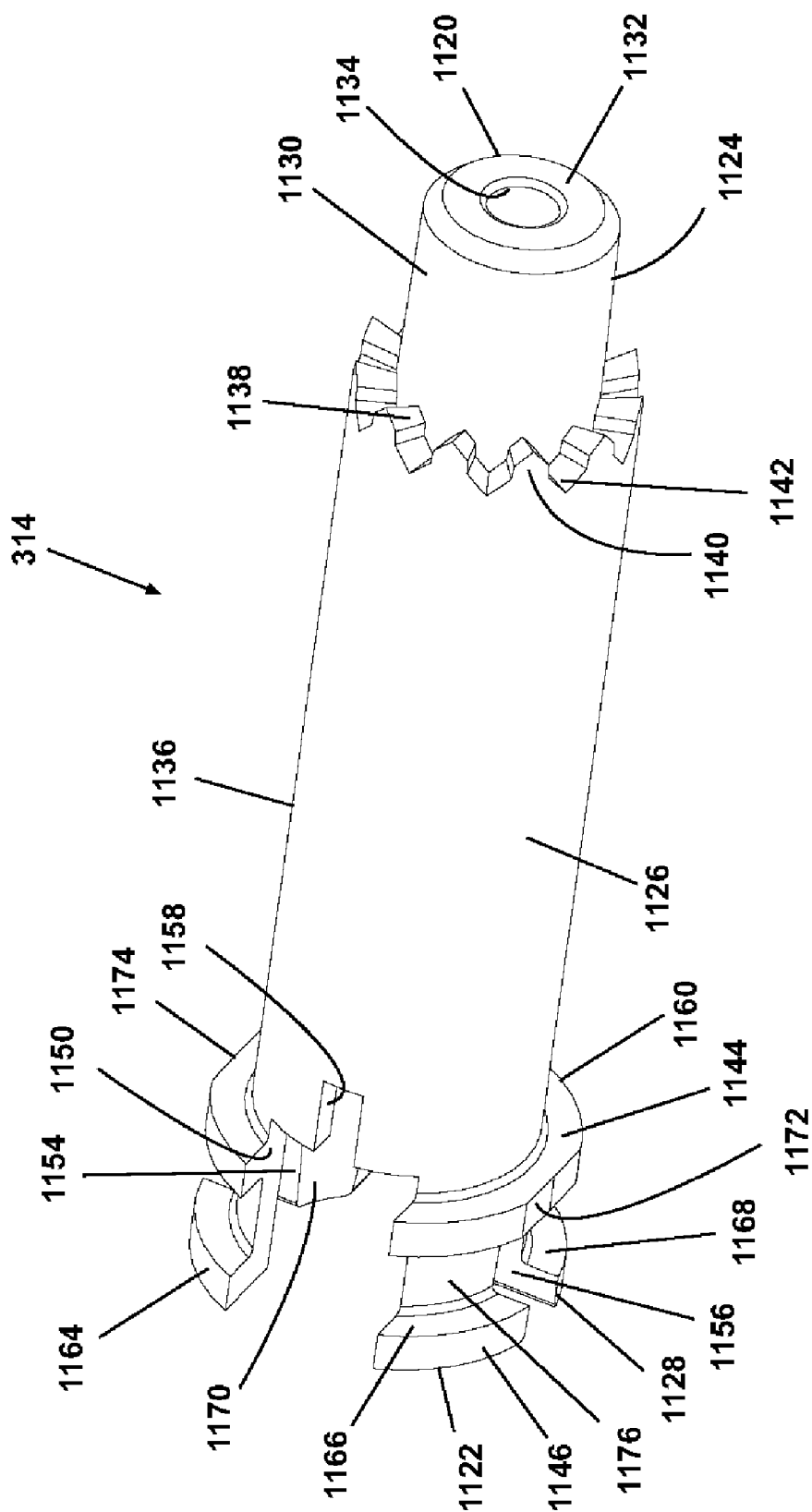
Figure 46C:
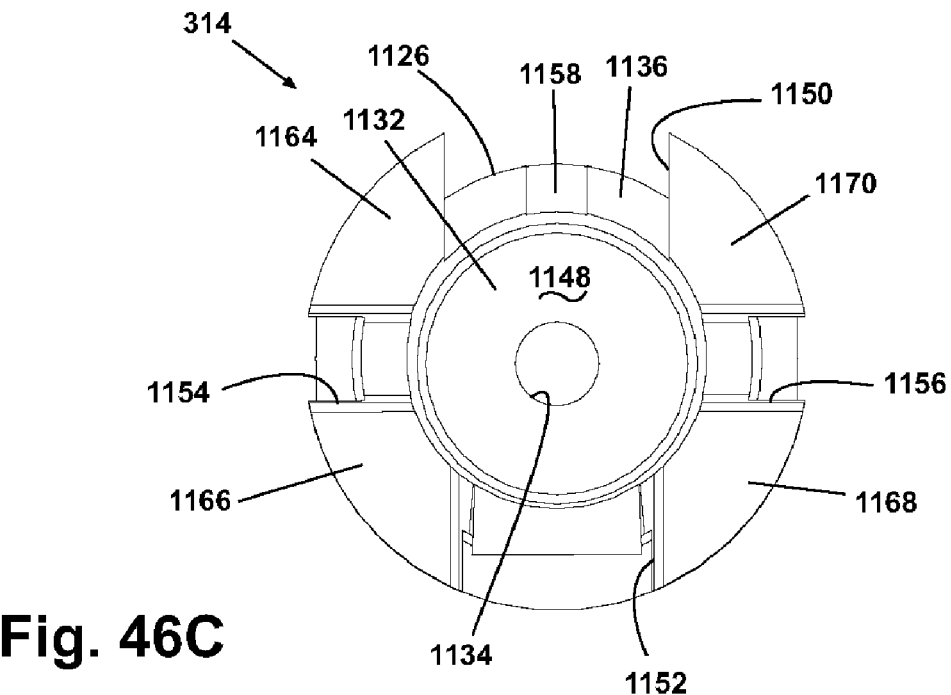
Figure 46D:
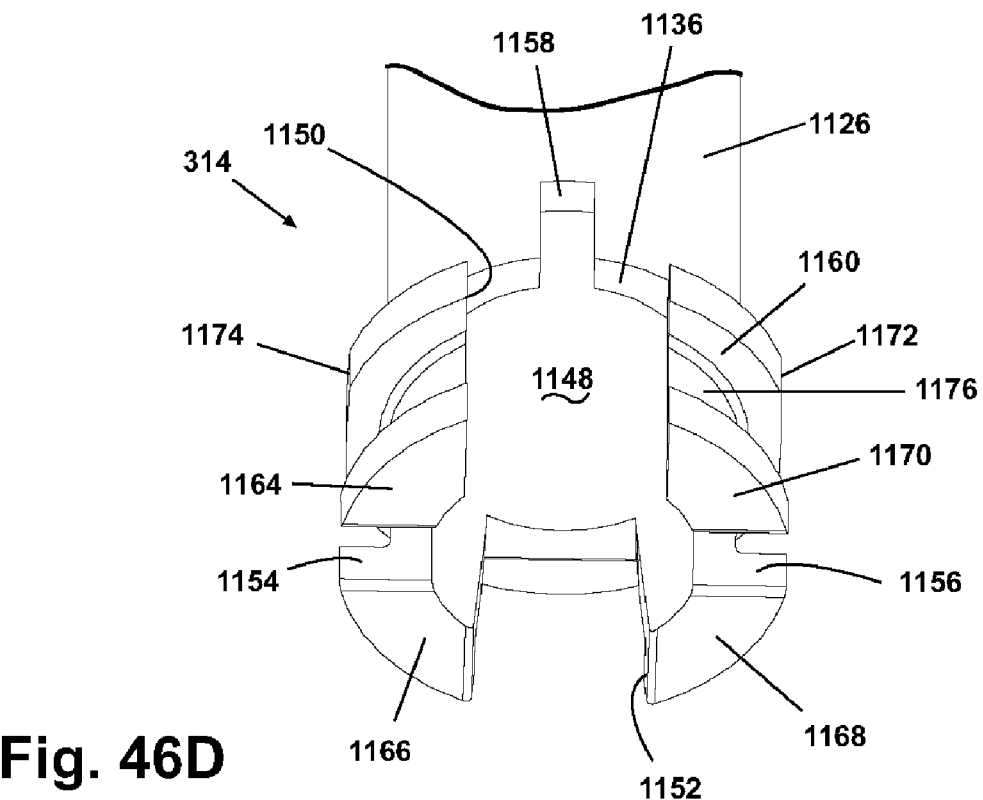

As illustrated in FIG. 45, a proximal end of the spoon cannula 18 is received in the aperture 1112 for fixed attachment to the spoon cannula seat 1086 to extend distally away from the end wall 1084. The spoon cannula 18 is oriented in the spoon cannula seat 1086 so that the spoon section 42 opens dorsally in longitudinal alignment with the fin 1110.

As illustrated in FIGS. 46A-D, the cutting cannula carriage 314 is an elongated, generally cylindrically-shaped body having a distal end 1120 and a proximal end 1122, and comprising a nose portion 1124 at the distal end 1120, a flange portion 1128 at the proximal end 1122, and a barrel portion 1126 intermediate the nose portion 1124 and the flange portion 1128. The nose portion 1124 comprises an annular wall 1130 terminating at the distal end in a circular end wall 1132 having an aperture 1134 coaxially extending therethrough. The barrel portion 1126 comprises an annular wall 1136 having a diameter somewhat greater than the diameter of the annular wall 1130.

The annular wall 1136 terminates at its intersection with the nose portion 1124 in a circumferential toothed edge 1138 comprising a radial array of alternating projections 1140 and cavities 1142, which effectively form a gear. The annular wall 1136 transitions at the proximal end 1122 to a circumferential inner flange 1144 extending radially away from the annular wall 1136. The inner flange 1144 transitions through a neck portion 1176 having a diameter equal to the diameter of the annular wall 1136 to a circumferential outer flange 1146 extending radially away from the neck portion 1176 in parallel, spaced disposition with the inner flange 1144.

The outer flange 1146, the annular wall 1136, and the inner flange 1144 are interrupted by a primary notch 1150 inset in the annular wall 1136 from the proximal end 1122. A narrow barrel notch 1158 is inset longitudinally from the primary notch 1150 into the annular wall 1136 toward the distal end 1120. The inner flange 1144 is provided with a pair of planar faces 1172, 1174 along the circumferential face thereof spaced 90° from the primary notch 1150. The outer flange 1146 is interrupted by a primary notch 1152 in diametrically-opposed disposition with the primary notch 1150, and a pair of secondary notches 1154, 1156 in diametrically-opposed disposition and offset 90° from the primary notches 1150, 1152. The notches 1150-1156 divide the outer flange 1146 into equal area sector pieces 1164, 1166, 1168, 1170. The outer flange 1146, the inner flange 1144, the neck portion 1176, the annular wall 1136, and the annular wall 1130 define a cylindrical chamber 1148 extending from the proximal end 1122 to the aperture 1134. The aperture 1134 is adapted for fixed insertion of the coring cannula 16 so that the coring cannula 16 extends distally from the distal end 1120. The coring cannula 16 is oriented relative to the cutting cannula carriage 314 so that the excising finger 70 is longitudinally aligned with the barrel notch 1158.

Figure 47A:
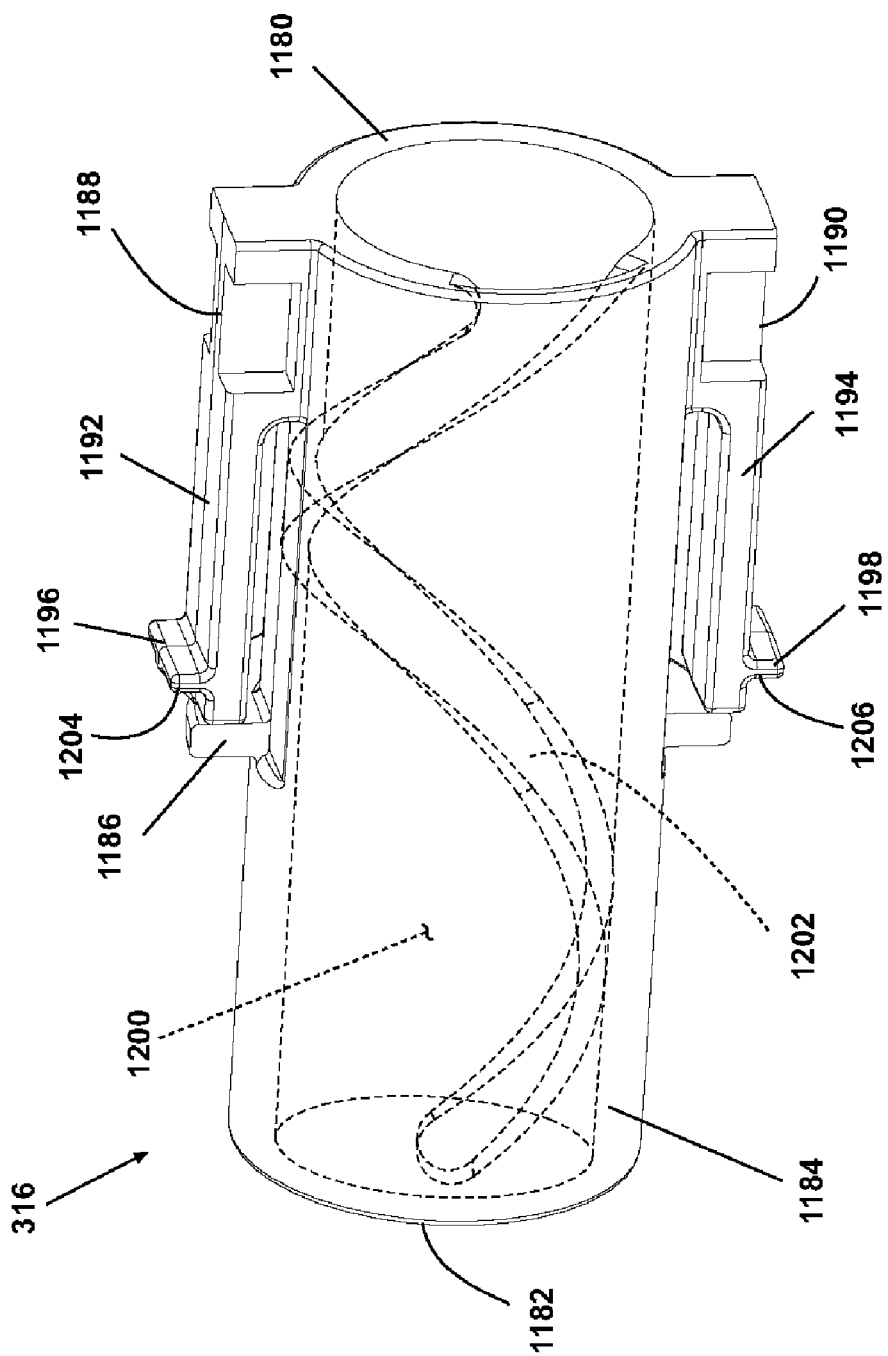
FIGS. 47A-C are perspective views of a helical drive member comprising an element of the cannula operation assembly illustrated in FIG. 24.
Figure 47B:
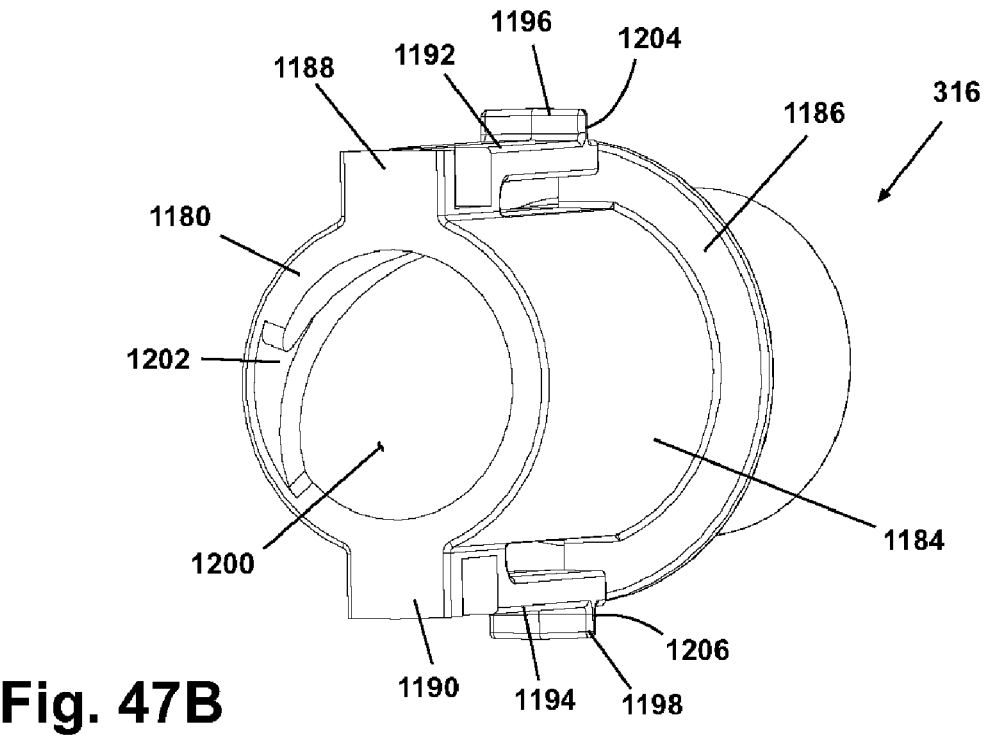
Figure 47C:
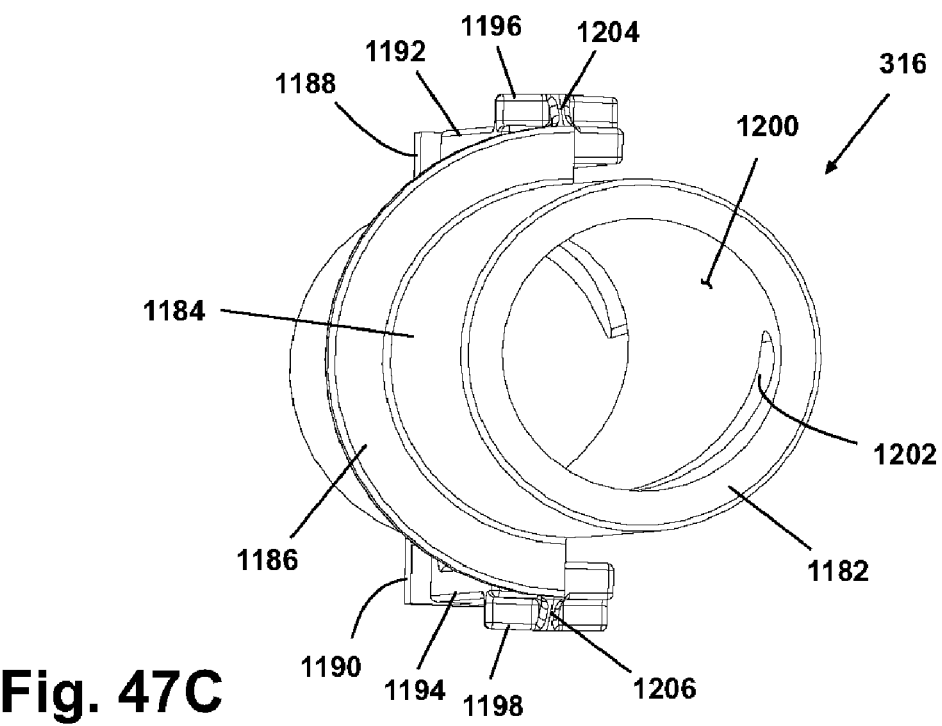

Referring now to FIGS. 47A-C, the helical drive member 316 is an elongated, generally annular body having a distal end 1180 and a proximal end 1182, and comprising an annular wall 1184 defining a cylindrical chamber 1200 open at both ends 1180, 1182. A helical channelway 1202 extends along the interior of the annular wall 1184 from the distal end 1180 to the proximal end 1182. A semicircular rib 1186 extends radially along an outer surface of the annular wall 1184 at approximately the mid-section of the annular wall 1184. A pair of diametrically-opposed resilient arms 1192, 1194 extends longitudinally along the outer surface of the annular wall 1184 from the distal end 1180 toward the proximal end 1182. The resilient arms 1192, 1194 are attached in cantilevered fashion to the annular wall 1184 through a pair of diametrically-opposed mounting blocks 1188, 1190 at the distal end 1180. The resilient arms 1192, 1194 terminate in a pair of radially outwardly-extending hooks 1196, 1198, respectively. An inclined brace 1204, 1206 extends from the resilient arm 1192, 1194, respectively, to the proximal face of the hook 1196, 1198, respectively.

Figure 48A:
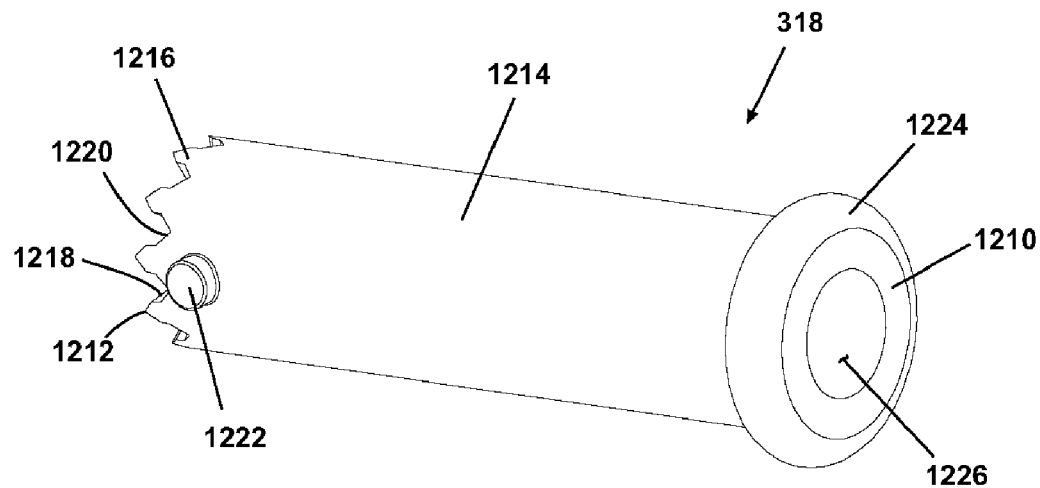
FIGS. 48A-B are perspective views of a rotating driven member comprising an element of the cannula operation assembly illustrated in FIG. 24.
Figure 48B:
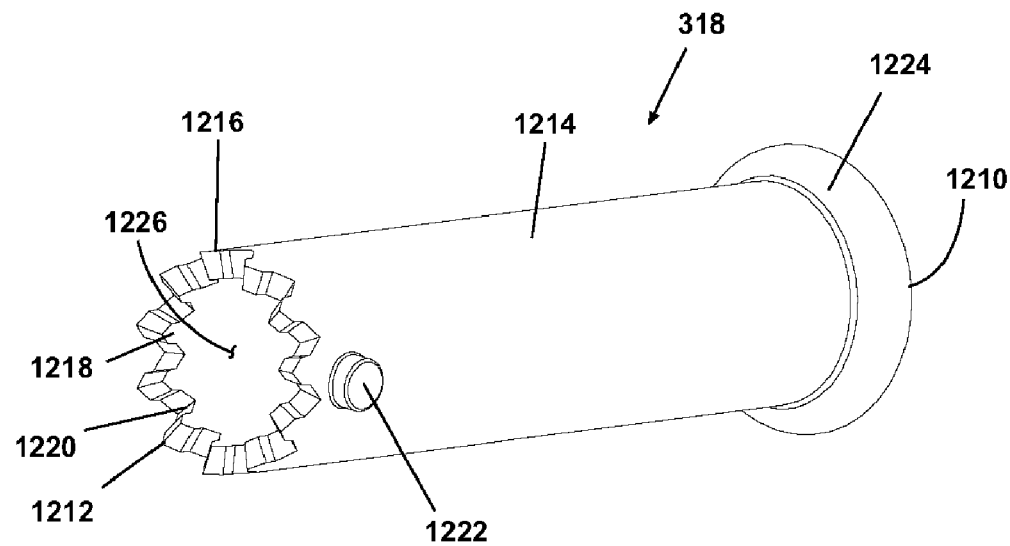

Referring now to FIGS. 48A-B, the rotating driven member 318 is an elongated, generally annular body having a distal end 1210 and a proximal end 1212, and comprising an annular wall 1214 defining a cylindrical aperture 1226 extending between both ends 1210, 1212. The annular wall 1214 terminates at the proximal end 1212 in a circumferential toothed edge 1216 comprising a radial array of alternating projections 1218 and cavities 1220 that effectively form a gear that can mesh with the gear on the cutting cannula carriage 314. The projections 1218 are adapted for cooperative registry with the cavities 1142 of the cutting cannula carriage 314, and the cavities 1220 are adapted for cooperative registry with the projections 1140 of the cutting cannula carriage 314.

The annular wall 1214 transitions at the distal end 1210 to a circular flange 1224 having a diameter somewhat greater than the diameter of the annular wall 1214. A cylindrical boss 1222 extends radially away from the annular wall 1214 adjacent the proximal end 1212, and is adapted for slidable registry with the helical channelway 1202. The annular wall 1214 is adapted for slidable insertion in the chamber 1200 of the helical drive member 316, with the boss 1222 received in the channelway 1202. The aperture 1226 at the proximal end 1212 is adapted to receive the nose portion 1124 of the cutting cannula carriage 314, and the aperture 1226 at the distal end 1210 is adapted to receive the collar 996 of the nosepiece 300.

The assembled biopsy gun 220 will now be described with reference to the Figures, and particularly to FIGS. 25 and 49. The rotating driven member 318 is received in the helical drive member 316 by inserting the proximal end 1212 in the distal end of the chamber 1200 with the boss 1222 received in the helical channelway 1202. The cutting cannula carriage 314, with the coring cannula 16 affixed thereto, is installed in the helical drive member 316 by inserting the distal end 1120 in the proximal end of the chamber 1200 for cooperative registry of the toothed edge 1138 of the cutting cannula carriage 314 with the toothed edge 1216 of the rotating driven member 318. The cutting cannula carriage 314 and the coring cannula 16 are oriented so that the excising finger 70 is to the ventral side of the biopsy gun 220 and the barrel notch 1158 is to the ventral side of the cutting cannula carriage 314. The semicircular rib 1186 is oriented to the dorsal side of the helical drive member 316. A helical spring 320 encircles the proximal end 1182 of the helical drive member 316 to bear against the semicircular rib 1186 and extend away from the proximal end 1182.

The spoon cannula carriage 312, with the spool cannula 18 affixed thereto, is received in the cutting cannula carriage 314 by inserting the distal end 1070 into the proximal end 1122 of the chamber 1148 with the spoon cannula 18 inserted through the coring cannula 16. The helical spring 304 is inserted into the barrel chamber 1088 of the spoon cannula carriage 312 and retained by the spoon cannula seat 1086 to extend proximally away from the spoon cannula carriage 312. With the stylet 20 seated in the stylet seat 1028 of the adjustment member 302, the assembled spoon cannula carriage 312, cutting cannula carriage 314, helical drive member 316, and rotating driven member 318 are attached to the adjustment member 302 by inserting the stylet 20 through the spoon cannula 18. The proximal end of the helical spring 304 is retained around the stylet seat 1028, thereby urging the spoon cannula carriage 312 distally into engagement with the cutting cannula carriage 314. The adjustment member 302 is inserted into the slot 950 of the firing cage 290 so that the side rails 926, 928 and the beam 1024 of the adjustment member 302 are in longitudinal registry to form a curved, closed-bottom channel. The nosepiece 300 is then attached to the adjustment member 302 by inserting the cannula assembly 14 through the collar 996 and the aperture 1010, and inserting the dovetail 1002 into the dovetail cutout 1042 so that the collar 996 is received in the aperture 1226 of the rotating driven member 318, with the mortise 1000 of the nosepiece beam 994 in slidable registry with the end wall slot 952. As so assembled, the sample size control assembly 242 can translate longitudinally relative to the firing cage 290 a distance defined by the length of the mortise 1000.

The firing cage 290 is received in one of the housing shells 232, 234, such as the right housing shell 234, so that the plunger 970 is seated in the trigger opening 360 and the spring arm 972 contacts the intermediate wall 364. The beam 968 is received in the intermediate trigger opening 370 and the distal trigger opening 374. The side rail 926 and the beam 1024 extend along the bottom wall 334, with the collar 996 of the nosepiece 300 extending through the nosepiece opening 454 and the nosepiece opening 448. The adjustment lever 1036 is received in the sample size selector slot 410, the forward stop 1038 is received in one of the distal slots 412, 414, and the rearward stop 1040 is received in one of the proximal slots 416, 418. The distal end wall 930 of the firing cage 290 will be positioned adjacent the distal end of the front trigger opening 460 so that the tooth 466 will be in cooperative registry with the inclined face 946. This enables the button 294 attached to the button boss 468 to be inwardly-depressed so that the tooth 466 can be urged inwardly against the inclined face 446, thereby urging the firing cage 290 in a distal direction. The resilient arm 1192 and the mounting block 1188 of the helical drive member 316 are received within the slot 435 in the side wall 330 of the right housing shell 234 distally of the stop rib 433 for slidable translation therein.

The latch plate 310 is supported by the latch plate support 390 with the plate portion 1050 received in the latch plate channel 392 so that the crown portion 1052 extends distally with the proximal end wall 932 of the firing cage 290 positioned intermediate the latch plate 310 and the inner wall 372. The spoon cannula carriage 312 is supported by the upper spoon cannula carriage rail 394 and the lower spoon cannula carriage rail 396, with the end slot 1102 of the end bearing 1098 in slidable registry with the lower spoon cannula carriage rail 396, and the end bearing 1098 slidably received between the carriage rails 394, 396. The cutting cannula carriage 314 is supported by the cutting cannula carriage cradle 430 along the barrel portion 1126. The helical drive member 316 is also supported by the arcuate surface 942 of the distal end wall 930 of the firing cage 290.

The latch 258 is installed by inserting the lateral beam 716 outwardly through the latch slot 350 so that a button 260 can be affixed to the button mount 724. The flange plate 720 will be in slidable registry with the dorsal face of the upper interior wall 380, with the tooth 702 in registry with the dorsal side of the upper interior wall 530 proximal of the lower latch opening 384. The hook 712 will extend vertically upwardly through the upper latch opening 346. The box portion 756 of the shuttle 270 will extend through the shuttle cavity 726. An elastic band 728 of suitable resiliency and dimension is extendable around each latch arm 708, 710 and the retainer boss 526 to urge the latch 258 toward the proximal wall 486. The latch 258 can be selectively translated alternately proximally and distally by movement of the button 260 and the lateral beam 716 along the latch slot 350.

The shuttle 270 is received in the right housing shell 234 with the distal end 752 of the shuttle 270 extending toward the distal wall 488 of the right housing shell 234 so that the lateral edge of the plate portion 754 and the end boss 828 are received in the shuttle slot 386. The lower rail 852 of the shuttle 270 is received in the slot 435 proximally of the stop rib 433. The side wall 802 of the box portion 756 will be in slidable registry with the swing arm cage 339. The box portion 756 will extend dorsally of the upper interior wall 380. The cam block retainer 280 and the end box 774 will extend dorsally approximately the same height as the upper interior wall 380. The arcuate surface 790 of the cradle wall 786 will slidably register with the annular wall 1184 of the helical drive member 316 with the cradle wall 786 in registry with the distal side of the semicircular rib 1186. The cam block 278 is slidably inserted into the cam block retainer 280 so that the inner flange 768 and the outer flange 770 of the cam block retainer 280 are received in the channelways 910, 912 and the upper block 900 extends dorsally of the flanges 768, 770. The spring retainer 272 is slidably inserted into the chamber 820 of the box portion 756 so that the spring 274 encircles the rod 870 of the spring retainer 272 and the spring boss 864 of the box portion 756. The flange 872 of the spring retainer 272 can then be inserted into the spring retainer chamber 366 of the right housing shell 234 with the rod 870 extending through the spring retainer opening 368.

The left housing shell 232 can be assembled to the right housing shell 234 with the internal components seated in and supported by the cooperative elements of both the left housing shell 232 and the right housing shell 234.

With the left housing shell 232 and the right housing shell 234 assembled into the housing 230, the handle 250 can be installed to the housing 230 by inserting the pivot bosses 636 into the pivot apertures 442, 592. The spring mounting bosses 646 are inserted into the center apertures 660 of the mounting arm 650 for frictional registry of the mounting arm 650 with the handle 250. The mounting arm 650 is oriented to extend intermediate the swing arm supports 642 with the contact arm 652 depending away from the handle 250 proximally of the swing arm supports 642. The pivot rod 680 of the swing arm 256 is snapfit into the pivot openings 644 of the swing arm supports 642 so that the sliding rod 676 is disposed away from the handle 250 and the swing arm 256 is disposed distally of the contact arm 652. The end boss 678 is received in the swing arm chamber 342 for slidable translation therealong between the swing arm opening 340 and the proximal end 344. The end boss 678 can be inserted into the swing arm chamber 342 through the swing arm opening 340, and will be housed in the proximal end 344 with the swing arm support 642 received through the swing arm opening 340 when the handle 250 is pivoted ventrally to a closed position in registry with the housing 230.

Figure 49:
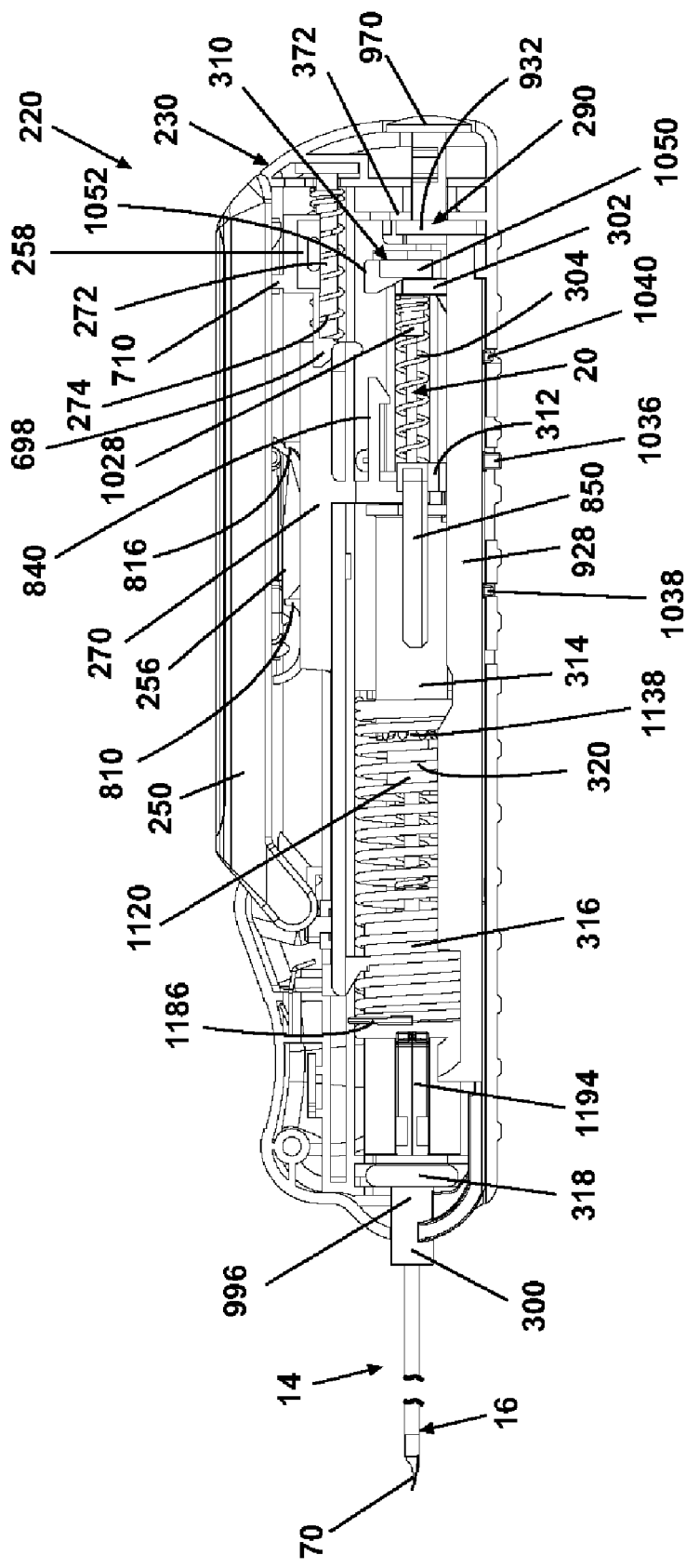
FIG. 49 is a left elevational view of the core biopsy device illustrated in FIG. 24 illustrating the core biopsy device in an uncocked and fired configuration, with elements removed for clarity.
Figure 49A:
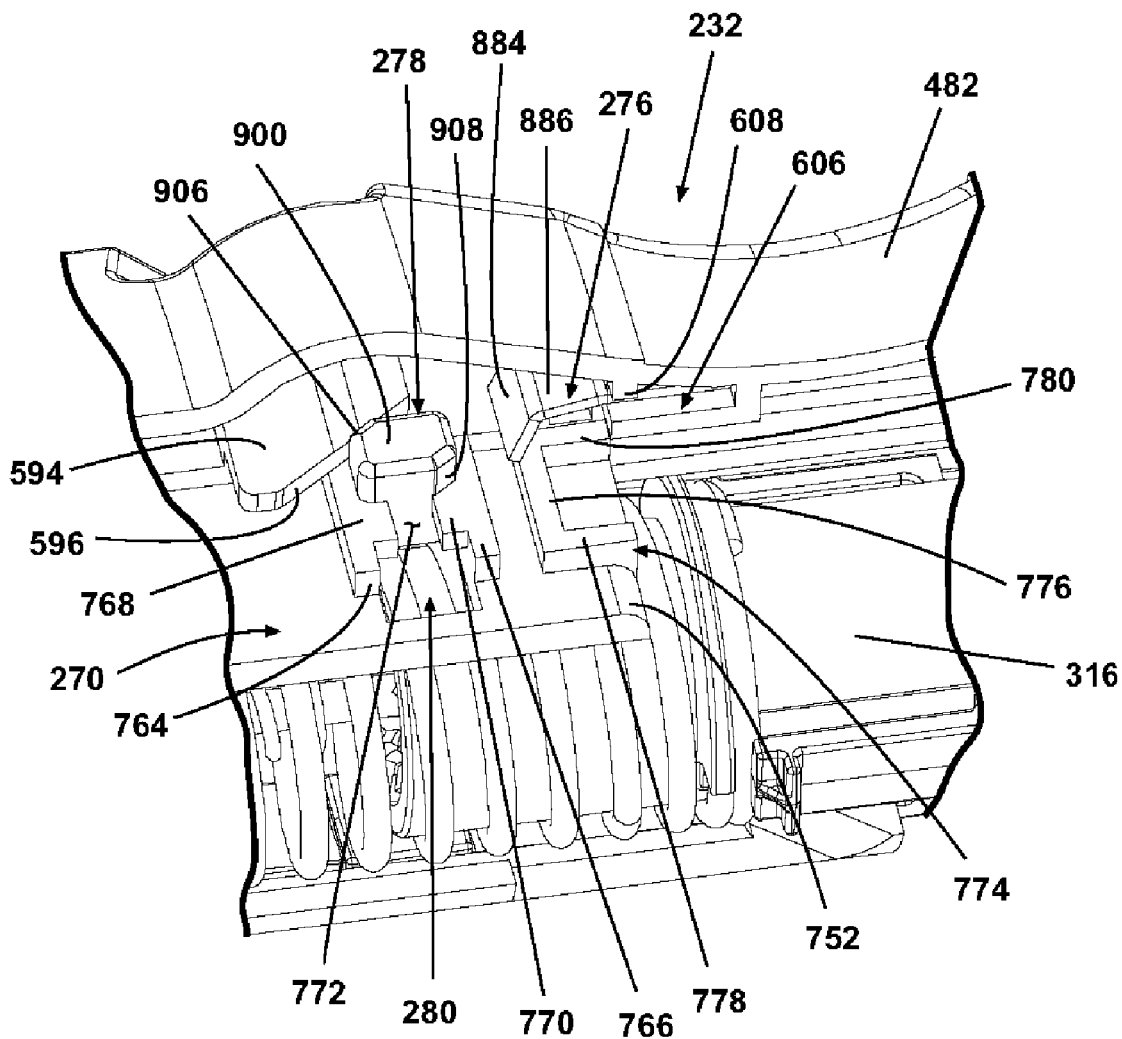
FIG. 49A is a partial cutaway perspective view of a portion of the core biopsy device illustrated in FIG. 24 illustrating the cam block in a first position during cocking of the device.

As illustrated in FIG. 49A, the cam spring 276 is attached to the left housing shell 232 so that the upper leg 880 is received in the cam spring housing 606 with the inclined member 890 in registry with the stop wall 608 and the lower leg 884 depending toward the distal end 752 of the shuttle 270. The opposite shell, in this example the right housing shell 234, is then brought into mating registry with the left housing shell 232 to form the housing 230. The assembled elements will cooperatively engage the right housing shell 234 in a manner similar to the engagement of the assembled elements with the left housing shell 232, as hereinbefore described.

The operation of the biopsy gun 220 will now be described with reference to FIGS. 49-56. In the Figures, elements of the biopsy gun 220, particularly the housing shells 232, 234, will be either removed or illustrated in phantom to facilitate a complete understanding of the operation of the gun 220. The biopsy gun 220 is initially in an uncocked condition, and must be cocked prior to introducing the cannula assembly 14 into the tissue mass 22. As described previously herein and illustrated in FIG. 9A, with the biopsy gun 220 in a cocked condition, the cannula assembly 14 is inserted into the tissue mass 22 so that the penetration tip 34 is adjacent the lesion 24. The biopsy gun 220 is then fired by operation of the firing cage 290 for excision of a biopsy sample.

As illustrated in FIG. 49, in the uncocked condition, the biopsy gun 220 is initially in a configuration with the handle 250 extending along the dorsal side 226 of the housing 230. The latch 258, under the influence of the elastic band 728, is urged towards the proximal end 224 of the housing 230 with the hooks 710, 712 of the latch 258 in cooperative registry with the hook 640 of the latch extension 638 to retain the handle 250 against the housing 230. Under the influence of the spring 274, the shuttle 270 is urged toward the distal end 222 of the housing 230. Under the influence of the spring 304, the spool cannula carriage 312 and the cutting cannula carriage 314 are also urged toward the distal end 222 of the housing 230. The spring 254 is deflected into a generally linear configuration, with the swing arm 256 partially received in the housing 230. The cam block 278 will be urged to the left side of the housing 230 by engagement of the inclined face 906 with the inclined face 446 of the distal cam block wedge 444 extending inwardly from the right housing shell 234. The cam block 278 will thus be longitudinally aligned with the cam spring 276.

Figure 50:
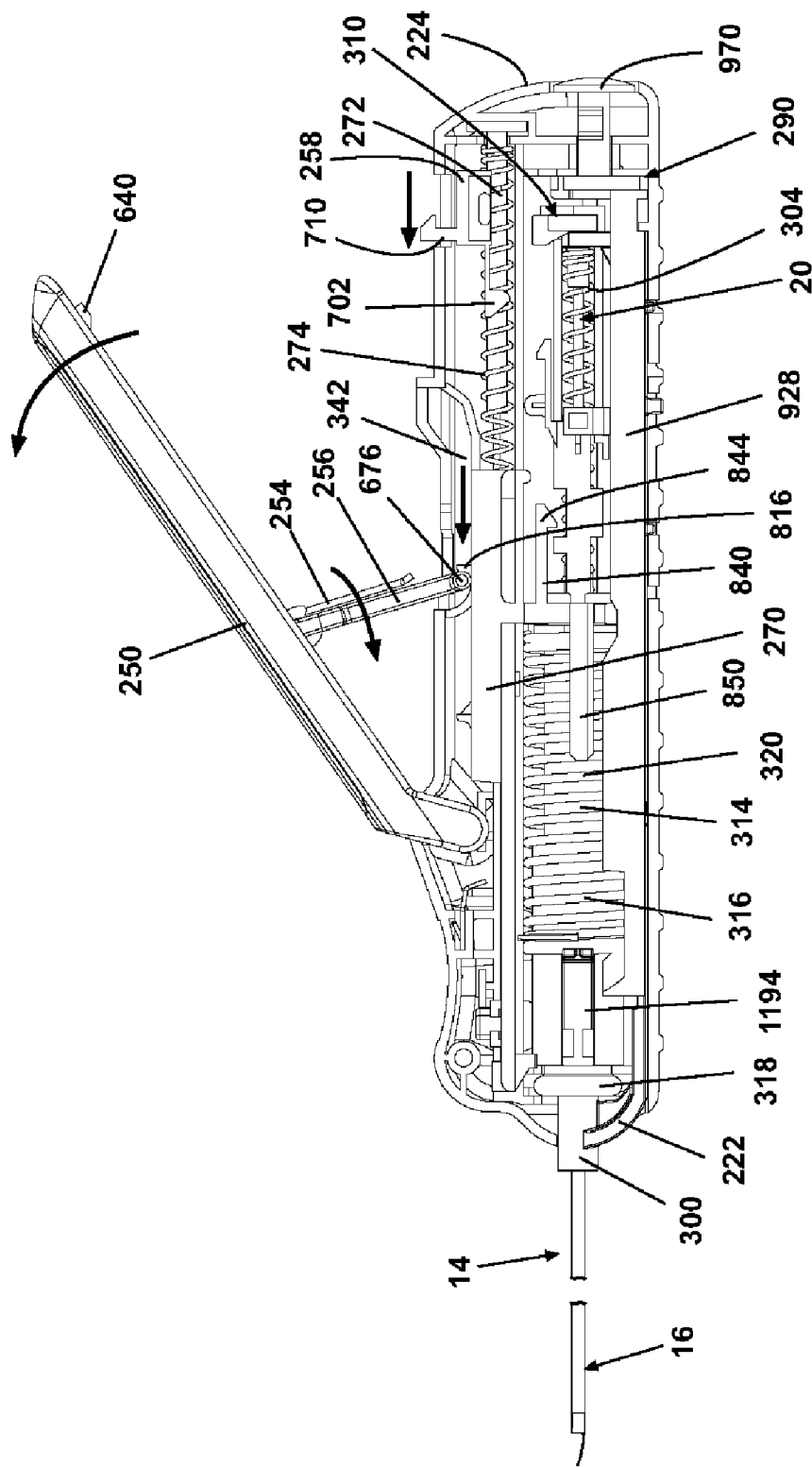
FIG. 50 is a left elevational view of the core biopsy device illustrated in FIG. 24 illustrating the core biopsy device in a first configuration ready for cocking, with elements removed for clarity.

As illustrated in FIG. 50, the handle 250 is released by translating the buttons 260 at the proximal end 224 toward the distal end 222, which will translate the hooks 710, 712 away from the hook 640, and will "drop" the teeth 702, 704 into an interference registry with the lower latch opening 534, 384, respectively. This will prevent the translation of the latch 258 toward the proximal end 224, notwithstanding the tension exerted by the elastic band 728 tending to urge the latch 258 toward the proximal end 224. The handle 250 will be urged into an open position by the spring 254, which will also move the swing arm 256 to an oblique orientation as the end bosses 678 translate from the proximal end 344, 494 along the swing arm chamber 342, 492 to the swing arm opening 340, 490. The sliding rod 676 translates along the swing arm chamber 342, 492 and the top wall 800 of the shuttle 270, and over the outer bearing wall 816 into cooperative registry with the arcuate surface 818 of the outer bearing wall 816 extending dorsally of the top wall 800 of the shuttle 270.

Figure 51:
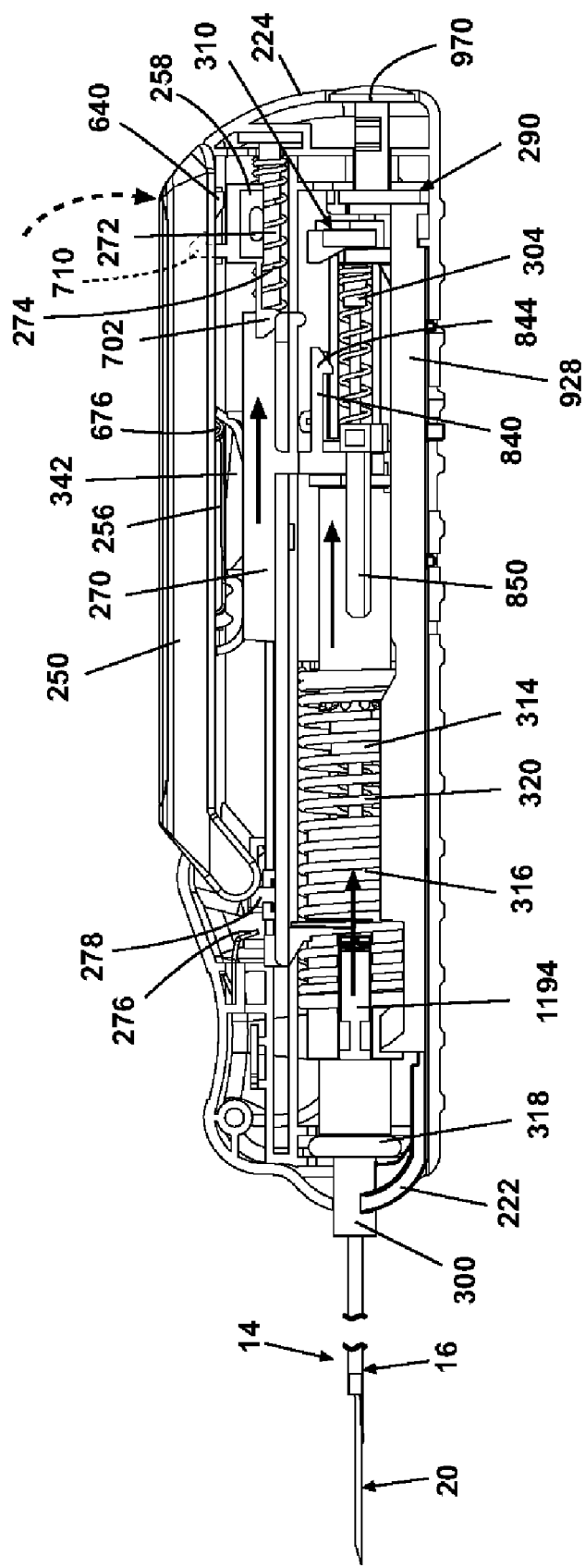
FIG. 51 is a left elevational view of the core biopsy device illustrated in FIG. 24 illustrating the core biopsy device in a first cocked configuration, with elements removed for clarity.

Referring now to FIG. 51, with the sliding rod bearing against the outer bearing wall 816, depressing the handle 250 toward the shell 230 will translate the shuttle 270 toward the proximal end 224. This will urge the helical drive member 316 toward the proximal end 224 due to the registry of the cradle wall 786 with the semicircular rib 1186, thereby compressing the spring 320 between the semicircular rib 1186 and the cutting cannula carriage cradles 430, 580. The resilient arms 1192, 1194 of the helical drive member 316 will be deflected radially inwardly by engagement of the braces 1204, 1206, respectively, with the stop ribs 583, 433 of the left and right housing shells 232, 234, respectively, until the hooks 1196, 1198 clear the ribs 583, 433 to return to an undeflected position in which the hooks 1196, 1198 are in registry with the proximal face of the ribs 583, 433, respectively, thus preventing the helical drive member 316 from moving toward the distal end 222 under the influence of the spring 320. The coring cannula 16 will be drawn over the stylet 20 and the spoon cannula 18 in a proximal direction.

During movement of the shuttle 270 toward the proximal end 224, the cam block 278 will be brought beneath the cam spring 276 thereby causing deflection of the lower leg 884 toward the dorsal side 226 of the housing 230. When the cam block 278 moves past the cam spring 276, the lower leg 884 will return to its initial at-rest position. The handle 250 can be fully depressed toward the shell 230 without engaging the latch 258 due to the retention of the latch 258 toward the distal end 222 and the registry of the hooks 702, 704 with the lower latch openings 384, 534, as previously described.

Figure 52:
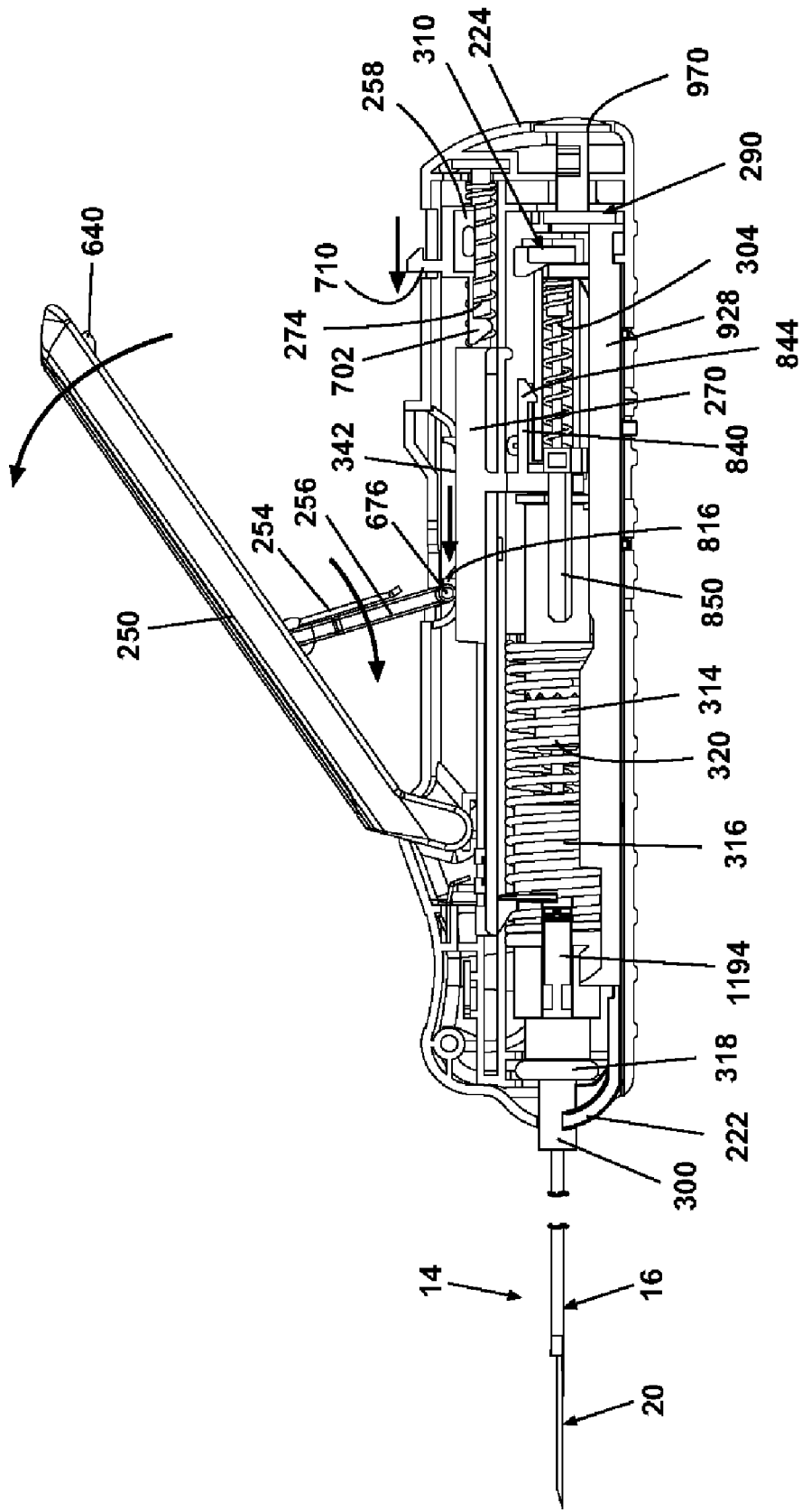
FIG. 52 is a left elevational view of the core biopsy device illustrated in FIG. 24 illustrating the core biopsy device in a second configuration ready for cocking, with elements removed for clarity.

As illustrated in FIG. 49A, the shuttle 270 will be prevented from returning to its initial position by the interference between the cam block 278 and the lower leg 884 of the cam spring 276, which will engage the upper block 900 and prevent movement of the shuttle 270 toward the distal end 222. As illustrated in FIG. 52, the handle 250 can again be released to the open position by the operator merely opening his or her hand, without the necessity of translating the buttons 260 toward the distal end 222 as before, with the sliding rod 676 brought into cooperative registry with the arcuate surface 812 of the inner bearing wall 810 extending dorsally of the top wall 800 of the shuttle 270, since the inner bearing wall 810 will now be positioned where the outer bearing wall 816 was previously positioned. The inclined brace 814 will facilitate movement of the sliding rod 676 from the outer bearing wall 816 into engagement with the arcuate surface 812.

Figure 53:
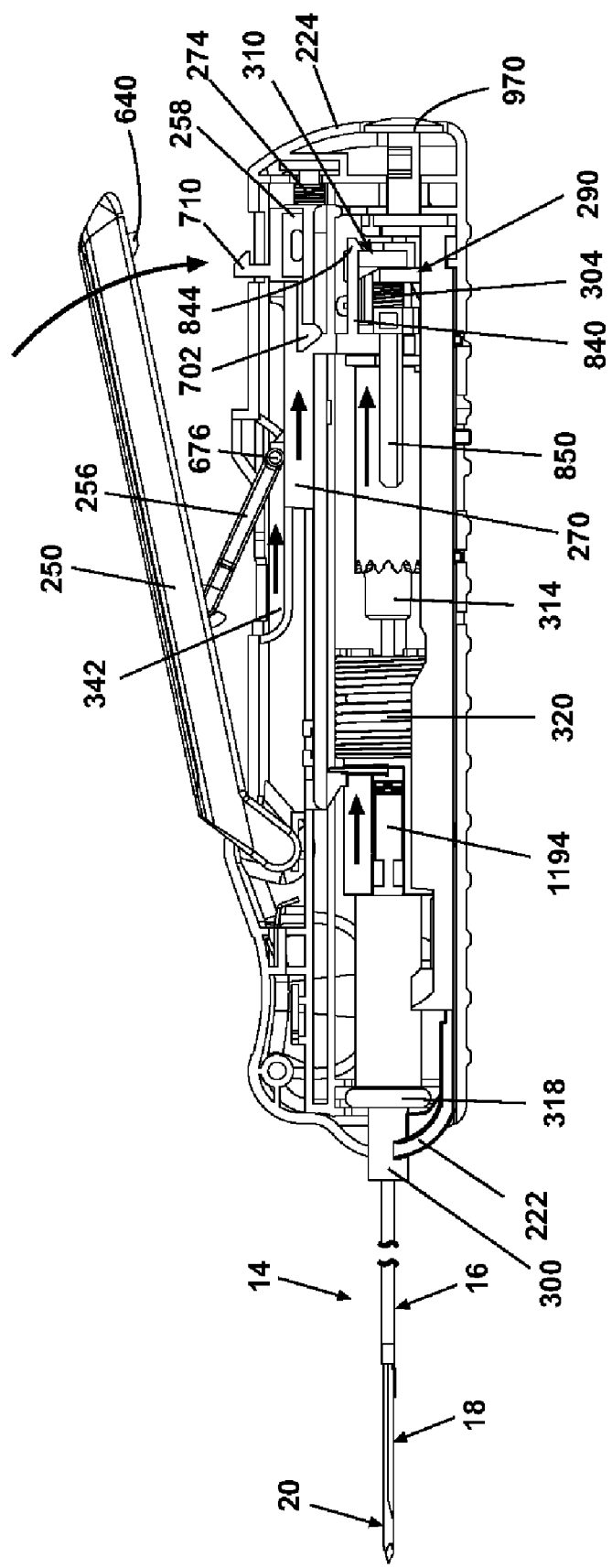
FIG. 53 is a left elevational view of the core biopsy device illustrated in FIG. 24 illustrating the core biopsy device being placed in a second cocked configuration, with the elements removed for clarity.

As illustrated in FIG. 53, depressing the handle 250 toward the shell 230 will again translate the shuttle 270 toward the proximal end 224. As the shuttle 270 translates toward the proximal end 224, the end bosses 826, 828 extending laterally away from the box portion 756 will engage the teeth 702, 704, respectively, of the latch 258, urging the teeth 702, 704 upwardly out of the lower latch openings 534, 384, respectively. Under the influence of the elastic band 728, the latch 258 will be urged toward the proximal end 224 for engagement with the handle 250. Thus, the handle 250 will be retained in a closed position against the housing 230 without the necessity of resetting the position of the latch 258. This structure permits the user to release the handle, squeeze the handle twice to cock the actuator, with the handle automatically springing up after the first squeezing of the handle, and locking in the closed position upon the second squeezing, which enable one-handed cocking of the actuator.

The hooks 844, 846 extending from the intermediate wall 830 of the shuttle 270 will engage the plate portion 1050 of the latch plate 310 on both sides of the crown portion 1052, thus retaining the shuttle 270 at its proximal limit, with the spring 274 fully compressed. The spool cannula carriage 312 and the cutting cannula carriage 314 will also be translated proximally by the shuttle 270 as a result of the cradle 835 being received in the neck portion 1176 of the cutting cannula carriage 314. This will bring the hook 1108 extending from the spool cannula carriage 312 into an interference engagement with the opening 1060 in the crown portion 1052 of the latch plate 310. The spring 304 will also be fully compressed. The brace 1030 of the adjustment member 302 will be received in the barrel notch 1158 of the cutting cannula carriage 314. The braces 1094, 1096 of the spoon cannula carriage 312 will be received in the secondary notches 1154, 1156 of the cutting cannula carriage 314, and the notches 838 in the intermediate wall 830 of the shuttle 270, thereby ensuring nesting of the spoon cannula carriage 312, the cutting cannula carriage 314, and the shuttle 270.

Figure 49B:
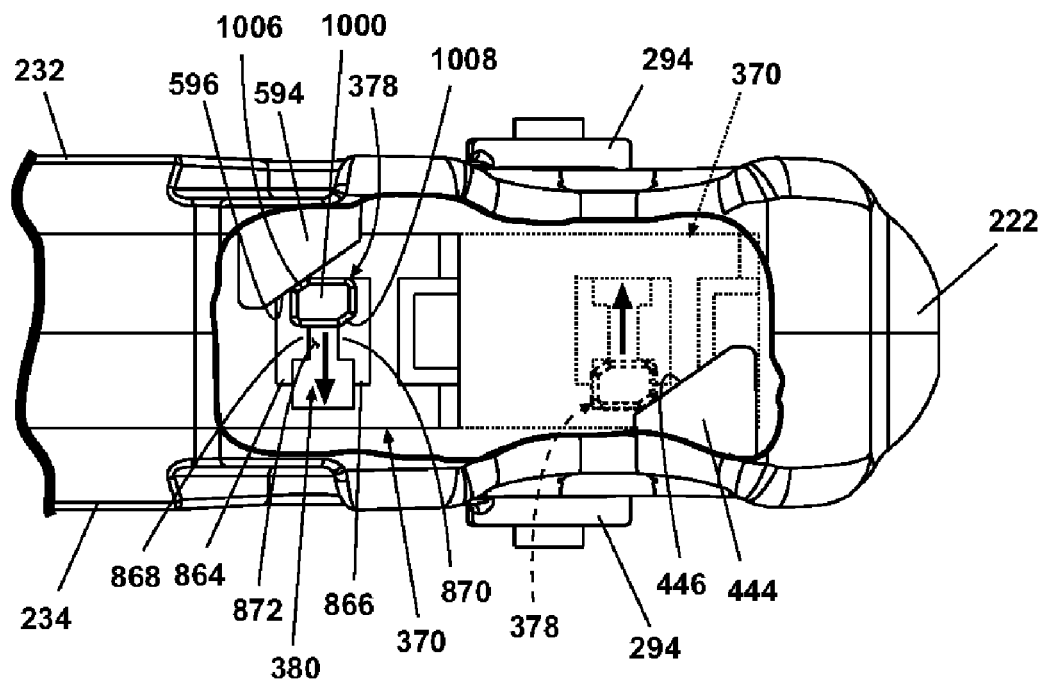
FIG. 49B is a partial cutaway plan view of a portion of the core biopsy device illustrated in FIG. 24 illustrating the cam block in a first position during cocking of the device, and in a second position during firing of the device, the second position being shown in phantom.

At the same time, the helical drive member 316 will be translated toward the distal wall 222 by engagement of the cradle wall 786 of the shuttle 270 with the semicircular rib 1186. This will fully compress the spring 320 between the semicircular rib 1186 and the cutting cannula carriage cradle 430, 580. Finally, as illustrated in FIG. 49B, the cam block 278 will be urged to the right side of the housing 230 by engagement of the inclined face 906 with the inclined face 596 of the proximal cam block wedge 594 extending inwardly from the left housing shell 232. In this configuration, the coring cannula 16 and the spoon cannula 18 will be fully retracted proximally, and the stylet 20 will extend distally of the coring cannula 16 and the spoon cannula 18, with the biopsy gun 220 in a cocked and ready position for obtaining a biopsy sample. The cannula assembly 14 can be introduced into the tissue mass 22 and advanced to the lesion 24 for recovery of the biopsy sample 26.

When the cannula assembly 14 has been positioned for recovery of the biopsy sample 26, the biopsy gun 220 is actuated. The biopsy gun 220 can be actuated in one of two ways to obtain the biopsy sample 26. Both procedures actuate the firing cage 290. In the first procedure, the firing plunger 292 is depressed toward the distal end 222. In the second procedure, the buttons 260 at the lower distal end of the housing 230 are depressed laterally inwardly. This urges the release arms 462, 612 laterally inwardly, which urges the teeth 466, 616 inwardly against the inclined faces 944, 946 of the distal end wall 930, thereby urging the firing cage 290 toward the distal end 222.

Figure 54:
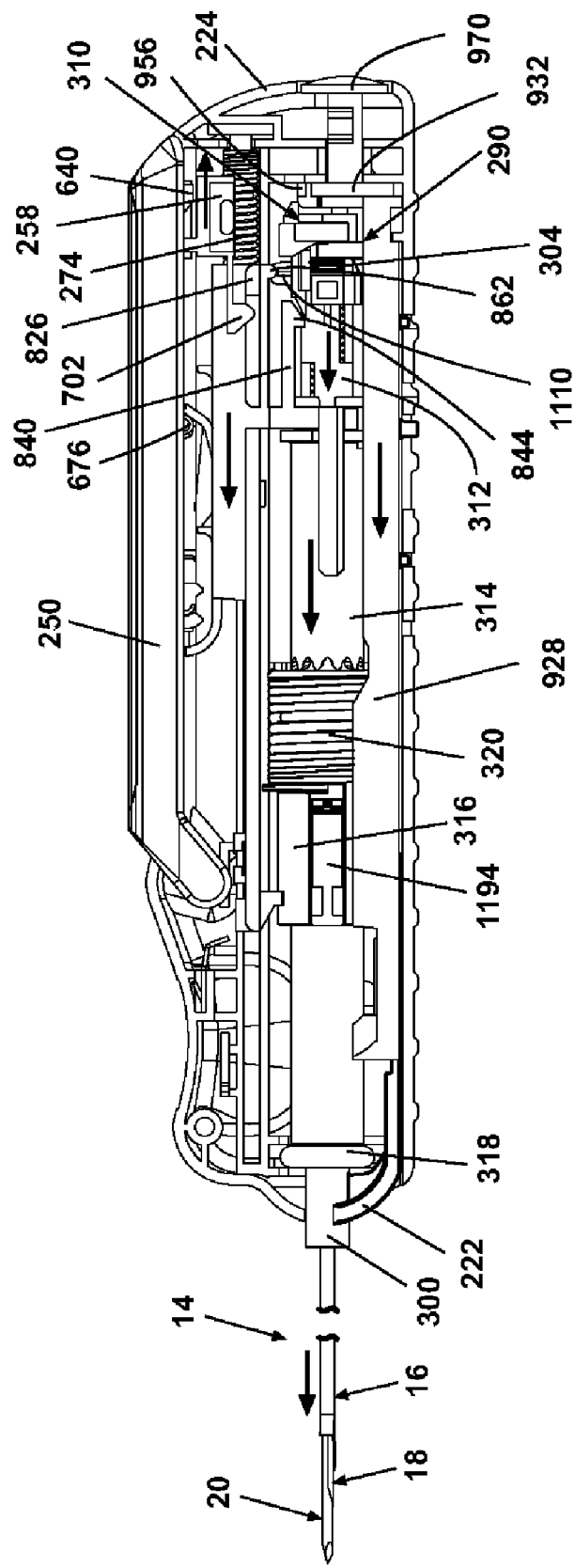
FIG. 54 is a left elevational view of the core biopsy device illustrated in FIG. 24 illustrating the core biopsy device in an initial fired position with the spoon cannula and the coring cannula being advanced for introduction into a lesion.

As illustrated in FIG. 54, as the firing cage 290 translates toward the distal end 222, the flanges 956, 958 of the proximal end wall 932 engage the hooks 844, 846 of the shuttle 270, urging the hooks 844, 846 dorsally out of engagement with the latch plate 310. This will release the shuttle 270 for translation toward the distal end 222 under the influence of the spring 274. This will translate the cutting cannula carriage 314 toward the distal end 222, which will initiate the movement of the coring cannula 16 over the spoon cannula 18, with the excising finger 70 translating along the arcuate wall 46 of the spoon cannula 18.

Figure 55:
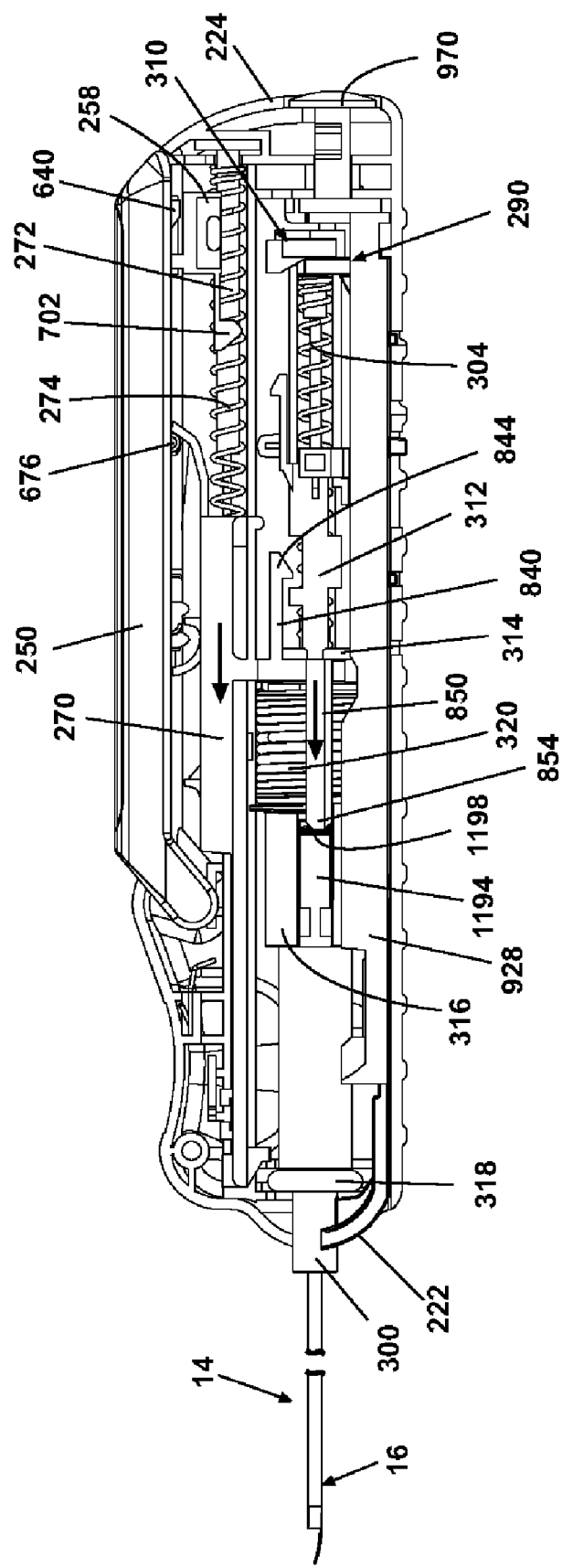
FIG. 55 is a left elevational view of the core biopsy device illustrated in FIG. 24 illustrating the core biopsy device in an intermediate fired position with the coring cannula being advanced beyond the spoon cannula for excision of a biopsy sample.

As the shuttle 270 continues to translate toward the distal end 222, the end boss 862 depending from the box portion 756 will engage the fin 1110 extending dorsally from the resilient arm 1106 of the spoon cannula carriage 312. This will deflect the resilient arm 1106 ventrally, releasing the hook 1108 from the latch plate 310, and enabling the spoon cannula carriage 312 to move toward the distal end 222 under the influence of the spring 304. The cutting cannula carriage 314 and the spoon cannula carriage 312 will thus translate toward the distal end 222, thereby urging the coring cannula 16 and the spoon cannula 18 into the lesion 24. The cutting cannula carriage 314 will be brought into engagement with the rotating driven member 318 and thus prevented from further translation toward the distal end 222. The spoon cannula carriage 312 will bottom out as the end bearings 1098, 1100 engage the stops 398, 400 in the right housing shell 234 and the stops 548, 550 in the left housing shell 232, respectively. The cutting cannula carriage 314 will bottom out after the spoon cannula carriage 312 bottoms out due to the engagement of the cutting cannula carriage 314 with the rotating driven member 318, so that the excising finger 70 extends distally of the insertion tip 48 of the spoon cannula 18, as illustrated in FIG. 55.

As the shuttle 270 continues to translate toward the distal end 222, the lower rails 850, 852 will translate in the slots 435, 585, toward the stop ribs 433, 583. The end portions 854, 858, of the lower rails 850, 852, respectively, will engage the resilient arms 1194, 1192, respectively. As illustrated in FIG. 55, the tapered tips 856, 860 of the end portions 854, 858, respectively, will engage the braces 1206, 1204, respectively, of the hooks 1198, 1196, urging the radially-inward deflection of the resilient arms 1194, 1192, respectively. This will urge the hooks 1198, 1196 out of registry with the stop ribs 433, 583, freeing the helical drive member 316 to translate toward the distal end 222 under the influence of the spring 320. As illustrated in FIG. 49B, the cam block 378 will be urged against the inclined face 446 of the distal cam block wedge 444, and translated along the gap 772 of the cam block retainer 280 toward the left housing shell 232.

Figure 56:
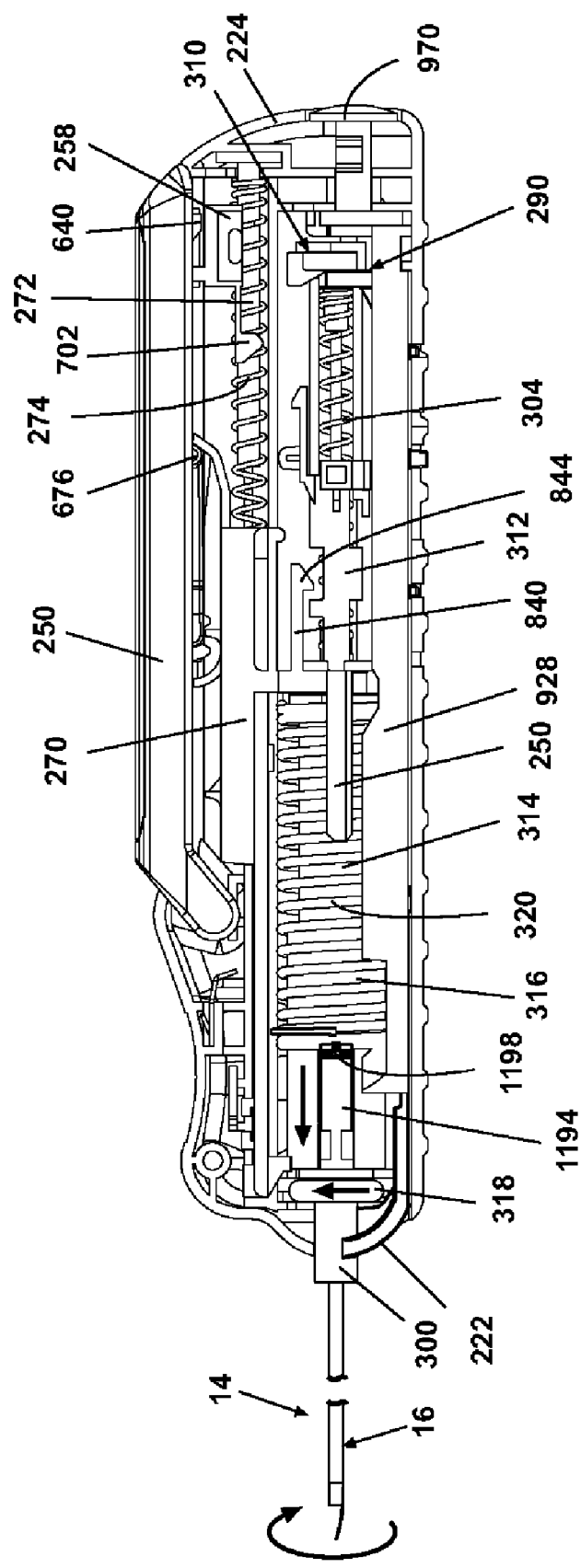
FIG. 56 is a left elevational view of the core biopsy device illustrated in FIG. 24 illustrating the core biopsy device in a final fired position with the coring cannula being rotated for excision of a biopsy sample.

Referring to FIG. 56, as the helical drive member 316 translates, the rotating driven member 318 will be urged into rotation by the rotational motion of the helical channelway 1202 acting on the boss 1222. Rotation of the rotating driven member 318 will urge the rotation of the cutting cannula carriage 314 due to the interlocking of the teeth 1218 and channels 1220 of the rotating driven member 318 with the channels 1142 and teeth 1140, respectively, of the cutting cannula carriage 314. This will urge the excising finger 70 in a rotational motion, excising the sample 26 from the lesion 24. The cannula assembly 14 can then be withdrawn from the tissue mass 22 with the biopsy sample 26 retained in the spoon section 42 of the spoon cannula 18.

It is highly preferred that the rotation of the excising finger not begin until the excising finger has reached its longitudinal extent. This prevents the rotation of the excising finger from cutting a helical path in the sample. The helical channelway 1202, the helical drive member 316, and the boss 1222 are preferably adapted so that the cutting cannula carriage 314 and the coring cannula 16 rotate 1½ turns with a complete stroke of the helical drive member 316. More than one complete revolution increases the likelihood that the sample is completely severed.

While it is preferred to have more than one revolution of rotation for the excising finger to ensure separation, the amount of rotation needed to ensure the separation of the sample from the surround tissue can vary. In some cases, less than a complete revolution is sufficient. For example, when the excising finger extends substantially across the diameter of the coring cannula or when the suction and friction forces between the specimen and cannula are sufficiently high. Multiple revolutions can also be used. There is no theoretical limit to the number of revolutions. However, it is anticipated that 1½ revolution is sufficient.

As a result of the above-described firing of the biopsy gun 220, the coring cannula 16 is propelled over the spoon section 42 so that the excising finger 70 is positioned slightly proximally of the insertion tip 48 (FIG. 8B). The coring cannula 16 and the spoon cannula 18 then translate simultaneously into the lesion 24 to form the biopsy sample (FIG. 9B). The coring cannula 16 is further projected relative to the spoon cannula 18 so that the excising finger 70 disengages from the spoon cannula 18 to penetrate the tissue mass 22 distally of the biopsy sample (FIGS. 8C and 9C). The translation of the helical drive member 316 urges the boss 1222 along the helical channelway 1202, thereby urging the cutting cannula carriage 314 to rotate in a counterclockwise direction, thereby rotating the coring cannula 16 relative to the spoon cannula 18, so that the excising finger 70 excises the biopsy sample from the tissue mass 22 (FIG. 9D). The core biopsy device 10 is then removed from the tissue mass 22 with the biopsy sample enclosed therein (FIGS. 9E and 9F). Re-cocking of the biopsy gun 220 retracts the coring cannula 16 away from the spoon section 42, thereby exposing the biopsy sample 26 for removal (FIG. 9G).

Alternately, the biopsy gun 220 can be adapted to position the cannulae 16, 18 upon cocking of the biopsy gun 220 as shown in FIG. 8D. In this configuration, the enclosed section 60 of the coring cannula 16 is essentially coextensive with the enclosed section 40 of the spoon cannula 18, thus eliminating the semi-annular gap 88 between the stylet 20 and the annular wall 62 of the coring cannula 16. The distal edge of the excising finger 70 is in resilient contact with the arcuate wall 46 at the proximal end of the spoon section 42. The cannula assembly 14 is advanced into the tissue 22 as previously described, followed by the simultaneous advancement of the cannulae 16, 18 into the lesion 26. The coring cannula 16 is then advanced over the spoon cannula 18 through the lesion 26 until the excising finger 70 extends distally of the insertion tip 48 to position the coring cannula 16 for excision of the sample 26.

The core biopsy device 10 described herein provides several distinct advantages over the prior are which increase the probability of obtaining a high-quality biopsy sample. The use of a spoon-shaped biopsy sample support minimizes the disturbance and degradation of the sample which can occur with devices having enclosed sample chambers requiring the sample be ejected by a plunger, the stylet, or similar means. This avoids the necessity of obtaining a second sample if the first one proves to be unusable. Additionally, the use of the rotational cutting mechanism ensures that the sample is completely excised from the surrounding tissue mass, thereby minimizing the potential for disturbance or degradation of the sample when pulling the sample away from the tissue mass in order to sever it. This also minimizes the potential that the sample will separate from the tissue mass at a location within the sample itself rather than at its attachment to the tissue mass, thereby avoiding a sample volume which is inadequate for analysis. Finally, the core biopsy device 10 can be inserted, cocked, and actuated by an operator using one hand, thereby enabling the operator to concurrently operate an imaging device, such as an ultrasound wand, for positioning the cannula assembly 14, eliminating the need for an additional imaging technician. Thus, the core biopsy device 10 is easily inserted and triggered with one hand, providing very quick recovery of a biopsy sample, thereby enhancing the quality of the biopsy sample and minimizing discomfort to the patient.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention, which is defined in the appended claims.

What is claimed is:

1. A biopsy apparatus for the percutaneous removal of a specimen from a tissue mass, the biopsy apparatus comprising:
   an outer cannula defining a lumen and a longitudinal axis, the outer cannula having a proximal end, a distal end, an opening formed in the distal end, and an excising finger extending from the distal end;
   an inner cannula received within the lumen, the inner cannula defining a longitudinal axis and having a proximal end, a distal end, and an open-tipped spoon portion that terminates at the distal end of the inner cannula; and
   an actuator operably coupled to at least the outer cannula and configured to axially move, without rotating, the excising finger along the spoon portion from an inserting position, in which the excising finger does not extend distally of the spoon portion, to an excising position, in which relative axial movement of the excising finger ceases and the excising finger is distal of the spoon portion and extends toward the longitudinal axis of the inner cannula, and to initiate rotation of the excising finger about the longitudinal axis of the outer cannula when the excising finger is in the excising position;
   wherein the spoon portion supports the specimen distally of the opening of the outer cannula when at least a portion of the spoon portion extends exteriorly through the opening of the outer cannula, whereby the specimen can be removed from the inner cannula.

2. The biopsy apparatus according to claim 1, wherein the excising finger is adapted for resilient flexure.

3. The biopsy apparatus according to claim 2, wherein the flexure of the excising finger is alternately between a first position generally parallel to the longitudinal axis of the inner cannula and a second position toward the longitudinal axis of the inner cannula.

4. The biopsy apparatus according to claim 3, wherein the excising finger is configured to be in the first position during axial movement along the spoon portion.

5. The biopsy apparatus according to claim 4, wherein the excising finger is configured to flex from the first position toward the second position as the excising finger axially slides past the spoon portion.

6. The biopsy apparatus according to claim 1, wherein the shape of the excising finger is at least one of arcuate, rectilinear, and trapezoidal.

7. The biopsy apparatus according to claim 1, wherein the excising finger extends at least to the longitudinal axis of the outer cannula in the excising position.

8. The biopsy apparatus according to claim 1, wherein the actuator is operably coupled to both of the outer and inner cannulae, and is configured to axially advance the outer cannula and the inner cannula when moving the excising finger to the excising position.

9. The biopsy apparatus according to claim 8, wherein the actuator is configured to stop the axial advancement of the inner cannula prior to the excising finger reaching the excising position.

10. The biopsy apparatus according to claim 1, wherein the spoon portion comprises an arcuate cross section.

11. The biopsy apparatus according to claim 10, wherein the arcuate cross section spans an arc of 180 degrees or less.

12. The biopsy apparatus according to claim 10, wherein the arcuate cross section spans an arc of greater than 180 degrees.

13. The biopsy apparatus according to claim 10, wherein the spoon portion terminates in a sharpened edge.

14. The biopsy apparatus according to claim 1, and further comprising a stylet received within the inner cannula to substantially close off the inner cannula in the inserting position.

15. The biopsy apparatus according to claim 14, wherein the actuator is configured to axially advance the outer cannula relative to the stylet when moving the excising finger to the excising position to form a tissue receiving area between the distal end of the outer cannula and the stylet.

16. The biopsy apparatus according to claim 15, wherein the position of the stylet is adjustable relative to the excising position of the excising finger to provide for adjusting the length of the tissue receiving area.

17. The biopsy apparatus according to claim 1, wherein the actuator, inner cannula, and outer cannula collectively define an integrated self-contained hand-holdable device.

18. The biopsy apparatus according to claim 1, wherein the actuator is configured to rotate the outer cannula at least a partial revolution.

19. The biopsy apparatus according to claim 18, wherein the actuator is configured to rotate the outer cannula for at least one revolution.

20. The biopsy apparatus according to claim 19, wherein the outer cannula is configured to rotate at least 1½ revolution.

21. The biopsy apparatus according to claim 1 wherein the actuator comprises a hollow interior and a carriage slidably mounted within the hollow interior and configured to carry the outer cannula whereby the slidable movement of the carriage moves the outer cannula to the excising position.

22. The biopsy apparatus according to claim 21 wherein the actuator further comprises a driver operably coupled to the carriage to rotate the carriage and thereby effect the rotation of the outer cannula.

23. The biopsy apparatus according to claim 22 wherein the actuator further comprises a clutch operably coupling the driver to the carriage when the outer cannula is moved to the excising position.

24. The biopsy apparatus according to claim 23 wherein the carriage comprises a gear, the driver comprises a helical slot, and the clutch comprises a driven member keyed to the helical slot and having a gear that meshes with the gear of the carriage when the outer cannula is in the excising position such that the axial movement of the driven member rotates the driven member to effect the rotation of the carriage.

25. The biopsy apparatus according to claim 24 wherein the actuator comprises a first biasing device for sliding the carriage to move the outer cannula to the excising position.

26. The biopsy apparatus according to claim 25 wherein the actuator further comprises a second biasing device for axially moving the driver relative to the driven member.

27. The biopsy apparatus according to claim 1 and further comprising a dual trigger to trigger movement of the outer cannula, wherein the dual trigger comprises a first trigger located at a first portion of the actuator and a second trigger located at a second portion of the actuator.

28. The biopsy apparatus according to claim 27 wherein the first portion is near the front of the actuator and the second portion is near the rear of the actuator.

29. The biopsy apparatus according to claim 27 wherein the actuator can be triggered by actuating either one of the first trigger and the second trigger.

30. The biopsy apparatus according to claim 1 wherein the actuator further comprises a lever pivotally movable between a first, open position and a second, closed position and the lever is spring-biased to the first, open position, and a latch movable between a first latch position to prevent the lever from moving from the second, closed position to the first, open position and a second latch position to permit the lever to move from the second, closed position to the first, open position.

31. The biopsy apparatus according to claim 30 wherein the latch is configured such that the latch moves to the second latch position when the lever has twice moved to the second, closed position.

32. The biopsy apparatus according to claim 30 wherein the latch is configured such that, after movement to the first latch position, the latch moves to the second latch position when the lever has twice moved to the second, closed position.

33. A method of conducting a percutaneous biopsy by removing a specimen core from a predetermined site in a tissue mass, the method comprising:
 axially advancing, without rotating, an outer cannula defining a lumen into the predetermined site in the tissue mass to at least partially form a specimen core containing at least a portion of the tissue at the predetermined site, with the specimen core having a proximal portion contained within the outer cannula and a distal portion attached to the tissue mass and the outer cannula having a proximal end, a distal end, an opening formed in the distal end, and an excising finger extending from the distal end;
 axially advancing an inner cannula having a proximal end and a distal end and terminating at the distal end in an open-tipped spoon portion within the lumen of the outer cannula such that the specimen core is at least partially supported by the spoon portion;
 extending the excising finger along and beyond the spoon portion, and into the distal portion of the specimen core;
 rotating the outer cannula to sever the distal portion of the specimen core from the surrounding tissue;
 withdrawing the outer cannula and inner cannula from the tissue mass; and
 relatively moving the cannulae such that at least a portion of the spoon portion extends exteriorly through the opening of the outer cannula to expose the specimen core supported on the spoon portion to permit the removal of the specimen core therefrom.

34. The method according to claim 33, and further comprising at least partially inserting the inner cannula into the outer cannula prior to the advancement of the outer cannula.

35. The method according to claim 33, wherein the rotating the outer cannula comprises rotating the outer cannula at least a partial revolution.

36. The method according to claim 35, wherein the rotating the outer cannula comprises rotating the outer cannula at least one revolution.

* * * * *

UNITED STATES PATENT AND TRADEMARK OFFICE
CERTIFICATE OF CORRECTION

| | |
|---|---|
| PATENT NO. | : 8,088,081 B2 |
| APPLICATION NO. | : 10/908427 |
| DATED | : January 3, 2012 |
| INVENTOR(S) | : Steven E. Field et al. |

Figure 11A:
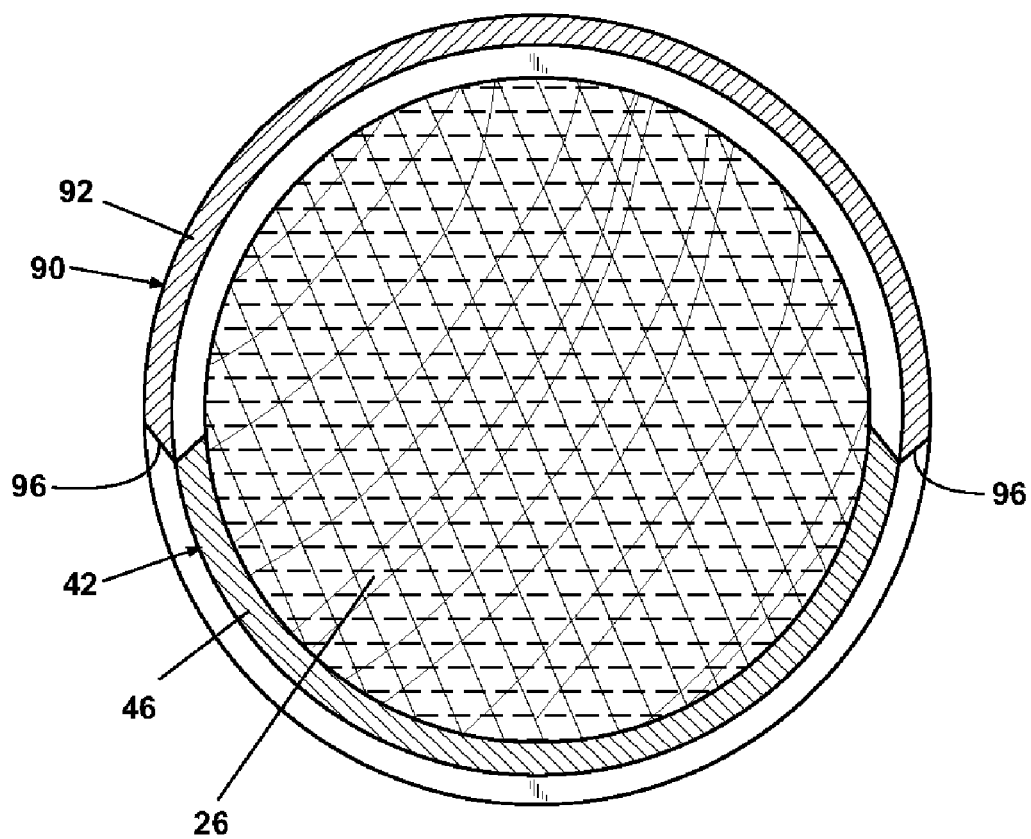
FIG. 11A is a sectional view similar to that taken along view line 11A-11A illustrating the spoon cannula supporting a core biopsy sample and the coring cannula rotated to diametrically juxtapose the cannulae spoon sections to enclose the core biopsy sample.

It is certified that error appears in the above-identified patent and that said Letters Patent is hereby corrected as shown below:

Col. 13, lines 12-15: "The coring cannula 16 will be rotated so that the annular wall 92 is diametrically disposed relative to the annular wall 44 to form a generally enclosed tubular sample retaining cavity (FIG. 1A)." - should be -- The coring cannula 16 will be rotated so that the annular wall 92 is diametrically disposed relative to the annular wall 44 to form a generally enclosed tubular sample retaining cavity (FIG. 11A). --

Signed and Sealed this
Fifteenth Day of May, 2012

David J. Kappos
*Director of the United States Patent and Trademark Office*